(12) United States Patent
Askari et al.

(10) Patent No.: US 11,596,710 B2
(45) Date of Patent: *Mar. 7, 2023

(54) BIOCOMPATIBLE HYDROGEL TREATMENTS FOR RETINAL DETACHMENT

(71) Applicant: C.P. MEDICAL CORPORATION, Norcross, GA (US)

(72) Inventors: Syed H. Askari, San Jose, CA (US); Yeon S. Choi, Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/705,811

(22) Filed: Dec. 6, 2019

(65) Prior Publication Data

US 2020/0316249 A1 Oct. 8, 2020

Related U.S. Application Data

(63) Continuation of application No. 15/467,019, filed on Mar. 23, 2017, now Pat. No. 10,507,262, which is a continuation of application No. 14/722,829, filed on May 27, 2015, now Pat. No. 9,623,144, which is a continuation of application No. 14/273,408, filed on May 8, 2014, now Pat. No. 9,072,809, which is a continuation of application No. PCT/US2013/040619, filed on May 10, 2013.

(60) Provisional application No. 61/785,358, filed on Mar. 14, 2013, provisional application No. 61/669,577, filed on Jul. 9, 2012, provisional application No. 61/646,227, filed on May 11, 2012.

(51) Int. Cl.
| | | |
|---|---|---|
| *A61K 8/00* | (2006.01) |
| *A61L 26/00* | (2006.01) |
| *A61L 27/18* | (2006.01) |
| *A61L 27/52* | (2006.01) |
| *A61L 27/54* | (2006.01) |
| *A61L 24/00* | (2006.01) |
| *A61L 24/04* | (2006.01) |
| *A61L 27/58* | (2006.01) |
| *A61K 9/00* | (2006.01) |
| *A61K 47/18* | (2017.01) |
| *A61K 47/20* | (2006.01) |
| *A61K 47/32* | (2006.01) |
| *A61K 47/38* | (2006.01) |
| *A61K 9/70* | (2006.01) |
| *A61K 51/12* | (2006.01) |
| *A61F 9/007* | (2006.01) |

(52) U.S. Cl.
CPC ........ *A61L 26/0019* (2013.01); *A61K 9/0051* (2013.01); *A61K 9/7015* (2013.01); *A61K 47/18* (2013.01); *A61K 47/20* (2013.01); *A61K 47/32* (2013.01); *A61K 47/38* (2013.01); *A61L 24/0031* (2013.01); *A61L 24/0042* (2013.01); *A61L 24/046* (2013.01); *A61L 26/008* (2013.01); *A61L 26/009* (2013.01); *A61L 26/0023* (2013.01); *A61L 26/0066* (2013.01); *A61L 27/18* (2013.01); *A61L 27/52* (2013.01); *A61L 27/54* (2013.01); *A61L 27/58* (2013.01); *A61F 9/007* (2013.01); *A61F 9/00727* (2013.01); *A61K 51/1213* (2013.01); *A61L 2300/402* (2013.01); *A61L 2300/406* (2013.01); *A61L 2300/41* (2013.01); *A61L 2300/416* (2013.01); *A61L 2300/418* (2013.01); *A61L 2400/06* (2013.01); *A61L 2430/16* (2013.01); *C08J 2300/206* (2013.01)

(58) Field of Classification Search
CPC .. A61K 51/1213; A61F 9/007; A61F 9/00727
See application file for complete search history.

(56) References Cited

U.S. PATENT DOCUMENTS

| | | |
|---|---|---|
| 5,037,384 A | 8/1991 | Chang |
| 5,135,755 A | 8/1992 | Czech et al. |
| 5,336,175 A | 8/1994 | Mames |
| 5,858,345 A | 1/1999 | Charles et al. |
| 5,874,500 A | 2/1999 | Rhee et al. |
| 6,051,648 A | 4/2000 | Rhee et al. |
| 6,135,118 A | 10/2000 | Dailey |
| 6,149,931 A | 11/2000 | Schwartz et al. |
| 6,153,211 A | 11/2000 | Hubbell et al. |
| 6,180,687 B1 | 1/2001 | Hammer et al. |

(Continued)

FOREIGN PATENT DOCUMENTS

| | | |
|---|---|---|
| CA | 2750242 A1 | 8/2010 |
| JP | 2011-505420 A | 2/2011 |

(Continued)

OTHER PUBLICATIONS

3M Company. 3M.TM. Vetbond.TM. Veterinary Tissue Adhesive. Material Safety Data Sheet, Jun. 1, 2009.

Abbott Animal Health. GLUture.RTM., Information Brochure. Feb. 2009.

Bailico et al., MultiPEGS: high molecular weight multifunctional poly(ethylene glycol)s assembled by a denrimer-like approach, Eur J Org Chem 2005 2064-2073.

(Continued)

*Primary Examiner* — James W Rogers

(57) ABSTRACT

Provided herein are in vivo gelling ophthalmic pre-formulations forming a biocompatible retinal patch comprising at least one nucleophilic compound or monomer unit, at least one electrophilic compound or monomer unit, and optionally a therapeutic agent and/or viscosity enhancer. In some embodiments, the retinal patch at least partially adheres to the site of a retinal tear. Also provided herein are methods of treating retinal detachment by delivering an in vivo gelling ophthalmic pre-formulation to the site of a retinal tear in human eye, wherein the in vivo gelling ophthalmic pre-formulation forms a retinal patch.

22 Claims, 27 Drawing Sheets

(56) References Cited

U.S. PATENT DOCUMENTS

| | | | |
|---|---|---|---|
| 6,207,772 B1 | 3/2001 | Hatsuda et al. | |
| 6,312,725 B1 | 11/2001 | Wallace et al. | |
| 6,458,889 B1 | 10/2002 | Trollsas et al. | |
| 6,475,508 B1 | 11/2002 | Schwartz et al. | |
| 6,547,714 B1 | 4/2003 | Dailey | |
| 6,566,406 B1 | 5/2003 | Pathak et al. | |
| 6,605,294 B2 | 8/2003 | Sawhney | |
| 6,624,245 B2 | 9/2003 | Wallace et al. | |
| 6,632,457 B1 | 10/2003 | Sawhney | |
| 6,703,037 B1 | 3/2004 | Hubbell et al. | |
| 6,703,378 B1 | 3/2004 | Kunzler et al. | |
| 6,818,018 B1 | 11/2004 | Sawhney | |
| 7,009,343 B2 | 3/2006 | Lim et al. | |
| 7,255,874 B1 | 8/2007 | Bobo et al. | |
| 7,332,566 B2 | 2/2008 | Pathak et al. | |
| 7,553,810 B2 | 6/2009 | Gong et al. | |
| 7,592,418 B2 | 9/2009 | Pathak et al. | |
| 8,388,995 B1 | 3/2013 | Ali et al. | |
| 8,765,787 B2 | 7/2014 | Aberg et al. | |
| 8,987,339 B2 | 3/2015 | Askari et al. | |
| 9,072,809 B2 | 7/2015 | Askari et al. | |
| 9,149,560 B2 | 10/2015 | Askari et al. | |
| 9,623,144 B2 | 4/2017 | Askari et al. | |
| 10,111,985 B2 | 10/2018 | Askari et al. | |
| 10,189,773 B2 | 1/2019 | Askari et al. | |
| 10,227,289 B2 | 3/2019 | Askari et al. | |
| 2001/0003126 A1 | 6/2001 | Rhee et al. | |
| 2001/0055615 A1 | 12/2001 | Wallace et al. | |
| 2002/0042473 A1 | 4/2002 | Trollsas et al. | |
| 2002/0106409 A1 | 8/2002 | Sawhney et al. | |
| 2002/0114775 A1 | 8/2002 | Pathak | |
| 2002/0165337 A1 | 11/2002 | Wallace et al. | |
| 2003/0195113 A1 | 10/2003 | Nakamura et al. | |
| 2003/0223957 A1 | 12/2003 | Schwartz et al. | |
| 2004/0009205 A1 | 1/2004 | Sawhney | |
| 2004/0018228 A1 | 1/2004 | Fischell et al. | |
| 2004/0023842 A1 | 2/2004 | Pathak et al. | |
| 2004/0033264 A1 | 2/2004 | Sawhney | |
| 2004/0203149 A1 | 10/2004 | Childs et al. | |
| 2005/0027069 A1 | 2/2005 | Rhee et al. | |
| 2005/0191277 A1 | 9/2005 | Fisher | |
| 2005/0200295 A1 | 9/2005 | Lim et al. | |
| 2005/0203333 A1 | 9/2005 | Dailey et al. | |
| 2005/0208102 A1 | 9/2005 | Schultz | |
| 2005/0255039 A1 | 11/2005 | Desai | |
| 2005/0281802 A1 | 12/2005 | Gong et al. | |
| 2005/0281883 A1 | 12/2005 | Daniloff et al. | |
| 2006/0057208 A1 | 3/2006 | Holzer et al. | |
| 2006/0065199 A1 | 3/2006 | Davis | |
| 2006/0115457 A1 | 6/2006 | Hnojewyj | |
| 2006/0147409 A1 | 7/2006 | Pathak et al. | |
| 2006/0159771 A1 | 7/2006 | Kadrmas | |
| 2006/0222596 A1 | 10/2006 | Askari et al. | |
| 2007/0110813 A1 | 5/2007 | Ingenito et al. | |
| 2007/0280924 A1* | 12/2007 | Daniels | A61P 27/02 424/94.61 |
| 2008/0095736 A1 | 4/2008 | Pathak et al. | |
| 2008/0115787 A1 | 5/2008 | Ingenito | |
| 2008/0159975 A1 | 7/2008 | Nho et al. | |
| 2008/0160085 A1 | 7/2008 | Boland et al. | |
| 2008/0214695 A1 | 9/2008 | Pathak et al. | |
| 2008/0261884 A1 | 10/2008 | Tsai et al. | |
| 2008/0279944 A1 | 11/2008 | Sawhney | |
| 2008/0281352 A1 | 11/2008 | Ingenito et al. | |
| 2009/0087443 A1 | 4/2009 | Bartels | |
| 2009/0170811 A1 | 7/2009 | Garvey et al. | |
| 2009/0196928 A1 | 8/2009 | Hnojewyi | |
| 2009/0215923 A1 | 8/2009 | Carnahan et al. | |
| 2010/0040538 A1 | 2/2010 | Ingenito et al. | |
| 2010/0055078 A1 | 3/2010 | Hughes-Fulford | |
| 2010/0113476 A1 | 5/2010 | Chen et al. | |
| 2011/0081701 A1 | 4/2011 | Sargeant et al. | |
| 2011/0091551 A1 | 4/2011 | Baur | |
| 2012/0295869 A1 | 11/2012 | Liu et al. | |
| 2013/0108711 A1 | 5/2013 | Askari et al. | |
| 2013/0116341 A1 | 5/2013 | Askari et al. | |
| 2014/0248231 A1 | 9/2014 | Askari et al. | |
| 2014/0271528 A1 | 9/2014 | Askari et al. | |
| 2014/0271767 A1 | 9/2014 | Askari et al. | |
| 2014/0302051 A1 | 10/2014 | Askari et al. | |
| 2015/0190544 A1 | 7/2015 | Askari et al. | |
| 2015/0272987 A1 | 10/2015 | Askari et al. | |
| 2015/0273108 A1 | 10/2015 | Askari et al. | |

FOREIGN PATENT DOCUMENTS

| | | |
|---|---|---|
| JP | 2012812521 A | 4/2012 |
| WO | 9722371 A1 | 6/1997 |
| WO | 9903454 A1 | 1/1999 |
| WO | 0110416 A1 | 2/2001 |
| WO | 02053526 A1 | 7/2002 |
| WO | 2002/062276 A1 | 8/2002 |
| WO | 02102864 A1 | 12/2002 |
| WO | 2004021983 A2 | 3/2004 |
| WO | 2006030431 A2 | 3/2006 |
| WO | 2007016622 A2 | 2/2007 |
| WO | 2008141059 A2 | 11/2008 |
| WO | 2009/073192 A2 | 6/2009 |
| WO | 2009123768 A2 | 10/2009 |
| WO | 2009132153 A2 | 10/2009 |
| WO | 2010064251 A1 | 6/2010 |
| WO | 2010076400 A8 | 9/2010 |
| WO | 2011057131 A1 | 5/2011 |
| WO | 2011066291 A2 | 6/2011 |
| WO | 2011140517 A2 | 11/2011 |
| WO | 2011140519 A2 | 11/2011 |
| WO | 2012050591 A1 | 4/2012 |
| WO | 2012057628 A2 | 5/2012 |

OTHER PUBLICATIONS

Baino. Towards an ideal biomaterial for vitreous replacement: Historical overview and future trends. Acta Biomaterialia 7:921-935 (2011).
Brandi et al. Biodegradable hydrogels for time-controlled release of tethered peptides or proteins. Biomacromolecules 11:496-504 (2010).
Campbell et al. Evaluation of the PleuraSeal.TM. Lung Sealant System as a Thoracic Sealant in a Canine Lung Resection Model. Covidien (2007).
Co-pending U.S. Appl. No. 14/618,804, filed Feb. 10, 2015.
Co-pending U.S. Appl. No. 14/722,879, filed May 27, 2015.
Co-pending U.S. Appl. No. 14/739,917, filed Jun. 15, 2015.
Co-pending U.S. Appl. No. 14/947,818, filed Nov. 20, 2015.
Creative PEGWorks. Multiarm PEG materials. PEG product Catalog. last updated Dec. 31, 2012.
Dango et al. Initial experience with a synthetic sealant PleuraSeal. TM. after pulmonary resections: a prospective study with retrospective case matched controls. Journal of Cardiothoracic Surgery 5:50-58 (2010).
EP1317998.3 Search Report dated Feb. 13, 2014.
Ethicon, Inc. Ethicon.TM. Dermabond Advanced.TM. Instructions for Use. Status Mar. 2011.
Goudar, Review of pemetrexed in combination with cisplatin for the treatment of malignant pleural mesothelioma, Ther Clin Risk Manag 2008 4(1):205-211.
Jemyork Biotechnology. Multiarm PEG materials, web pages printed from www.jemyork.com/proshow.aspx?id=131 on Feb. 12, 2013.
JenKem Technology USA. Multi-arm PEG Derivatives, accessed Oct. 7, 2013 http://www.jenkemusa.com/Pages/MultiarmPEGs.aspx.
JenKem Technology USA. Multiarm PEG materials. PEG Products Catalog, 2011.
Lazzarin et al. Efficacy of Enfuvirtide in Patients Infected with Drug-Resistant HIV-1 in Europe and Australia. N. Engl. J. Med. 348(22):2186-2195 (2003).
Marcus et al. The skeletal Response to Teriparatide is Largely Independent of Age, Initial bone Mineral Density, and Prevalent Vertebral Fractures in Postmenopausal Women With Osteoporisis. J. Bone Miner. Res. 18:18-23 (2003).

(56) References Cited

OTHER PUBLICATIONS

NanoCS, Inc. Multiarm PEG Derivatives. web pages printed from http://www.nanocs.com/PEG/MAPEG.htm on Feb. 12, 2013.
Neer et al. Effect of Parathyroid Hormone (1-34) on Fractures and Bone Mineral Density in Postmenopausal Women with Osteoporosis. New Engl. J. Med. 344(19):1434 1441 (2001).
NeoMend, Inc. ProGEL.RTM., Instructions for Use and Product Labeling. Jan. 4, 2012.
Nicodemus et al., Cell encapsulation in biodegradable hydrogels for tissue engineering applications, Tissue Engineering Part B 2008 14(2):149-165.
NOF Corporation. Drug Delivery Systems. Catalogue Ver. 13. Prepared Oct. 2011.
Ostroha, PEG-based degradable networks for drug delivery applications, Thesis (165 pages), Jun. 2006.
PCT/US2011/035640 International Search Report and Written Opinion dated Jan. 19, 2012.
PCT/US2011/035643 International Search Report and Written Opinion dated Jan. 19, 2012.
PCT/US2013/040619 International Search Report dated Sep. 27, 2013.
PCT/US2014/028622 International Search Report dated Jul. 7, 2014.
PCT/US2014/028798 International Search Report dated Aug. 26, 2014.
Preul et al. Application of a new hydrogel dural sealant that reduces epidural adhesion formation: evaluation in a large animal laminectomy model. J Neurosurg Spine 12:381-390 (2010).
Sardari et al., Evaluation of clinical examination for differential diagnosis of lameness by navicular apparatus of heel pain in horses, Pakistan Journal of Biological Sciences 2008 11(13):1754-1756.
U.S. Appl. No. 13/571,116 Office Action dated Apr. 27, 2016.
U.S. Appl. No. 13/571,116 Office Action dated Mar. 4, 2015.
U.S. Appl. No. 13/571,116 Office Action dated Nov. 10, 2016.
U.S. Appl. No. 13/571,116 Office Action dated Oct. 22, 2015.
U.S. Appl. No. 13/696,028 Office Action dated Dec. 31, 2013.
U.S. Appl. No. 13/696,028 Office Action dated Jul. 17, 2015.
U.S. Appl. No. 13/696,028 Office Action dated Jun. 12, 2014.
U.S. Appl. No. 13/696,028 Office Action dated Nov. 7, 2014.
U.S. Appl. No. 13/696,028 Office Action dated Sep. 2, 2016.
U.S. Appl. No. 13/696,032 Office Action dated Dec. 10, 2014.
U.S. Appl. No. 13/696,032 Office Action dated Jan. 6, 2017.
U.S. Appl. No. 13/696,032 Office Action dated Jul. 17, 2015.
U.S. Appl. No. 13/696,032 Office Action dated Jun. 12, 2014.
U.S. Appl. No. 13/696,032 Office Action dated Jun. 8, 2016.
U.S. Appl. No. 13/696,032 Office Action dated Oct. 22, 2013.
U.S. Appl. No. 14/212,457 Office Action dated Jun. 9, 2014.
U.S. Appl. No. 14/213,520 Office Action dated Dec. 15, 2014.
U.S. Appl. No. 14/213,520 Office Action dated Jul. 3, 2014.
U.S. Appl. No. 14/273,408 Office Action dated Aug. 29, 2014.
U.S. Appl. No. 14/273,408 Office Action dated Nov. 18, 2014.
U.S. Appl. No. 14/273,408 Notice of Allowance dated Apr. 20, 2015.
U.S. Appl. No. 14/722,829 Office Action dated Aug. 18, 2015.
U.S. Appl. No. 14/722,829 Office Action dated Aug. 24, 2016.
U.S. Appl. No. 14/722,829 Office Action dated Feb. 5, 2016.
U.S. Appl. No. 14/739,917 Office Action dated Aug. 4, 2015.
U.S. Appl. No. 14/739,917 Office Action dated Jan. 22, 2016.
U.S. Appl. No. 14/739,917 Office Action dated May 11, 2016.
U.S. Appl. No. 14/739,917 Office Action dated Nov. 25, 2016.
U.S. Appl. No. 14/947,818 Office Action dated May 9, 2016.
U.S. Appl. No. 14/947,818 Office Action dated Nov. 23, 2016.
U.S. Appl. No. 14/947,818 Office Action dated Apr. 16, 2018.
U.S. Appl. No. 15/467,019 Office Action Final dated Nov. 23, 2018.
U.S. Appl. No. 15/479,519 Office Action dated Mar. 22, 2019.
U.S. Appl. No. 13/571,116 Notice of Allowance dated Jun. 19, 2018.
U.S. Appl. No. 13/696,028 Notice of Allowance dated Oct. 19, 2018.
U.S. Appl. No. 13/696,032 Notice of Allowance dated Sep. 6, 2018.
U.S. Appl. No. 14/722,829 Notice of Allowance dated Feb. 10, 2017.
U.S. Appl. No. 14/739,917 Office Action dated Aug. 2, 2018.
U.S. Appl. No. 14/739,917 Office Action dated Jun. 13, 2017.
U.S. Appl. No. 15/467,019, Nonfinal Office Action dated Mar. 8, 2018.
U.S. Appl. No. 15/467,019, Notice of Allowance dated Jul. 17, 2019.
U.S. Appl. No. 16/265,093, Nonfinal Office Action dated Dec. 9, 2019.

* cited by examiner (A)

(B)

(C)

(D)

(A)

(B)

(A)

(B)

(A)

(B)

(A)

(B)

Mixing Assembly

Final mixture ready for injection

BIOCOMPATIBLE HYDROGEL TREATMENTS FOR RETINAL DETACHMENT

CROSS-REFERENCE

This application is a continuation of U.S. patent application Ser. No. 14/722,829, filed May 27, 2015, which is a continuation of U.S. patent application Ser. No. 14/273,408, filed May 8, 2014, now U.S. Pat. No. 9,072,809, issued Jul. 7, 2015, which was filed pursuant to 35 U.S.C. § 111(a) as a continuation of PCT International Application No. PCT/US2013/040619, filed May 10, 2013, which claims the benefit of U.S. Provisional Application No. 61/646,227, filed May 11, 2012, U.S. Provisional Application No. 61/669,577, filed Jul. 9, 2012, and U.S. Provisional Application No. 61/785,358, filed Mar. 14, 2013, each of which are incorporated herein by reference in their entireties.

BACKGROUND OF THE INVENTION

Retinal detachment is a disorder of the eye in which the retina peels away from its underlying layer of support tissue. When the retina becomes detached, bleeding from area blood vessels may cloud the inside of the eye, which is normally filled with vitreous fluid. Central vision becomes severely affected if the macula, the part of the retina responsible for fine vision, becomes detached. The most common types of retinal detachments are often due to a tear or hole in the retina. Eye fluids may leak through this opening. This causes the retina to separate from the underlying tissues, much like a bubble under wallpaper. This is most often caused by a condition called posterior vitreous detachment. Another type of retinal detachment is called tractional detachment. This is seen in people who have uncontrolled diabetes, previous retinal surgery, or have chronic inflammation. If not treated in time, it results in blindness. Initial detachment may be localized, but without rapid treatment the entire retina may detach, leading to vision loss and blindness.

Most people with a retinal detachment will need surgery. Surgery may be done immediately or after a short period of time.

SUMMARY OF THE INVENTION

Provided herein is a in vivo gelling ophthalmic pre-formulation, comprising: (a) at least one first compound comprising more than one nucleophilic group; (b) at least one second compound comprising more than one electrophilic group; (c) an aqueous buffer in the pH range of about 6.0 to about 8.5; and (d) a viscosity enhancer; wherein the in vivo gelling ophthalmic formulation at least in part polymerizes and/or gels at a target site of an eye to form a biocompatible retinal patch. In some embodiments, the target site is a retinal tear. In certain embodiments, the biocompatible retinal patch at least partially adheres to the target site. In some embodiments, the in vivo gelling ophthalmic pre-formulation further comprises a therapeutic agent. In some embodiments, the viscosity enhancer is selected from hydroxyethylcellulose, hydroxypropylmethylcellulose, methylcellulose, polyvinyl alcohol, or polyvinylpyrrolidone.

In certain embodiments of the in vivo gelling ophthalmic pre-formulation, the nucleophilic group is a thiol or amino group. In some embodiments, the first compound is a glycol, trimethylolpropane, pentaerythritol, hexaglycerol, or tripentaerythritol derivative. In certain embodiments, the first compound further comprises one or more polyethylene glycol sections. In some embodiments, the first compound is a pentaerythritol or hexaglycerol derivative. In certain embodiments, the first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, and ethoxylated hexaglycerol amino acetate. In certain embodiments, the first compound is selected from the group consisting of trimethylolpropane trimercaptoacetate, trimethylolpropane tri-3-mercaptopropionate, pentaerythritol tetramercaptoacetate, pentaerythritol tetra-3-mercaptopropionate, ethoxylated trimethylolpropane trimercaptoacetate, ethoxylated trimethylolpropane tri-3-mercaptopropionate, ethoxylated pentaerythritol tetramercaptoacetate, and ethoxylated trimethylolpropane tri-3-mercaptopropionate. In some embodiments, the molecular weight of the first compound is between about 100 and 100000. In certain embodiments, the first compound is water soluble. In some embodiments, the electrophilic group is an epoxide, N-succinimidyl succinate, N-succinimidyl glutarate, N-succinimidyl succinamide or N-succinimidyl glutaramide.

In certain embodiments of the in vivo gelling ophthalmic pre-formulation, the second compound is a trimethylolpropane, glycerol, diglycerol, pentaerythritol, sorbitol, hexaglycerol, tripentaerythritol, or polyglycerol derivative. In some embodiments, the second compound further comprises one or more polyethylene glycol sections. In certain embodiments, the second compound is a trimethylolpropane, pentaerythritol, or hexaglycerol derivative. In some embodiments, the second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, and ethoxylated hexaglycerol succinimidyl glutaramide. In certain embodiments, the second compound is selected from the group consisting of sorbitol polyglycidyl ether, polyglycerol polyglycidyl ether, diglycerol polyglycidyl ether, glycerol polyglycidyl ether, and trimethylolpropane polyglycidyl ether. In some embodiments, the molecular weight of the second compound is between about 100 and 100000. In certain embodiments, the second compound is water soluble.

In some embodiments of the in vivo gelling ophthalmic pre-formulation, the gelling time of the biocompatible retinal patch is controlled by the pH of the aqueous buffer, the type of the buffer, the concentration of the buffer, the concentration of the first compound and/or the second compound in the buffer, or the nature of the electrophilic groups. In certain embodiments, the gelling time is between about 20 seconds and 10 minutes. In some embodiments, the pH of the aqueous buffer is from about 8. In certain embodiments, the in vivo gelling ophthalmic pre-formulation gels at a predetermined time to form the biocompatible retinal patch. In some embodiments, the biocompatible retinal patch is a bioabsorbable polymer. In certain embodiments, the biocompatible retinal patch is bioabsorbed within about 1 to 70 days. In some embodiments, the biocompatible retinal patch is substantially non-bioabsorbable.

In certain embodiments of the in vivo gelling ophthalmic pre-formulation, the therapeutic agent is released from the biocompatible retinal patch through diffusion, osmosis, degradation of the biocompatible retinal patch, or any combination thereof. In some embodiments, the therapeutic agent is initially released from the biocompatible retinal patch through diffusion and later released through degradation of the biocompatible retinal patch. In certain embodiments, the therapeutic agent is substantially released from the biocompatible retinal patch within 180 days. In some embodiments, the therapeutic agent is substantially released from the biocompatible retinal patch within 14 days. In certain embodiments, the therapeutic agent is substantially released from the biocompatible retinal patch within 24 hours. In some embodiments, the therapeutic agent is substantially released from the biocompatible retinal patch within one hour. In certain embodiments, the first compound and the second compound do not react with the therapeutic agent during formation of the biocompatible retinal patch. In some embodiments, the biocompatible retinal patch interacts with the therapeutic agent, and wherein more than 10% of the therapeutic agent is released through degradation of the biocompatible retinal patch. In certain embodiments, more than 30% of the therapeutic agent is released through degradation of the biocompatible retinal patch. In some embodiments, the biocompatible retinal patch interacts with the therapeutic agent by forming covalent bonds between the biocompatible retinal patch and the therapeutic agent. In certain embodiments, the biocompatible retinal patch interacts with the therapeutic agent by forming a non-covalent bond between the biocompatible retinal patch and the therapeutic agent. In some embodiments, the therapeutic agent is released while the biocompatible retinal patch degrades. In certain embodiments, the release of the therapeutic agent is essentially inhibited until a time that the biocompatible retinal patch starts to degrade. In some embodiments, the time the biocompatible retinal patch starts to degrade is longer the higher a degree of cross-linking of the biocompatible retinal patch. In certain embodiments, the time the biocompatible retinal patch starts to degrade is shorter the higher a concentration of ester groups in the first or second compound.

Also provided herein is a biocompatible retinal patch made by mixing: (a) at least one first compound comprising more than one nucleophilic group; (b) at least one second compound comprising more than one electrophilic group; (c) an aqueous buffer in the pH range of about 6.0 to about 8.5; (d) a viscosity enhancer; and (e) optionally a therapeutic agent; wherein the mixing is performed outside external to a human eye, and the biocompatible retinal patch gels at least in part at a target site inside the human eye.

In some embodiments of the biocompatible retinal patch, the viscosity enhancer is selected from hydroxyethylcellulose, hydroxypropylmethylcellulose, methylcellulose, polyvinyl alcohol, or polyvinylpyrrolidone.

In certain embodiments of the biocompatible retinal patch, the target site is a retinal tear. In some embodiments, the biocompatible retinal patch at least partially adheres to the target site.

In certain embodiments of the biocompatible retinal patch, the nucleophilic group is a thiol or amino group. In some embodiments, the first compound is a glycol, trimethylolpropane, pentaerythritol, hexaglycerol, or tripentaerythritol derivative. In certain embodiments, the first compound further comprises one or more polyethylene glycol sections. In some embodiments, the first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, ethoxylated trimethylolpropane tri-3-mercaptopropionate, ethoxylated hexaglycerol amino acetate.

In some embodiments of the biocompatible retinal patch, the electrophilic group is an epoxide, N-succinimidyl succinate, N-succinimidyl glutarate, N-succinimidyl succinamide, or N-succinimidyl glutaramide. In certain embodiments, the second compound is a trimethylolpropane, glycerol, diglycerol, pentaerythritol, sorbitol, hexaglycerol, tripentaerythritol, or polyglycerol derivative. In some embodiments, the second compound further comprises one or more polyethylene glycol sections. In certain embodiments, the second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, ethoxylated hexaglycerol succinimidyl glutaramide, and sorbitol polyglycidyl ether.

In certain embodiments of the biocompatible retinal patch, the molecular weight of the first compound and the second compound is between about 100 and 100000. In some embodiments, the first compound is waters soluble. In certain embodiments, the second compound is water soluble.

In some embodiments of the biocompatible retinal patch, the gelling time of the biocompatible retinal patch is controlled by the pH of the aqueous buffer, the type of the buffer, the concentration of the buffer, the concentration of the first compound and/or the second compound in the buffer, or the nature of the electrophilic groups. In certain embodiments, the gelling time is between about 20 seconds and 10 minutes. In some embodiments, the biocompatible retinal patch gels at a predetermined time.

In certain embodiments of the biocompatible retinal patch, the biocompatible retinal patch is a bioabsorbable polymer. In some embodiments, the biocompatible retinal patch is bioabsorbed within about 1 to 70 days. In certain embodiments, the biocompatible retinal patch is substantially non-bioabsorbable.

In some embodiments of the biocompatible retinal patch, the biocompatible retinal patch further comprises a radiopaque material or a pharmaceutically acceptable dye.

In certain embodiments of the biocompatible retinal patch, the therapeutic agent is released from the biocompatible retinal patch through diffusion, osmosis, degradation of the biocompatible retinal patch, or any combination thereof. In some embodiments, the therapeutic agent is initially released from the biocompatible retinal patch through diffusion and later released through degradation of the biocompatible retinal patch. In certain embodiments, the therapeutic agent is substantially released from the biocompatible retinal patch within 180 days. In some embodiments, the therapeutic agent is substantially released from the biocompatible retinal patch within 24 hours.

In certain embodiments of the biocompatible retinal patch, the first compound and the second compound do not react with the therapeutic agent during formation of the biocompatible retinal patch. In some embodiments, the biocompatible retinal patch interacts with the therapeutic agent, and wherein more than 10% of the therapeutic agent is released through degradation of the biocompatible retinal patch. In certain embodiments, the release of the therapeutic agent is determined by the composition of the biocompatible retinal patch. In some embodiments, the therapeutic agent is released while the biocompatible retinal patch degrades. In certain embodiments, the release of the therapeutic agent is essentially inhibited until a time that the biocompatible retinal patch starts to degrade. In some embodiments, at least a portion of the therapeutic agent is released before the time that the biocompatible retinal patch starts to degrade. In certain embodiments, the time the biocompatible retinal patch starts to degrade is longer the higher a degree of cross-linking of the biocompatible retinal patch. In some embodiments, the time the biocompatible retinal patch starts to degrade is shorter the higher a concentration of ester groups in the first or second compound.

Further provided here in a in vivo polymerized biocompatible retinal patch comprising: (a) at least one first monomeric unit bound through at least one amide, thioester, or thioether linkage to at least one second monomeric unit; (b) at least one second monomeric unit bound to at least one first monomeric unit; (c) a viscosity enhancer; and (d) optionally a therapeutic agent; wherein the in vivo polymerized biocompatible retinal patch is polymerized at least in part at a retinal tear in a human eye. In some embodiments, the in vivo polymerized biocompatible patch at least partially adheres to the retina of the eye. In certain embodiments, the viscosity enhancer is selected from hydroxyethylcellulose, hydroxypropylmethylcellulose, methylcellulose, polyvinyl alcohol, or polyvinylpyrrolidone.

In some embodiments of the in vivo polymerized biocompatible retinal patch, the first monomeric unit is a glycol, trimethylolpropane, pentaerythritol, hexaglycerol, or tripentaerythritol derivative. In certain embodiments, the first monomeric unit further comprises one or more polyethylene glycol sections. In some embodiments, the second monomeric unit is a trimethylolpropane, glycerol, diglycerol, pentaerythritol, sorbitol, hexaglycerol, tripentaerythritol, or polyglycerol derivative. In certain embodiments, the second monomeric unit comprises one or more polyethylene glycol sections. In some embodiments, the molecular weight of the first monomeric unit and the second monomeric unit is between about 100 and 100000.

In certain embodiments of the in vivo polymerized biocompatible retinal patch, the in vivo polymerized biocompatible retinal patch is a bioabsorbable polymer. In some embodiments, the in vivo polymerized biocompatible retinal patch is bioabsorbed within about 1 to 70 days. In certain embodiments, the in vivo polymerized biocompatible retinal patch is substantially non-bioabsorbable.

In some embodiments of the in vivo polymerized biocompatible retinal patch, the in vivo polymerized biocompatible retinal patch further comprises a radiopaque material or a pharmaceutically acceptable dye.

In certain embodiments of the in vivo polymerized biocompatible retinal patch, the therapeutic agent is released from the in vivo polymerized biocompatible retinal patch through diffusion, osmosis, degradation of the in vivo polymerized biocompatible retinal patch, or any combination thereof. In certain embodiments, the therapeutic agent is initially released from the in vivo polymerized biocompatible retinal patch through diffusion and later released through degradation of the in vivo polymerized biocompatible retinal patch. In some embodiments, the therapeutic agent is substantially released from the vivo polymerized biocompatible retinal patch within 180 days. In certain embodiments, the therapeutic agent is substantially released from the vivo polymerized biocompatible retinal patch within 24 hours. In some embodiments, the release of the therapeutic agent is determined by the composition of the in vivo polymerized biocompatible retinal patch. In certain embodiments, the therapeutic agent is released while the in vivo polymerized biocompatible retinal patch degrades. In some embodiments, the release of the therapeutic agent is essentially inhibited until a time that the in vivo polymerized biocompatible retinal patch starts to degrade. In certain embodiments, at least a portion of the therapeutic agent is released before the time that the in vivo polymerized biocompatible retinal patch starts to degrade. In some embodiments, the time the in vivo polymerized biocompatible retinal patch starts to degrade is longer the higher a degree of cross-linking of the in vivo polymerized biocompatible retinal patch. In certain embodiments, the time the in vivo polymerized biocompatible retinal patch starts to degrade is shorter the higher a concentration of ester groups in the first or second compound.

Also provided herein is a method of treating retinal detachment, a retinal tear, or a retinal hole, comprising delivering an in vivo gelling ophthalmic pre-formulation to a site of a retinal tear in a human eye, the in vivo gelling ophthalmic pre-formulation comprising: (a) at least one first compound comprising more than one nucleophilic group; (b) at least one second compound comprising more than one electrophilic group; (c) an aqueous buffer in the pH range of about 6.0 to about 8.5; and (d) a viscosity enhancer; wherein the in vivo gelling ophthalmic formulation at least in part polymerizes and/or gels at the site of the retinal tear in the human eye to form a biocompatible retinal patch. In some embodiments, the biocompatible retinal patch at least partially adheres to the site of the retinal tear. In certain embodiments, the biocompatible retinal patch closes the site of a retinal tear.

In some embodiments of the method, the in vivo gelling ophthalmic pre-formulation further comprises a therapeutic agent. In certain embodiments, the viscosity enhancer is selected from hydroxyethylcellulose, hydroxypropylmethylcellulose, methylcellulose, polyvinyl alcohol, or polyvinylpyrrolidone.

In certain embodiments of the method, the nucleophilic group is a thiol or amino group. In some embodiments, the first compound is a glycol, trimethylolpropane, pentaerythritol, hexaglycerol, or tripentaerythritol derivative. In certain embodiments, the first compound further comprises one or more polyethylene glycol sections. In some embodiments, the first compound is a pentaerythritol or hexaglycerol derivative. In certain embodiments, the first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, and ethoxylated hexaglycerol amino acetate. In some embodiments, the first compound is selected from the group consisting of trimethylolpropane trimercaptoacetate, trimethylolpropane tri-3-mercaptopropionate, pentaerythritol tetramercaptoacetate, pentaerythritol tetra-3-mercaptopropionate, ethoxylated trimethylolpropane trimercaptoacetate, ethoxylated trimethylolpropane tri-3-mercaptopropionate, ethoxylated pentaerythritol tetramercaptoacetate, and ethoxylated trimethylolpropane tri-3-mercaptopropionate. In certain embodiments, the molecular weight of the first compound is between about 100 and 100000. In some embodiments, the first compound is water soluble.

In some embodiments of the method, the electrophilic group is an epoxide, N-succinimidyl succinate, N-succinimidyl glutarate, N-succinimidyl succinamide or N-succinimidyl glutaramide. In certain embodiments, the second compound is a trimethylolpropane, glycerol, diglycerol, pentaerythritol, sorbitol, hexaglycerol, tripentaerythritol, or polyglycerol derivative. In some embodiments, the second compound further comprises one or more polyethylene glycol sections. In certain embodiments, the second compound is a trimethylolpropane, pentaerythritol, or hexaglycerol derivative. In some embodiments, the second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, and ethoxylated hexaglycerol succinimidyl glutaramide. In certain embodiment, the second compound is selected from the group consisting of sorbitol polyglycidyl ether, polyglycerol polyglycidyl ether, diglycerol polyglycidyl ether, glycerol polyglycidyl ether, and trimethylolpropane polyglycidyl ether. In some embodiments, the molecular weight of the second compound is between about 10000 and 100000. In certain embodiments, the second compound is water soluble.

In certain embodiments of the method, the gelling time of the biocompatible retinal patch is controlled by the pH of the aqueous buffer, the type of the buffer, the concentration of the buffer, the concentration of the first compound and/or the second compound in the buffer, or the nature of the electrophilic groups. In some embodiments, the gelling time is between about 20 seconds and 10 minutes. In certain embodiments, the pH of the aqueous buffer is from about 8. In some embodiments, the in vivo gelling ophthalmic preformulation gels at a predetermined time to form the biocompatible retinal patch.

In some embodiments of the method, the biocompatible retinal patch is a bioabsorbable polymer. In certain embodiments of the method, the biocompatible retinal patch is bioabsorbed within about 1 to 70 days. In some embodiments of the method, the biocompatible retinal patch is substantially non-bioabsorbable.

In certain embodiments of the method, the therapeutic agent is released from the biocompatible retinal patch through diffusion, osmosis, degradation of the biocompatible retinal patch, or any combination thereof. In some embodiments, the therapeutic agent is initially released from the biocompatible retinal patch through diffusion and later released through degradation of the biocompatible retinal patch. In certain embodiments, the therapeutic agent is substantially released from the biocompatible retinal patch within 180 days. In some embodiments, the therapeutic agent is substantially released from the biocompatible retinal patch within 14 days. In certain embodiments, the therapeutic agent is substantially released from the biocompatible retinal patch within 24 hours. In some embodiments, the therapeutic agent is substantially released from the biocompatible retinal patch within one hour. In certain embodiments, the first compound and the second compound do not react with the therapeutic agent during formation of the biocompatible retinal patch. In some embodiments, the biocompatible retinal patch interacts with the therapeutic agent, and more than 10% of the therapeutic agent is released through degradation of the biocompatible retinal patch. In certain embodiments, more than 30% of the therapeutic agent is released through degradation of the biocompatible retinal patch. In some embodiments, the biocompatible retinal patch interacts with the therapeutic agent by forming covalent bonds between the biocompatible retinal patch and the therapeutic agent. In certain embodiments, the biocompatible retinal patch interacts with the therapeutic agent by forming a non-covalent bond between the biocompatible retinal patch and the therapeutic agent. In some embodiments, the therapeutic agent is released while the biocompatible retinal patch degrades. In certain embodiments, the release of the therapeutic agent is essentially inhibited until a time that the biocompatible retinal patch starts to degrade. In some embodiments, the time the biocompatible retinal patch starts to degrade is longer the higher a degree of cross-linking of the biocompatible retinal patch. In certain embodiments, the time the biocompatible retinal patch starts to degrade is shorter the higher a concentration of ester groups in the first or second compound.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
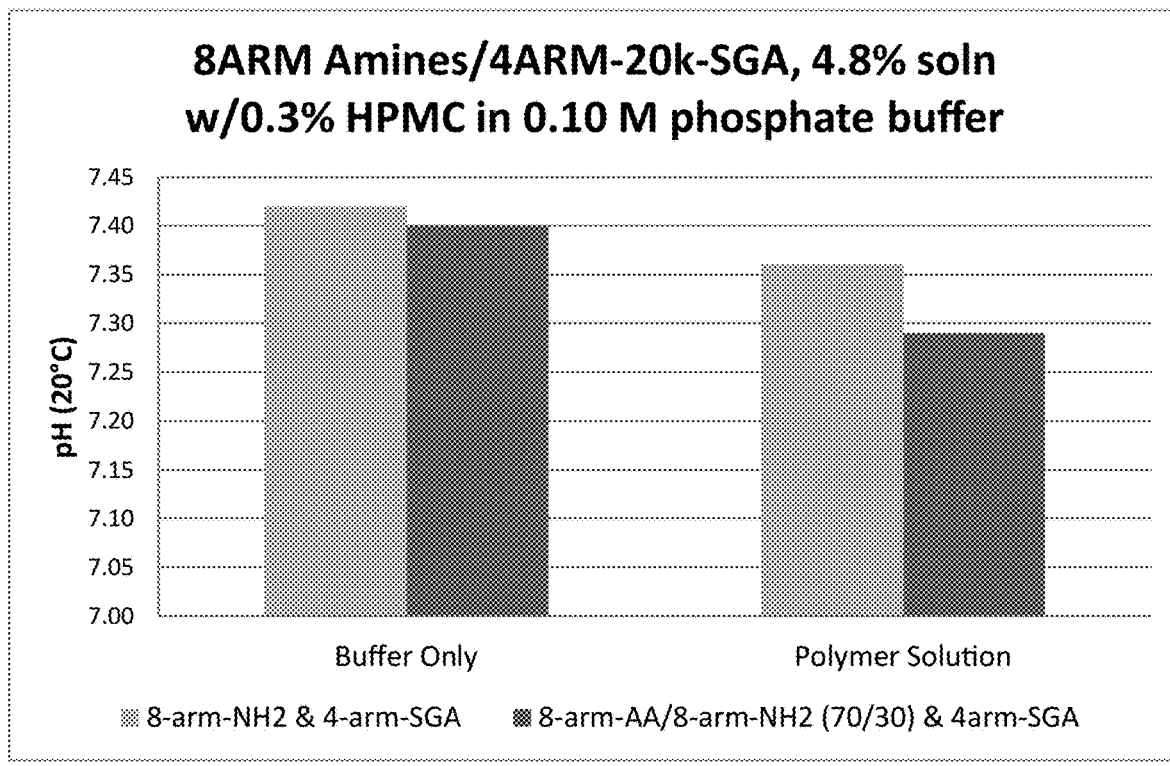
FIG. 1 shows the effect of pH on monomer addition to the 0.10 M phosphate reaction buffer for two formulations: 1) 8ARM-20k-NH2 & 4ARM-20k-SGA at 4.8% solution with 0.3% HPMC; 2) 8ARM-20k-AA/8ARM-20k-NH2 (70/30) & 4ARM-20k-SGA at 4.8% solution with 0.3% HPMC.

The current method for treating retinal detachment involves surgery followed by suturing or laser treatment followed by filling the eye interior with an inert gas or silicon oil. The post operation results in the intraocular pressure inside and there is no vision for 2-4 weeks. If filled with the inert gas, the travel is also not possible during this period due to the possible change in the atmospheric pressure at the new location. However, if the cavity is filled with silicone oil, then another surgery is required to remove the silicon oil after the healing process is complete. In addition, the current retinal patches are difficult to make stay in place while the current commercially available adhesives do not bond well to the retina and are difficult to deliver to the site.

Therefore, herein is provided a family of in vivo gelling biocompatible ophthalmic pre-formulations that can be injected at or near the affected area using a narrow bore needles and that form biocompatible retinal patches. Once the target location has been identified inside the eye, an exact volume of the reacting mixture is injected inside. Once on site, the liquid wets the surface of the retina and fills the hole. After a preset time, the liquid turns into a solid and bonds the two layers together and attaches the retina and also fills the hole forming a retinal patch. The viscosity of the formulations is controlled such that the liquid remains localized at the target site. In some embodiments, the in vivo gelling biocompatible ophthalmic pre-formulation also adheres to the site in the eye. In certain embodiment, the viscosity and stickiness of the in vivo gelling ophthalmic pre-formulation is suitable for easy delivery to the site through a narrow bore needle, while at the same time staying in place at the site of the retinal tear and adhering to the tissue surrounding the retinal tear. In some embodiments, the in vivo gelling ophthalmic pre-formulations comprise viscosity enhancers to ensure that the pre-formulation remains at and/or adheres to the target site in the eye during the gelling process. The physicochemical properties of the biopolymer are matched with the surrounding tissues and the retina, so that there is little change in pressure from the natural atmosphere.

In further embodiments, an in vivo gelling ophthalmic pre-formulation to form a biocompatible retinal patch enables the administration of medication directly to the vitreous. The polymer starts out as a liquid pre-formulation and is delivered, together with one or more optional therapeutic agents, to the site of a disease using minimally invasive techniques. Once in the eye, the liquid pre-formulation polymerizes into a solid hydrogel that in some instances adheres to the tissue and keeps the polymer/drug combination at the site of the disease. In some instances, polymerization and degradation times are controlled by varying the composition of the monomers and buffers allowing for the appropriate application and placement of the hydrogel polymer. In some embodiments, the drug is released in a precise and consistent manner. In certain instances, the biocompatible hydrogel polymer is bioabsorbed over a defined period of time. In some embodiments, the biocompatible hydrogel polymer provides the sustained release of a therapeutic agent at a target site. In certain embodiments, the sustained and controlled release reduces the systemic exposure to the therapeutic agent. The controlled gelling and biodegradation allows the use of the biocompatible hydrogel polymer to deliver one or more therapeutic agents directly to the tissue affected by a disease, thereby minimizing systemic exposure to the therapeutic agent.

In some instances, the therapeutic agent is released from the biocompatible hydrogel polymer over an extended period of time. In certain instances, delivery of the therapeutic agent in a biocompatible hydrogel polymer provides a depot of the therapeutic agent (e.g., under the skin), wherein the depot releases the therapeutic agent over an extended period of time (e.g., 1 day, 2 days, 3 days, 4 days, 5 days, 6 days, 7 days, 10, days, 14 days, 3 week, 4 week). In some instances, the biocompatible hydrogel polymer releases the therapeutic agent after a delay as a delayed burst.

In some embodiments, an in vivo gelling ophthalmic pre-formulation completely replaces the vitreous humour of an eye. In certain embodiments, the in vivo gelling ophthalmic pre-formulation partially replaces the vitreous humour of an eye.

The in vivo gelling ophthalmic pre-formulations are useful to treat retinal detachment and other conditions of the eye. Delivering an in vivo gelling ophthalmic pre-formulation to the site of a retinal tear in an eye, the pre-formulation at least in part polymerizes and/or gels at the site of the retinal tear in the eye and forms a retinal patch. The retinal patch at least partially adheres to the retinal tear and closes the hole treating the retinal detachment and allowing it to heal.

Furthermore, the in vivo gelling ophthalmic pre-formulations are useful to deliver therapeutic agents to the inside of the eye to treat conditions of the eye, for example age-related macular degeneration, diabetic retinopathy, cataract, intra-ocular pressure (glaucoma), or proliferative vitreoretinopathy.

Exemplary Hydrogel Components

Provided herein are in vivo gelling ophthalmic pre-formulations, comprising at least one first compound comprising more than one nucleophilic group, at least one second compound comprising more than one electrophilic group, an aqueous buffer in the pH range of about 5.0 to about 9.5, and optionally one or more therapeutic agents. In certain embodiments, the in vivo gelling ophthalmic pre-formulation forms a biocompatible hydrogel polymer at a target site in a human body by mixing the at least one first compound, the at least one second compound, and the optional therapeutic agent in the aqueous buffer and delivering the mixture to the target site such that the biocompatible hydrogel polymer at least in part polymerizes and/or gels at the target site. In some embodiments, the biocompatible hydrogel polymer is formed following mixing the first compound and the second compound in the aqueous buffer; and wherein the biocompatible hydrogel polymer gels at a target site. In certain embodiments, mixing the first compound, the second compound, and the optional therapeutic agent in the aqueous buffer and delivering the mixture to a target site in the human body generates the in vivo gelling ophthalmic pre-formulation such that the in vivo gelling ophthalmic pre-formulation at least in part polymerizes and/or gels at the target site to form a biocompatible hydrogel polymer.

In some embodiments, the first or second compound comprising more than one nucleophilic or electrophilic group are polyol derivatives. In certain embodiments, the first or second compound is a dendritic polyol derivative. In some embodiments, the first or second compound is a glycol, trimethylolpropane, glycerol, diglycerol, pentaerythritiol, sorbitol, hexaglycerol, tripentaerythritol, or polyglycerol derivative. In certain embodiments, the first or second compound is a glycol, trimethylolpropane, pentaerythritol, hexaglycerol, or tripentaerythritol derivative. In some embodiments, the first or second compound is a trimethylolpropane, glycerol, diglycerol, pentaerythritiol, sorbitol, hexaglycerol, tripentaerythritol, or polyglycerol derivative. In some embodiments, the first or second compound is a pentaerythritol, di-pentaerythritol, or tripentaerythritol derivative. In certain embodiments, the first or second compound is a hexaglycerol (2-ethyl-2-(hydroxymethyl)-1, 3-propanediol, trimethylolpropane) derivative. In some embodiments, the first or second compound is a sorbitol derivative. In certain embodiments, the first or second compound is a glycol, propyleneglycol, glycerin, diglycerin, or polyglycerin derivative.

In some embodiments, the first and/or second compound further comprises polyethylene glycol (PEG) chains comprising one to 200 ethylene glycol subunits. In certain embodiments, the first and/or second compound further comprises polypropylene glycol (PPG) chains comprising one to 200 propylene glycol subunits. The PEG or PPG chains extending from the polyols are the "arms" linking the polyol core to the nucleophilic or electrophilic groups.

Exemplary Nucleophilic Monomers

The in vivo gelling ophthalmic pre-formulation comprises at least one first compound comprising more than one nucleophilic group. In some embodiments, the nucleophilic group is a hydroxyl, thiol, or amino group. In preferred embodiments, the nucleophilic group is a thiol or amino group.

In certain embodiments, the nucleophilic group is connected to the polyol derivative through a suitable linker. Suitable linkers include, but are not limited to, esters (e.g., acetates) or ethers. In some instances, monomers comprising ester linkers are more susceptible to biodegradation. Examples of linkers comprising a nucleophilic group include, but are not limited to, mercaptoacetate, aminoacetate (glycin) and other amino acid esters (e.g., alanine, β-alanine, lysine, ornithine), 3-mercaptopropionate, ethylamine ether, or propylamine ether. In some embodiments, the polyol core derivative is bound to a polyethylene glycol or polypropylene glycol subunit, which is connected to the linker comprising the nucleophilic group. The molecular weight of the first compound (the nucleophilic monomer) is about 100 to 100000. In certain embodiments, the molecular weight of a first compound (a nucleophilic monomer) is about 100, about 500, about 1000, about 2000, about 3000, about 4000, about 5000, about 6000, about 7000, about 8000, about 9000, about 10000, about 12000, about 15000, about 20000, about 25000, about 30000, about 35000, about 40000, about 50000, about 60000, about 70000, about 80000, about 90000, or about 100000. In certain embodiments, the molecular weight of a second compound is about 500 to 40000. In some embodiments, the molecular weight of a first compound is about 500 to 2000. In certain embodiments, the molecular weight of a first compound is about 15000 to about 40000. In some embodiments, the first compound is water soluble.

Examples of the construction of monomers comprising more than one nucleophilic group are shown below with a trimethylolpropane or pentaerythritol core polyol. The compounds shown have thiol or amine electrophilic groups that are connected to variable lengths PEG subunit through acetate, propionate or ethyl ether linkers (e.g., structures below of ETTMP (A; n=1), 4ARM-PEG-NH2 (B; n=1), and 4ARM-PEG-AA (C; n=1)). Monomers using other polyol cores are constructed in a similar way.

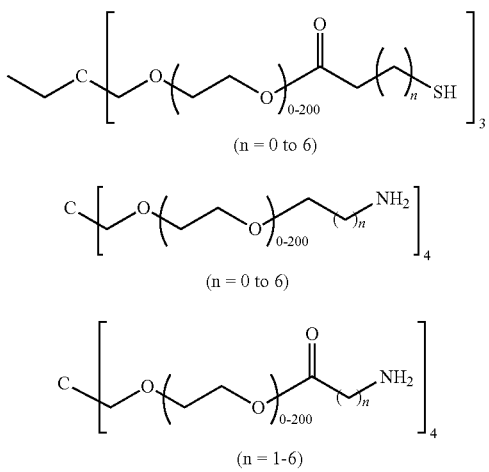

A (n = 0 to 6)

B (n = 0 to 6)

C (n = 1-6)

Suitable first compounds comprising a nucleophilic group (used in the amine-ester chemistry) include, but are not limited to, pentaerythritol polyethylene glycol amine (4ARM-PEG-NH2) (molecular weight selected from about 5000 to about 40000, e.g., 5000, 10000, or 20000), pentaerythritol polyethylene glycol amino acetate (4ARM-PEG-AA) (molecular weight selected from about 5000 to about 40000, e.g., 5000, 10000, or 20000), hexaglycerin polyethylene glycol amine (8ARM-PEG-NH2) (molecular weight selected from about 5000 to about 40000, e.g., 10000, 20000, or 40000), or tripentaerythritol glycol amine (8ARM(TP)-PEG-NH2) (molecular weight selected from about 5000 to about 40000, e.g., 10000, 20000, or 40000). Within this class of compounds, 4(or 8)ARM-PEG-AA comprises ester (or acetate) groups while the 4(or 8)ARM-PEG-NH2 monomers do not comprise ester (or acetate) groups.

Other suitable first compounds comprising a nucleophilic group (used in the thiol-ester chemistry) include, but not limited to, glycol dimercaptoacetate (THIOCURE® GDMA), trimethylolpropane trimercaptoacetate (THIOCURE® TMPMA), pentaerythritol tetramercaptoacetate (THIOCURE® PETMA), glycol di-3-mercaptopropionate (THIOCURE® GDMP), trimethylolpropane tri-3-mercaptopropionate (THIOCURE® TMPMP), pentaerythritol tetra-3-mercaptopropionate (THIOCURE® PETMP), polyol-3-mercaptopropionates, polyester-3-mercaptopropionates, propyleneglycol 3-mercaptopropionate (THIOCURE® PPGMP 800), propyleneglycol 3-mercaptopropionate (THIOCURE® PPGMP 2200), ethoxylated trimethylolpropane tri-3-mercaptopropionate (THIOCURE® ETTMP-700), and ethoxylated trimethylolpropane tri-3-mercaptopropionate (THIOCURE® ETTMP-1300).

Exemplary Electrophilic Monomers

The in vivo gelling ophthalmic pre-formulation comprises at least one first compound comprising more than one electrophilic group. In some embodiments, the electrophilic group is an epoxide, maleimide, succinimidyl, or an alpha-beta unsaturated ester. In preferred embodiments, the electrophilic group is an epoxide or succinimidyl.

In certain embodiments, the electrophilic group is connected to the polyol derivative through a suitable linker. Suitable linkers include, but are not limited to, esters, amides, or ethers. In some instances, monomers comprising ester linkers are more susceptible to biodegradation. Examples of linkers comprising an electrophilic group include, but are not limited to, succinimidyl succinate, succinimidyl glutarate, succinimidyl succinamide, succinimidyl glutaramide, or glycidyl ether. In some embodiments, the polyol core derivative is bound to a polyethylene glycol or polypropylene glycol subunit, which is connected to the linker comprising the electrophilic group. The molecular weight of the second compound (the electophilic monomer) is about 100 to 100000. In certain embodiments, the molecular weight of a second compound (an electophilic monomer) is about 100, about 500, about 1000, about 2000, about 3000, about 4000, about 5000, about 6000, about 7000, about 8000, about 9000, about 10000, about 12000, about 15000, about 20000, about 25000, about 30000, about 35000, about 40000, about 50000, about 60000, about 70000, about 80000, about 90000, or about 100000. In certain embodiments, the molecular weight of a second compound is about 500 to 40000. In some embodiments, the molecular weight of a second compound is about 500 to 2000. In certain embodiments, the molecular weight of a second compound is about 15000 to about 40000. In some embodiments, the second compound is water soluble.

Examples of the construction of monomers comprising more than one electrophilic group are shown below with a pentaerythritol core polyol. The compounds shown have a succinimidyl electrophilic group, a glutarate or glutaramide linker, and a variable lengths PEG subunit (e.g., structures below of 4ARM-PEG-SG (D; n=3) and 4ARM-PEG-SGA (E; n=3)). Monomers using other polyol cores or different linkers (e.g., succinate (SS) or succinamide (SSA) are constructed in a similar way.

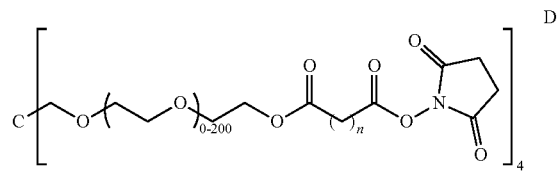

D (n = 1 to 6)

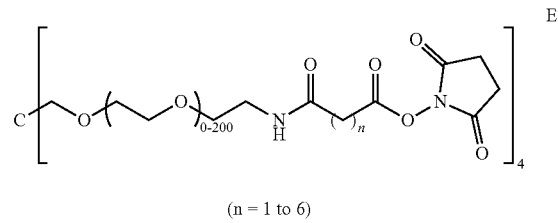

E (n = 1 to 6)

Suitable second compounds comprising an electrophilic group include, but are not limited to, pentaerythritol polyethylene glycol maleimide (4ARM-PEG-MAL) (molecular weight selected from about 5000 to about 40000, e.g., 10000 or 20000), pentaerythritol polyethylene glycol succinimidyl succinate (4ARM-PEG-SS) (molecular weight selected from about 5000 to about 40000, e.g., 10000 or 20000), pentaerythritol polyethylene glycol succinimidyl glutarate (4ARM-PEG-SG) (molecular weight selected from about 5000 to about 40000, e.g., 10000 or 20000), pentaerythritol polyethylene glycol succinimidyl glutaramide (4ARM-PEG-SGA) (molecular weight selected from about 5000 to about 40000, e.g., 10000 or 20000), hexaglycerin polyethylene glycol succinimidyl succinate (8ARM-PEG-SS) (molecular weight selected from about 5000 to about 40000, e.g., 10000 or 20000), hexaglycerin polyethylene glycol succinimidyl glutarate (8ARM-PEG-SG) (molecular weight selected from about 5000 to about 40000, e.g., 10000, 15000, 20000, or 40000), hexaglycerin polyethylene glycol succinimidyl glutaramide (8ARM-PEG-SGA) (molecular weight selected from about 5000 to about 40000, e.g., 10000, 15000, 20000, or 40000), tripentaerythritol polyethylene glycol succinimidyl succinate (8ARM(TP)-PEG-SS) (molecular weight selected from about 5000 to about 40000, e.g., 10000 or 20000), tripentaerythritol polyethylene glycol succinimidyl glutarate (8ARM(TP)-PEG-SG) (molecular weight selected from about 5000 to about 40000, e.g., 10000, 15000, 20000, or 40000), or tripentaerythritol polyethylene glycol succinimidyl glutaramide (8ARM(TP)-PEG-SGA) (molecular weight selected from about 5000 to about 40000, e.g., 10000, 15000, 20000, or 40000). The 4(or 8)ARM-PEG-SG monomers comprise ester groups, while the 4(or 8)ARM-PEG-SGA monomers do not comprise ester groups.

Other suitable second compounds comprising an electrophilic group are sorbitol polyglycidyl ethers, including, but not limited to, sorbitol polyglycidyl ether (DENACOL® EX-611), sorbitol polyglycidyl ether (DENACOL® EX-612), sorbitol polyglycidyl ether (DENACOL® EX-614), sorbitol polyglycidyl ether (DENACOL® EX-614 B), polyglycerol polyglycidyl ether (DENACOL® EX-512), polyglycerol polyglycidyl ether (DENACOL® EX-521), diglycerol polyglycidyl ether (DENACOL® EX-421), glycerol polyglycidyl ether (DENACOL® EX-313), glycerol polyglycidyl ether (DENACOL® EX-313), trimethylolpropane polyglycidyl ether (DENACOL® EX-321), sorbitol polyglycidyl ether (DENACOL® EJ-190).

Viscosity Enhancer

The in vivo gelling ophthalmic pre-formulation, the biocompatible retinal patch, and the in vivo polymerized biocompatible retinal patch comprise a viscosity enhancer. In some instances, the viscosity enhancer increases the viscosity of the pre-formulation, preventing the pre-formulation from spreading and allowing to pre-formulation to stay at the target site. Viscosity enhancers include, but are not limited to, acacia, agar, alginic acid, bentonite, carbomers, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, glyceryl behenate, guar gum, hectorite, hydrogenated vegetable oil type I, hydroxyethyl cellulose, hydroxyethylmethyl cellulose, hydroxypropyl cellulose, hydroxypropyl starch, hypromellose, magnesium aluminum silicate, maltodextrin, methylcellulose, polydextrose, polyethylene glycol, poly(methylvinyl ether/maleic anhydride), polyvinyl acetate phthalate, polyvinyl alcohol, potassium chloride, povidone, propylene glycol alginate, saponite, sodium alginate, sodium chloride, stearyl alcohol, sucrose, sulfobutylether β-cyclodextrin, tragacanth, xanthan gum, and derivatives and mixtures thereof. In certain embodiments, the viscosity enhancer is selected from hydroxyethylcellulose, hydroxypropylmethylcellulose, methylcellulose, polyvinyl alcohol, or polyvinylpyrrolidone. In some embodiments, the viscosity enhancer is methylcellulose or hydroxypropylmethylcellulose. In preferred embodiments, the viscosity enhancer is hydroxypropylmethylcellulose.

In some embodiments, the viscosity enhancer is a bioadhesive or comprises a bioadhesive polymer. In certain instances, a bioadhesive is any adhesive that interfaces with living tissue and/or biological fluid. Bioadhesive polymers include, but are not limited to, hydroxypropylmethylcellulose, hydroxyethyl cellulose, hydroxypropyl cellulose, carboxymethyl cellulose, polyvinyl alcohol, sodium hyaluronate, chitosan, alginate, xanthum gum, acrylic polymers (e.g., carbomer, polycarbophil), and derivatives and mixtures thereof.

In some embodiments, the concentration of the viscosity enhancer in the buffer ranges from 0.1 to 20%. In certain embodiments, the concentration of the viscosity enhancer in the buffer ranges from 5 to 20%. In other embodiments, the concentration of the viscosity enhancer in the buffer ranges from 0.1 to 2%. In specific embodiments, the concentration of the viscosity enhancer in the buffer rangers from 0.1 to 0.5%. In some embodiments, the concentration of the viscosity enhancer is less than 20%, less than 15%, less than 10%, less than 9%, less than 8%, less than 7%, less than 6%, less than 5%, less than 4%, less than 3%, less than 2%, less than 1.8%, less than 1.6%, less than 1.5%, less than 1.4%, less than 1.2%, less than 1%, less than 0.9%, less than 0.8%, less than 0.7%, less than 0.6%, less than 0.5%, less than 0.4%, less than 0.3%, less than 0.2%, or less than 0.1%. In some embodiments, the concentration of the viscosity enhancer is at least 10%, at least 8%, at least 6%, at least 5%, at least 4%, at least 2%, at least 1.8%, at least 1.6%, at least 1.5%, at least 1.4%, at least 1.2%, at least 1%, at least 0.9%, at least 0.8%, at least 0.7%, at least 0.6%, at least 0.5%, at least 0.4%, at least 0.3%, at least 0.2%, or at least 0.1%. In some embodiments, the concentration of the viscosity enhancer is about 20%, about 15%, about 10%, about 9%, about 8%, about 7%, about 6%, about 5%, about 4%, about 3%, about 2%, about 1.8%, about 1.6%, about 1.5%, about 1.4%, about 1.2%, about 1%, about 0.9%, about 0.8%, about 0.7%, about 0.6%, about 0.5%, about 0.4%, about 0.3%, about 0.2%, or about 0.1%.

In certain embodiments, the viscosity of the in vivo gelling ophthalmic pre-formulation is less than 4000 cP, less than 2000 cP, less than 1000 cP, less than 800 cP, less than 600 cP, less than 500 cP, less than 400 cP, less than 200 cP, less than 100 cP, less than 80 cP, less than 60 cP, less than 50 cP, less than 40 cP, less than 20 cP, less than 10 cP, less than 8 cP, less than 6 cP, less than 5 cP, less than 4 cP, less than 3 cP, less than 2 cP, less than 1 cP. In some embodiments, the viscosity of the in vivo gelling ophthalmic pre-formulation is at least 4000 cP, at least 2000 cP, at least 1000 cP, at least 800 cP, at least 600 cP, at least 500 cP, at least 400 cP, at least 200 cP, at least 100 cP, at least 80 cP, at least 60 cP, at least 50 cP, at least 40 cP, at least 20 cP, at least 10 cP, at least 8 cP, at least 6 cP, at least 5 cP, at least 4 cP, at least 3 cP, at least 2 cP, at least 1 cP. In certain embodiments, the viscosity of the in vivo gelling ophthalmic pre-formulation is about 4000 cP, about 2000 cP, about 1000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP, about 1 cP. In some embodiments, the viscosity of the in vivo gelling ophthalmic pre-formulation is between about 5 cP and 50 cP. In certain embodiments, the viscosity of the in vivo gelling ophthalmic pre-formulation is between about 5 cP and 500 cP.

Formation of Hydrogels

In certain embodiments, the first and second compounds comprising more than one nucleophilic or more than one electrophilic group safely undergo polymerization at a target site inside a mammalian body, for instance in the eye, for example at the site of a retinal tear. In certain embodiments, the in vivo gelling ophthalmic pre-formulation replaces, partially or complete, the vitreous in the eye. In some embodiments, the first compound and the second compound are monomers forming a polymer through the reaction of a nucleophilic group in the first compound with the electrophilic group in the second compound. In certain embodiments, the monomers are polymerized at a predetermined time. In some embodiments, the monomers are polymerized under mild and nearly neutral pH conditions. In certain embodiments, the hydrogel polymer does not change volume after curing.

In some embodiments, the first and second compound react to form amide, thioester, or thioether bonds. When a thiol nucleophile reacts with a succinimidyl electrophile, a thioester is formed. When an amino nucleophile reacts with a succinimidyl electrophile, an amide is formed.

In some embodiments, one or more first compounds comprising an amino group react with one or more second compounds comprising a succinimidyl ester group to form amide linked first and second monomer units. In certain embodiments, one or more first compounds comprising a thiol group react with one or more second compounds comprising a succinimidyl ester group to form thioester linked first and second monomer units. In some embodiments, one or more first compounds comprising an amino group react with one or more second compounds comprising an epoxide group to from amine linked first and second monomer units. In certain embodiments, one or more first compounds comprising a thiol group react with one or more second compounds comprising an epoxide group to form thioether linked first and second monomer units.

In some embodiments, a first compound is mixed with a different first compound before addition to one or more second compounds. In other embodiments, a second compound is mixed with a different second compound before addition to one or more first compounds. In certain embodiments, the properties of the in vivo gelling ophthalmic pre-formulation and the biocompatible hydrogel polymer are controlled by the properties of the at least one first and at least one second monomer mixture.

In some embodiments, one first compound is used in the biocompatible hydrogel polymer. In certain embodiments, two different first compounds are mixed and used in the biocompatible hydrogel polymer. In some embodiments, three different first compounds are mixed and used in the biocompatible hydrogel polymer. In certain embodiments, four or more different first compounds are mixed and used in the biocompatible hydrogel polymer.

In some embodiments, one second compound is used in the biocompatible hydrogel polymer. In certain embodiments, two different second compounds are mixed and used in the biocompatible hydrogel polymer. In some embodiments, three different second compounds are mixed and used in the biocompatible hydrogel polymer. In certain embodiments, four or more different second compounds are mixed and used in the biocompatible hydrogel polymer.

In some embodiments, a first compound comprising ether linkages to the nucleophilic group are mixed with a different first compound comprising ester linkages to the nucleophilic group. This allows the control of the concentration of ester groups in the resulting biocompatible hydrogel polymer. In certain embodiments, a second compound comprising ester linkages to the electrophilic group are mixed with a different second compound comprising ether linkages to the electrophilic group. In some embodiments, a second compound comprising ester linkages to the electrophilic group are mixed with a different second compound comprising amide linkages to the electrophilic group. In certain embodiments, a second compound comprising amide linkages to the electrophilic group are mixed with a different second compound comprising ether linkages to the electrophilic group.

In some embodiments, a first compound comprising an aminoacetate nucleophile is mixed with a different first compound comprising an ethylamine ether nucleophile at a specified molar ratio (x/y). In certain embodiments, the molar ratio (x/y) is 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. In certain embodiments, the mixture of two first compounds is mixed with one or more second compounds at a molar amount equivalent to the sum of x and y. In some embodiments, the ratio of the combined molar amount of the two first compounds to the molar amount of the second compound is not equivalent.

In some embodiments, the molar ratio of the combined molar amount of the first compounds to the combined molar amount of the second compounds is greater than 1. In certain embodiments, the molar ratio of the combined molar amount of the first compounds to the combined molar amount of the second compounds is less than 1. In some embodiments, the molar ratio of the combined molar amount of the first compounds to the combined molar amount of the second compounds is about 1. In certain embodiments, the molar ratio of the combined molar amount of the first compounds to the combined molar amount of the second compounds is about 10:1, about 9:1, about 8:1, about 7:1, about 6:1, about 5:1, about 4:1, about 3:1, about 2:1, or about 1:1. In some embodiments, the molar ratio of the combined molar amount of the first compounds to the combined molar amount of the second compounds is about 1:10, about 1:9, about 1:8, about 1:7, about 1:6, about 1:5, about 1:4, about 1:3, about 1:2, or about 1:1. In certain embodiments, when the molar ratio of the combined molar amount of the first compounds (e.g., amines) to the combined molar amount of the second compounds (e.g., esters) is greater than 1, the stickiness of the resulting retinal patch is increased.

In some embodiments, the first compound comprising more than one nucleophilic group and the therapeutic agent are pre-mixed in an aqueous buffer. Once pre-mixing is complete, the second compound comprising more than one electrophilic group is added to the pre-mixture. Shortly after final mixing, the hydrogel polymer is delivered to the target site. In certain embodiments, the optional radiopaque material is added to the pre-mix, the second compound, or to the mixture just before delivery of the hydrogel polymer mixture to the target site.

In other embodiments, the second compound comprising more than one electrophilic group and the therapeutic agent are pre-mixed in an aqueous buffer. Once pre-mixing is complete, the first compound comprising more than one nucleophilic group is added to the pre-mixture. Shortly after final mixing, the hydrogel polymer is delivered to the target site. In certain embodiments, the optional radiopaque material is added to the pre-mix, the first compound, or to the mixture just before delivery of the hydrogel polymer mixture to the target site.

In some embodiments, the first compound comprising more than one nucleophilic group and the second compound comprising more than one electrophilic group are mixed together in an aqueous buffer in the pH range of about 5.0 to about 9.5, whereby a biocompatible hydrogel polymer is formed. In certain embodiments, the first compound comprising more than one nucleophilic group and/or the second compound comprising more than one electrophilic group are individually diluted in an aqueous buffer in the pH range of about 5.0 to about 9.5, wherein the individual dilutions or neat monomers are mixed, whereby a biocompatible hydrogel polymer is formed. In some embodiments, the aqueous buffer is in the pH range of about 6.0 to about 8.5. In certain embodiments, the aqueous buffer is in the pH range of about 8.

In certain embodiments, the concentration of the monomers in the aqueous is from about 1% to about 100%. In some embodiments, the dilution is used to adjust the viscosity of the monomer dilution. In certain embodiments, the concentration of the monomers in the aqueous buffer is about 1%, is about 1.5%, is about 2%, is about 2.5%, is about 3%, is about 3.5%, is about 4%, is about 4.5%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the electrophilic and nucleophilic monomers are mixed in such ratio that there is a slight excess of electrophilic groups present in the mixture. In certain embodiments, this excess is about 10%, about 5%, about 2%, about 1%, about 0.9%, about 0.8%, about 0.7%, about 0.6%, about 0.5%, about 0.4%, about 0.3%, about 0.2%, about 0.1%, or less than 0.1%.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling ophthalmic pre-formulation. In certain embodiments, temperature influences the gelling time of the in vivo gelling ophthalmic pre-formulation. In some embodiments, the type of aqueous buffer influences the gelling time of the in vivo gelling ophthalmic pre-formulation. In certain embodiments, the concentration of the aqueous buffer influences the gelling time of the in vivo gelling ophthalmic pre-formulation. In some embodiments, the nucleophilicity and/or electrophilicity of the nucleophilic and electrophilic groups of the monomers influences the gelling time of the in vivo gelling ophthalmic pre-formulation.

In some embodiments, the gelling time or curing time of the biocompatible hydrogel polymer is controlled by the pH of the aqueous buffer. In certain embodiments, the gelling time decreases with an increase in pH. In some embodiments, the gelling time decreases with an increase in buffer concentration. In certain embodiments, the gelling time decreases with an increase in temperature. In some embodiments, the gelling time decreases with an increase in solution (monomer) concentration.

In certain embodiments, the gelling time is between about 20 seconds and 10 minutes. In some embodiments, the gelling time is less than 30 minutes, less than 20 minutes, less than 10 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.4 minutes, less than 1.2 minutes, less than 1.0 minutes, less than 0.8 minutes, less than 0.6 minutes, or less than 0.4 minutes. In certain embodiments, the pH of the aqueous buffer is from about 5 to about 9.5. In some embodiments, the pH of the aqueous buffer is from about 7.0 to about 9.5. In specific embodiments, the pH of the aqueous buffer is about 8. In some embodiments, the pH of the aqueous buffer is about 5, about 5.5, about 6.0, about 6.5, about 6.6, about 6.7, about 6.8, about 6.9, about 7.0, about 7.1, about 7.2, about 7.3, about 7.4, about 7.5, about 7.6, about 7.8, about 7.9, about 8.0, about 8.1 about 8.2 about 8.3, about 8.4, about 8.5, about 9.0, or about 9.5.

In certain embodiments, the gelling time or curing time of the biocompatible hydrogel polymer is controlled by the type of aqueous buffer. In some embodiments, the aqueous buffer is a physiologically acceptable buffer. In certain embodiments, aqueous buffers include, but are not limited to, aqueous saline solutions, phosphate buffered saline, borate buffered saline, a combination of borate and phosphate buffers wherein each component is dissolved in separate buffers, N-2-Hydroxyethylpiperazine-N'-2-hydroxypropanesulfonic acid (HEPES), 3-(N-Morpholino) propanesulfonic acid (MOPS), 2-([2-Hydroxy-1,1-bis(hydroxymethyl)ethyl]amino)ethanesulfonic acid (TES), 3-[N-tris(Hydroxy-methyl) ethylamino]-2-hydroxyethyl]-1-piperazinepropanesulfonic acid (EPPS), Tris[hydroxymethyl]-aminomethane (THAM), and Tris[hydroxymethyl]methyl aminomethane (TRIS). In some embodiments, the thiol-ester chemistry (e.g., ETTMP nucleophile with SGA or SG electrophile) is performed in borate buffer. In certain embodiments, the amine-ester chemistry (NH2 or AA nucleophile with SGA or SG electrophile) is performed in phosphate buffer.

In some embodiments, the tack of the retinal patch is about 40 mN. In certain embodiments, the tack of the retinal patch is between about 20 mN and about 100 mN. In some embodiments, the tack of the retinal patch is between about 30 mN and about 50 mN. In certain embodiments, the firmness of the retinal patch is between about 30 g to about 100 g. In some embodiments, the firmness of the retinal patch is between about 45 g to about 90 g. In certain embodiments, the elastic modulus of the retinal patch is between about 50 Pa to about 500 Pa. In some embodiments, the elastic modulus of the retinal patch is between about 100 Pa to about 400 Pa.

In certain embodiments, the first compound and the second compound do not react with the therapeutic agent during formation of the biocompatible hydrogel polymer. In some embodiments, the therapeutic agent remains unchanged after polymerization of the first and second compounds (i.e., monomers). In certain embodiments, the therapeutic agent does not change the properties of the hydrogel polymer. In some embodiments, the physiochemical properties of the therapeutic agent and the hydrogel polymer formulation are not affected by the polymerization of the monomers.

Area of for Treatment—Target Sites

In certain embodiments, the target site is inside a mammal. In some embodiments, the target site is inside a human being. In certain embodiments, the target site is on the human body. In some embodiments, the target site is accessible through surgery. In certain embodiments, the target site is accessible through minimally invasive surgery. In some embodiments, the target site is accessible through an endoscopic device. In certain embodiments, the target site is in or on an eye. In some embodiments, a method of treating a retinal tear, hole, or retinal detachment comprises delivering the in vivo gelling ophthalmic pre-formulation to the site of the hole, tear, or detachment under local anesthesia. In certain embodiments, the in vivo gelling ophthalmic pre-formulation is delivered through a sharp 24 to 28 gauge needle.

In some embodiments, an in vivo gelling ophthalmic pre-formulation or a biocompatible hydrogel polymer is used as a sealant or adhesive with or without a therapeutic agent. In certain embodiments, the in vivo gelling ophthalmic pre-formulation or biocompatible hydrogel polymer is used to seal retinal tears inside a human eye. In other embodiments, the in vivo gelling ophthalmic pre-formulation or biocompatible hydrogel polymer is used to fill cavities in the human body, e.g., an eye as partial or complete replacement of the vitreous humour.

Delivery of the Hydrogel Formulation to a Target Site

In some embodiments, the in vivo gelling ophthalmic pre-formulation is delivered as an in vivo gelling ophthalmic pre-formulation to a target site through a catheter or a needle to form a biocompatible hydrogel polymer at the target site. In certain embodiments, the needle or catheter is attached or part of a delivery device.

In other embodiments, the in vivo gelling ophthalmic pre-formulation is delivered to the target site in the eye using a syringe and needle. In some embodiments, a delivery device is used to deliver the in vivo gelling ophthalmic pre-formulation to the target site. In some embodiments, the needle has an outer diameter of about 4 mm, about 3.8 mm, about 3.6 mm, about 3.4 mm, about 3.2 mm, about 3.0 mm, about 2.8 mm, about 2.6 mm, about 2.4 mm, about 2.2 mm, about 2.0 mm, about 1.8 mm, about 1.6 mm, about 1.4 mm, about 1.2 mm, about 1.0 mm, about 0.8 mm, or about 0.6 mm. In preferred embodiments, the needle has an outer diameter of about 1.2 mm or less. In certain embodiments, the viscosity of the in vivo gelling ophthalmic pre-formulation is close to the viscosity of water when delivering the mixture to the site of the tumor through the catheter. In some embodiments, the in vivo gelling ophthalmic pre-formulation forming the biocompatible hydrogel further comprises a pharmaceutically acceptable viscosity enhancer to ensure that the pre-formulation stays in place at the target site during the gelling process.

In certain embodiments, between 1 and 3 mL of the in vivo gelling ophthalmic pre-formulation optionally comprising a therapeutic agent is delivered to a target site. In some embodiments, about 12 mL, about 11 mL, about 10 mL, about 9 mL, about 8 mL, about 7.5 mL, about 7.0 mL, about 6.5 mL, about 6.0 mL, about 5.5 mL, about 5.0 mL, about 4.5 mL, about 4.0 mL, about 3.5 mL, about 3.0 mL, about 2.5 mL, about 2.0 mL, about 1.5 mL, about 1.0 mL, about 0.5 mL, about 0.2 mL, about 0.1 mL, about 0.05 mL or about 0.01 mL in vivo gelling ophthalmic pre-formulation optionally comprising a therapeutic agent is delivered to a target site. In certain embodiments, less than 12 mL, less than 11 mL, less than 10 mL, less than 9 mL, less than 8 mL, less than 7.5 mL, less than 7.0 mL, less than 6.5 mL, less than 6.0 mL, less than 5.5 mL, less than 5.0 mL, less than 4.5 mL, less than 4.0 mL, less than 3.5 mL, less than 3.0 mL, less than 2.5 mL, less than 2.0 mL, less than 1.5 mL, less than 1.0 mL, less than 0.5 mL, less than 0.2 mL, less than 0.1 mL, less than 0.05 mL, or less than 0.01 mL in vivo gelling ophthalmic pre-formulation optionally comprising a therapeutic agent is delivered to a target site. In certain embodiments, about 0.05 to 5 mL in vivo gelling ophthalmic pre-formulation optionally comprising a therapeutic agent is delivered to a target site.

In some embodiments, the gelling time of the biocompatible hydrogel polymer is set according to the preference of the doctor delivering the hydrogel polymer mixture to a target site. In most instances, a physician delivers the hydrogel polymer mixture to the target within 15 to 30 seconds. In some embodiments, the hydrogel polymer mixture gels after delivery at the target site, covering the target site.

In some embodiments, the gelling time or curing time of the biocompatible hydrogel polymer is controlled by the pH of the aqueous buffer. In certain embodiments, the gelling time is between about 20 seconds and 10 minutes. In preferred embodiments, the gelling time is about 90 seconds. In some embodiments, the gelling time is less than 120 minutes, less than 90 minutes, less than 60 minutes, less than 50 minutes, less than 40 minutes, less than 30 minutes, less than 20 minutes, less than 10 minutes, less than 9 minutes, less than 8 minutes, less than 7 minutes, less than 6 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.5 minutes, less than 1.4 minutes, less than 1.2 minutes, less than 1.0 minutes, less than 0.8 minutes, less than 0.6 minutes, or less than 0.4 minutes. In certain embodiments, the gelling time is more than 120 minutes, more than 90 minutes, more than 60 minutes, more than 50 minutes, more than 40 minutes, more than 30 minutes, more than 20 minutes, more than 10 minutes, more than 9 minutes, more than 8 minutes, more than 7 minutes, more than 6 minutes, more than 5 minutes, more than 4.8 minutes, more than 4.6 minutes, more than 4.4 minutes, more than 4.2 minutes, more than 4.0 minutes, more than 3.8 minutes, more than 3.6 minutes, more than 3.4 minutes, more than 3.2 minutes, more than 3.0 minutes, more than 2.8 minutes, more than 2.6 minutes, more than 2.4 minutes, more than 2.2 minutes, more than 2.0 minutes, more than 1.8 minutes, more than 1.6 minutes, more than 1.5 minutes, more than 1.4 minutes, more than 1.2 minutes, more than 1.0 minutes, more than 0.8 minutes, more than 0.6 minutes, or more than 0.4 minutes. In some embodiments, the gelling time is about 120 minutes, about 90 minutes, about 60 minutes, about 50 minutes, about 40 minutes, about 30 minutes, about 20 minutes, about 10 minutes, about 9 minutes, about 8 minutes, about 7 minutes, about 6 minutes, about 5 minutes, about 4.8 minutes, about 4.6 minutes, about 4.4 minutes, about 4.2 minutes, about 4.0 minutes, about 3.8 minutes, about 3.6 minutes, about 3.4 minutes, about 3.2 minutes, about 3.0 minutes, about 2.8 minutes, about 2.6 minutes, about 2.4 minutes, about 2.2 minutes, about 2.0 minutes, about 1.8 minutes, about 1.6 minutes, about 1.5 minutes, about 1.4 minutes, about 1.2 minutes, about 1.0 minutes, about 0.8 minutes, about 0.6 minutes, or about 0.4 minutes.

In certain embodiments, the pH of the aqueous buffer is from about 5.0 to about 9.5. In some embodiments, the pH of the aqueous buffer is from about 6.0 to about 8.5. In specific embodiments, the pH of the aqueous buffer is about 8.0. In some embodiments, the pH is about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.9, about 9, about 9.1 about 9.2, about 9.3, about 9.4, or about 9.5.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling ophthalmic pre-formulation.

In some embodiments, curing of the biocompatible hydrogel polymer is verified post-administration. In certain embodiments, the verification is performed in vivo at the delivery site. In other embodiments, the verification is performed ex vivo. In some embodiments, curing of the biocompatible hydrogel polymer is verified visually. A lack of flow of the biocompatible hydrogel polymer indicates that the biocompatible hydrogel polymer has gelled and the hydrogel is sufficiently cured. In further embodiments, curing of the biocompatible hydrogel polymer is verified by evaluation of the residue in the delivery device, for instance the residue in the catheter of the bronchoscope or other endoscopic device, or the residue in the syringe used to deliver the biocompatible hydrogel polymer. In other embodiments, curing of the biocompatible hydrogel polymer is verified by depositing a small sample (e.g., ~1 mL) on a piece of paper or in a small vessel and subsequent evaluation of the flow characteristics after the gelling time has passed.

In some embodiments, the in vivo gelling ophthalmic pre-formulation optionally comprising one or more therapeutic agents is delivered to the target site so that the pre-formulation mostly covers the target site. In certain embodiments, the in vivo gelling ophthalmic pre-formulation substantially covers an exposed portion of diseased tissue. In some embodiments, the in vivo gelling ophthalmic pre-formulation does not spread to any other location intentionally. In some embodiments, the in vivo gelling ophthalmic pre-formulation substantially covers diseased tissue and does not significantly cover healthy tissue. In certain embodiments, the biocompatible hydrogel polymer does not significantly cover healthy tissue. In some embodiments, in vivo gelling ophthalmic pre-formulation gels over the target site and thoroughly covers diseased tissue. In some embodiments, the biocompatible hydrogel polymer adheres to tissue.

Bioabsorbance of the Hydrogel

In some embodiments, the biocompatible hydrogel polymer is a bioabsorbable polymer. In certain embodiments, the biocompatible hydrogel polymer is bioabsorbed within about 5 to 30 days. In some embodiments, the biocompatible hydrogel polymer is bioabsorbed within about 30 to 180 days. In preferred embodiments, the biocompatible hydrogel polymer is bioabsorbed within about 1 to 70 days. In some embodiments the biocompatible hydrogel polymer is bioabsorbed within about 365 days, 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, or about 1 day. In certain embodiments the biocompatible hydrogel polymer is bioabsorbed within less than 365 days, 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, or less than 1 day. In some embodiments the biocompatible hydrogel polymer is bioabsorbed within more than 365 days, 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, or more than 1 day. In some embodiments, the biocompatible hydrogel polymer is substantially non-bioabsorbable.

The biocompatible hydrogel polymer is slowly bioabsorbed, dissolved, and or excreted. In some instances, the rate of bioabsorption is controlled by the number of ester groups in the biocompatible and/or biodegradable hydrogel polymer. In other instances, the higher the concentration of ester units is in the biocompatible hydrogel polymer, the longer is its lifetime in the body. In further instances, the electron density at the carbonyl of the ester unit controls the lifetime of the hydrogel polymer in the body. In certain instances, biocompatible hydrogel polymers without ester groups are essentially not biodegradable. In additional instances, the molecular weight of the first and second compounds controls the lifetime of the hydrogel polymer in the body. In further instances, the number of ester groups per gram of polymer controls the lifetime of the hydrogel polymer in the body.

In some instances, the lifetime of the hydrogel polymer can be estimated using a model, which controls the temperature and pH at physiological levels while exposing the hydrogel polymer to a buffer solution. In certain instances, the biodegradation of the hydrogel polymer is substantially non-enzymatic degradation.

In some embodiments, the selection of reaction conditions determines the degradation time of the hydrogel polymer. In certain embodiments, the concentration of the first compound and second compound monomers determines the degradation time of the resulting hydrogel polymer. In some instances, a higher monomer concentration leads to a higher degree of cross-linking in the resulting hydrogel polymer. In certain instances, more cross-linking leads to a later degradation of the hydrogel polymer.

In certain embodiments, the composition of the linker in the first and/or second compound influences the speed of degradation of the resulting hydrogel polymer. In some embodiments, the more ester groups are present in the hydrogel polymer, the faster the degradation of the hydrogel polymer. In certain embodiments, the higher the concentration of mercaptopropionate (ETTMP), acetate amine (AA), glutarate or succinate (SG or SS) monomers, the faster the rate of degradation.

Retinal Patch or Suture in the Treatment of Retinal Disease

In some embodiments, the in vivo gelling ophthalmic pre-formulation described herein is delivered to a target site of an eye to treat retinal detachment. In certain embodiments, the in vivo gelling ophthalmic pre-formulation is delivered to a target site of an eye to treat blindness. In some embodiments, the in vivo gelling ophthalmic pre-formulation forms a biocompatible retinal patch at the target site inside the eye. In certain embodiments, the in vivo gelling ophthalmic pre-formulation acts as a retinal glue at a target site inside the eye. In some embodiments, the in vivo gelling ophthalmic pre-formulation forms a retinal suture. In certain embodiments, the retinal patch, retinal glue, or retinal suture gels at least in part at the target site inside the eye. In some embodiments, the retinal patch, retinal glue, or retinal suture gels at least in part at a retinal tear inside the eye. In certain embodiments, the retinal patch, retinal glue, or retinal suture polymerizes at least in part at the target site inside the eye. In some embodiments, the retinal patch, retinal glue, or retinal suture polymerizes at least in part at a retinal tear inside the eye. In some embodiments, the retinal patch, retinal glue, or retinal suture adheres at least partially to the target site.

In certain embodiments, the in vivo gelling hydrogel polymer is used as a "liquid suture" or as a drug delivery platform to transport medications directly to the targeted site in the eye. In some embodiments, the spreadability, viscosity, optical clarity, and adhesive properties of the hydrogel formulation are optimized to create materials ideal as liquid sutures for the treatment of retinal detachment (re-attachment of detached retina). In certain embodiments, the gel time is controlled from 50 seconds to 15 minutes.

Control of Release Rate of a Therapeutic Agent

In some embodiments, the biocompatible hydrogel polymer slowly delivers a therapeutic agent to a target site by diffusion and/or osmosis over time ranging from hours to days. In certain embodiments, the drug is delivered directly to the target site. In some embodiments, the procedure of delivering a biocompatible hydrogel polymer comprising a therapeutic agent to a target site is repeated several times, if needed. In other embodiments, the therapeutic agent is released from the biocompatible hydrogel polymer through biodegradation of the hydrogel polymer. In some embodiments, the therapeutic agent is released through a combination of diffusion, osmosis, and/or hydrogel degradation mechanisms. In certain embodiments, the release profile of the therapeutic agent from the hydrogel polymer is unimodal. In some embodiments, the release profile of the therapeutic agent from the hydrogel polymer is bimodal. In certain embodiments, the release profile of the therapeutic agent from the hydrogel polymer is multimodal.

In some embodiments, the therapeutic agent is released from the biocompatible hydrogel polymer though diffusion or osmosis. In certain embodiments, the therapeutic agent is substantially released from the biocompatible hydrogel polymer within 180 days. In some embodiments, the therapeutic agent is substantially released from the biocompatible hydrogel polymer within 14 days. In certain embodiments, the therapeutic agent is substantially released from the biocompatible hydrogel polymer within 24 hours. In some embodiments, the therapeutic agent is substantially released from the biocompatible hydrogel polymer within one hour. In certain embodiments, the therapeutic agent is substantially released from the biocompatible hydrogel polymer within about 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, about 1 day, about 0.5 day, about 6 hours, about 4 hours, about 2 hours, about or 1 hour. In some embodiments, the therapeutic agent is substantially released from the biocompatible hydrogel polymer within more than 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, more than 1 day, more than 0.5 day, more than 6 hours, more than 4 hours, more than 2 hours, more than or 1 hour. In certain embodiments, the therapeutic agent is substantially released from the biocompatible hydrogel polymer within less than 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, less than 1 day, less than 0.5 day, less than 6 hours, less than 4 hours, less than 2 hours, less than or 1 hour. In some embodiments, the therapeutic agent is substantially released from the biocompatible hydrogel polymer within about one day to about fourteen days. In certain embodiments, the therapeutic agent is substantially released from the biocompatible hydrogel polymer within about one day to about 70 days.

In some embodiments, the therapeutic agent is a biomolecule and the release of the biomolecule from the hydrogel polymer is controlled by the composition of the hydrogel polymer. In certain embodiments, the biomolecule is released when the hydrogel polymer starts to degrade. In some embodiments, the pore size of the hydrogel polymer is small enough to prevent the early phase release of the biomolecule (i.e., release before the degradation of the hydrogel polymer). In certain embodiments, the pore size of the hydrogel polymer is large enough to allow the early phase release of the biomolecule. In some embodiments, the ratio of the pore size of the hydrogel polymer to the size of the biomolecule determines the release rate of the biomolecule.

Exemplary Antifungals

In some embodiments, the biocompatible hydrogel polymer comprises an antifungal agent as the therapeutic agent. In certain embodiments, the antifungal agent is a polyene antifungal, an imidazole, triazole, or thiazole antifungal, a triazole antifungal, a thiazole antifungal, an allylamine derivative, or an echinocandin derivative. Examples of antifungal agents include, but are not limited to, Polyene derivatives like natamycin, rimocidin, filipin, nystatin, amphotericin B, candicin, hamycin; Imidazole derivatives like miconazole, ketoconazole, clotrimazole, econazole, omoconazole, bifonazole, butoconazole, fenticonazole, isoconazole, oxiconazole, sertaconazole, sulconazole, tioconazole; Tetrazole derivatives like fluconazole, itraconazole, isavuconazole, posaconazole, voriconzaole, terconazole, albaconazole; Thiazole derivatives like abafungin; Allylamine derivative like terbifine, naftifine, butenafine; Echinocandin derivatives like anidulafungin, caspofungin, micafungin; Other antifungals like polygodial, benzoic acid, ciclopirox, tonaftate, undecylenic acid, flycytosine, griseofulvin, haloprogin, sodium bicarbonate, pirctone olamine, zinc pyrithione, selenium sulfide, tar, or tea tree oil.

Exemplary Antibiotics

In some embodiments, the biocompatible hydrogel polymer comprises an antibiotic. In certain embodiments, the antibiotic agent is a aminoglycoside, ansamycin, carbacephem, carbapenem, cephalosporin, glycopeptide, lincosamide, lipopeptide, macrolide, monobactam, nitrofurans, penicillin, polypeptide, quinolone, sulfonamide, or tetracycline. Examples of antibiotic agents include, but are not limited to, Aminoglycoside derivatives like amikacin, gentamicin, kanamycin, neomycin, netilmicin, tobramicin, paromomycin; Ansamycin derivatives like geldanamycin, herbimycin; Carbacephem derivatives like loracarbef, Carbapenem derivatives like ertapenem, doripenem, imipenem, meropenem; Cephalosporin derivatives like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; Glycopeptide derivatives like teicoplanin, vancomycin, telavancin; Lincosamides like clindamycin, lincomycin; Lipopeptide derivatives like daptomycin; Macrolide derivatives like azithromycin, clarithromycin, dirithromycin, erythromycin, roxithromycin, troleandomycin; telithreomycin, spectinomycin; Monobactam derivatives like aztreonam; Nitrofuran derivatives like furazolidone, nitrofurantoin; Penicillin derivatives like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; Penicillin combinations like amoxicillin/clavulanate, ampicillin/sulbactam, piperacillin/tazobactam, ticarcillin/clavulanate; Polypeptide derivatives like bacitracin, colistin, polymyxin B; Quinolone derivatives like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; Sulfonamide derivatives like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; Tetracyclin derivatives like demeclocycline, doxycycline, minocycline, oxytetracycline, tetracycline; Derivatives against mycobacteria like clofazimine, dapsone, capreomycin, cycloserine, ethambutol, ethioamide, isoniazid, pyrazinamide, rifampin, refampicin, rifabutin, rifapentine, streptomycin; or other antibiotic agents like arsphenamine, chloramphenicol, fosfomycin, fusidic acid, linezolid, metronidazole, mupirocin, platensimycin, quinupristin/dalfopristin, rifaximin, thiampheniol, tigecycline, tinidazole.

Exemplary Antiviral Agents

In some embodiments, the biocompatible hydrogel polymer comprises an antiviral agent. In certain embodiments, the antiviral agent is a nucleoside reverse transcriptase inhibitor, a non-nucleoside reverse transcriptase inhibitor, a fusion inhibitor, an integrase inhibitor, a nucleoside analog, a protease inhibitor, a reverse transcriptase inhibitor. Examples of antiviral agents include, but are not limited to, abacavir, aciclovir, acyclovir, adefovir, amantadine, amprenavir, ampligen, arbidol, atazanavir, boceprevir, cidofovir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, interferon, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir (Valtrex), valganciclovir, vicriviroc, vidarabine, viramidine, zalcitabine, zanamivir, zidovudine.

Exemplary Immunosuppressive Agents

In some embodiments, the biocompatible hydrogel polymer comprises an immunosuppressive agent. In certain embodiments, the immunosuppressive agent is a calcinuerin inhibitor, mTor inhibitor, an anti-proliferative agent (e.g., an alkylating agent or an antimetabolite), a glucocorticosteroid, an antibody, or an agent acting on immunophilins. Examples of immunosuppressive agents include, but are not limited to, Calcineurin inhibitors like ciclosporin, tacrolimus; mTOR inhibitors like sirolimus, everolimus; Anti-proliferatives like azathioprine, mycophenolic acid; Corticosteroids like prednisolone, hydrocortisone; Monoclonal anti-IL-2Ra receptor antibodies like basiliximab, daclizumab; Polyclonal anti-T-cell antibodies like antithymocyte globulin (ATG), antilymphocyte globulin (ALG); Monoclonal anti-CD20 antibodies like rituximab; Interleukin inhibitors like daclizumab, basiliximab, anakinra, rilonacept, ustekinumab, mepolizumab, tocilizumab, canakinumab, briakinumab; Tumor necrosis factor alpha (TNF-α) inhibitors like etanercept, infliximab, afelimomab, adalimumab, certolizumab pegol, golimumab; Selective immunosuppressants like muromonab-CD3, antilymphocyte immunoglobulin (horse), antithymocyte immunoglobulin (rabbit), mycophenolic acid, sirolimus, leflunomide, alefacept, everolimus, gusperimus, efalizumab, abetimus, natalizumab, abatacept, eculizumab, belimumab, fingolimod, belatacept; or Other immunosuppressants like azathioprine, thalidomide, methotrexate, lenalidomide Exemplary Hemostasis Agents In some embodiments, the biocompatible hydrogel polymer comprises a hemostasis agent (or antihemorrhagic agent). In certain embodiments, the hemostasis agent is an antifibrinolytic (amino acid or proteinase inhibitor), a vitamin K, fibrinogen, a local hemostatic, or a blood coagulation factor. Examples of hemostasis agents include, but are not limited to, Amino acids like aminocaproic acid, tranexamic acid, aminomethylbenzoic acid; Proteinase inhibitors like aprotinin, alfa1 antitrypsin, C1-inhibitor, camostat; Vitamin K like phytomenadione, menadione; Fibrinogen like Human fibrinogen; Local hemostatics like absorbable gelatin sponge, oxidized cellulose, tetragalacturonic acid hydroxymethylester, adrenalone, thrombin, collagen, calcium alginate, epinephrine, human fibrinogen; Blood coagulation factors like coagulation factor IX, II, VII and X in combination, coagulation factor VIII, factor VIII inhibitor bypassing activity, coagulation factor IX, coagulation factor VII, von Willebrand factor and coagulation factor VIII in combination, coagulation factor XIII, eptacog alfa, nonacog alfa, thrombin; Other systemic hemostatics like etamsylate, carbazochrome, batroxobin, romiplostim, eltrombopag.

Exemplary Non-Steroidal Anti-Inflammatory Agents

In some embodiments, the biocompatible hydrogel polymer comprises an anti-inflammatory agent. In certain embodiments, the anti-inflammatory agent is a non-steroidal anti-inflammatory agent. In other embodiments, the anti-inflammatory agent is a glucocorticosteroid. In some embodiments, the non-steroidal anti-inflammatory agent is a butylpyrazolidine, an acetic acid derivative, oxicam, propionic acid derivative, fenamate, or coxib. Examples of anti-inflammatory agents include, but are not limited to, Butylpyrazolidines like phenylbutazone, mofebutazone, oxyphenbutazone, clofezone, kebuzone; Acetic acid derivatives and related substances like indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, indometacin combinations, diclofenac combinations; Oxicams like piroxicam, tenoxicam, droxicam, lornoxicam, meloxicam; Propionic acid derivatives like ibuprofen, naproxen, ketoprofen, fenoprofen, fenbufen, benoxaprofen, suprofen, pirprofen, flurbiprofen, indoprofen, tioprofenoic acid, oxaprozin, ibuproxam, dexibuprofen, flunoxaprofen, alminoprofen, dexketoprofen, naproxcinod; Fenamates like mefenamic acid, tolfenamic acid, flufenamic acid, meclofenamic acid; Coxibs like celecoxib, rofecoxib, valdecoxib, parecoxib, etoricoxib, lumiracoxib; Other anti-inflammatory and antirheumatic agents like nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate.

Exemplary Analgesics and Anesthetics

In some embodiments, the biocompatible hydrogel polymer comprises an analgesic or anesthetic agent. In certain embodiments, the analgesic or anesthetic agent comprises paracetamol, an opiate, diproqualone, phenazone, cocaine, or lidocaine. In certain embodiments, the opioid is a natural opium alkaloid, phenylpiperidine derivative, diphenylpropylamine derivative, benzomorphan derivative, oripavin derivative, or morphinan derivative. In some embodiments, the analgesic is a salicylic acid derivative, pyrazolone, or anilide. In other embodiments, the analgesic is an ergot alkaloid, corticosteroid derivative, or selective serotonin (5HT1) agonist. Examples of local anesthetics include, but are not limited to, Esters of aminobenzoic acid like metabutethamine, procaine, tetracaine, chloroprocaine, benzocaine; Amides like bupivacaine, lidocaine, mepivacaine, prilocaine, butanilicaine, cinchocaine, etidocaine, articaine, ropivacaine, levobupivacaine, tetracaine, chloroprocaine, benzocaine; Esters of benzoic acid like cocaine; Other local anesthetics like ethyl chloride, dyclonine, phenol, capsaicin.

Exemplary Proteins and Other Biomolecules

In some embodiments, the biocompatible hydrogel polymer comprises a protein or other biomolecule. Examples of proteins and other biomolecules include, but are not limited to abarelix, abatacept, acarbose, adalimumab, alglucosidase alfa, Antihemophilic Factor Recombinant, antithrombin recombinant lyophilized powder for reconstitution, belatacept, belimumab, bevacizumab, botulinum toxin type A, canakinumab, certolizumab pegol, Cetrotide, cetuximab, chorionic human recombinant gonadotropin, coagulation Factor IX (recombinant), collagenase clostridium histolyticum, conjugated estrogens, Cyanocobalamin, darbepoetin alfa, denosumab, Diphtheria and Tetanus Toxoids and Acellular Pertussis Vaccine Adsorbed, Diptheria and Tetanus Toxoids and Acellular Pertussis Vaccine Absorbed, dornase alfa, drotrecogin alfa [activated]), ecallantide, eculizumab, enfuvirtide, enoxaparin sodium, epoetin alfa, etanercept, exenatide, filgrastim, follitropin alfa, follitropin beta, Fragmin, galsulfase, gemtuzumab ozogamicin, glatiramer acetate, Glucagon, golimumab, goserelin acetate, Haemophilus b Conjugate Vaccine—Tetanus Toxoid Conjugate, histrelin acetate, ibritumomab tiuxetan, idursulfase, incobotulinumtoxin A, infliximab, Influenza Virus Vaccine, insulin derivatives, insulin aspart, insulin glargine [rDNA origin], insulin lispro, interferon alfacon-1, interferon beta-1a, Interferon beta-1b, ipilimumab, Japanese Encephalitis Vaccine—Inactivated—Adsorbed, lanreotide acetate, laronidase, leuprolide acetate for depot suspension, leuprolide acetate, linagliptin, liraglutide, mecasermin, menotropins, methoxy polyethylene glycol-epoetin beta, natalizumab, ofatumumab, omalizumab, onabotulinumtoxin A, palivizumab, pancrelipase, pancrelipase, panitumumab, pegaptanib, pegfilgrastim, peginterferon alfa-2a, peginterferon alfa-2b, pegloticase, pegvisomant, pentosan polysulfate sodium, pramlintide, quadrivalent human papillomavirus (types 6, 11, 16, 18) recombinant vaccine, ranibizumab, rasburicase, Recombinant Human Papillomavirus Bivalent (Types 16 and 18) Vaccine, recombinant Interferon alfa-2b, reteplase, Rituximab, romiplostim, sargramostim, secretin, sevelamer carbonate, sevelamer hydrochloride, sipuleucel-T, somatropin, somatropin [rDNA origin], teriparatide, tocilizumab, trastuzumab, triptorelin pamoate, ustekinumab, velaglucerase alfa for injection.

In certain embodiments, the biocompatible hydrogel polymer comprises a protein as a pharmaceutically active biomolecule. Examples of proteins include, but are not limited to, octreotide, eptifibatide, desmopressin, leuprolide/leuprorelin, goserelin, ciclosporin, bivalirudin, glucagon, calcitonin, teriparatide, enfuvirtide, ecallantide, romiplostim. In some embodiments, the biocompatible polymer comprises a recombinant protein as a pharmaceutically active biomolecule. Examples of recombinant proteins include, but are not limited to, insulin, lepirudin, somatropin, aldesleukin, interferon gamma 1b, anakinra, interferon alpha 2b, interferon beta 1b, interferon beta 1a, PEG interferon alpha 2a, filgrastim, pegfilgrastim, oprelvekin, reteplase, denileukin diftitox, follitropin alfa, recFSH, thyrotropin alfa, imiglucerase, becaplermin, sargramostim, darbepoetin, erythropoietin, DNAse, Factor VIIa, Factor IX, Factor XIII, drotrecogin, alteplase, tenecteplase, moroctocog alfa (BDDrFVIII), Factor VIII-2, Factor VIII, peginteferon, ribavarin, clostridial collagenese, alglucosidase alpha2, incobotulinumtoxina, pegloticase, palifermin, galsulfase, idursulfase. In certain embodiments, the biocompatible hydrogel polymer comprises an antibody as a pharmaceutically active biomolecule. Examples of antibodies include, but are not limited to, etanercept, abciximab, gemtuzumab, rituximab, adalimumab, palivizumab, trastuzumab, bevacizumab, natalizumab, omalizumab, infliximab, alemtuzumab, efalizumab, cetuximab, golimumab, abobotulinumtoxina, canakinumab, ustekinumab, ofatumumab, certolizumab pegol, tocilizumab, denosumab, abatacept, ranibizumab, panitumumab, eculizumab, brentixumab, iplimumab, belimumab, rilonacept.

EXAMPLES

The following specific examples are to be construed as merely illustrative, and not limitative of the remainder of the disclosure in any way whatsoever.

The following general characteristics of the monomers and polymers are needed to be successful for bonding the retina without causing any adverse effects.

|   | Monomers Property | Characteristics |
| --- | --- | --- |
| 1 | In vivo polymerizable | Could be polymerized inside mammalian eyes |
| 2 | Reaction mixture pH | Physiological to 8.0 pH range |
| 3 | Reaction temperature | Ambient to body temperature |
| 4 | Formulation physical form | Two or three component system;Mixed immediately prior to use |
| 5 | Mixing time for the reaction to start | Few seconds (~10 sec) |
| 6 | Gel formation time | formation time ranges from 10 seconds to 120 seconds |
| 7 | Solution viscosity | Solution viscosity ranges from 1 to 800 cps |
| 8 | Sterilization capability | ETO to E-beam sterilizable |

-continued

| | Monomers Property | Characteristics |
|---|---|---|
| 9 | Localized delivery | Ideal for localized delivery for small molecules, large molecules and cells |
| Optionally | Stability of drugs in formulation mixture | All small molecule drugs and proteins studied so far, have been found to be stable |

Below are some adhesive polymer characteristics.

| | Adhesive Property | Characteristics |
|---|---|---|
| 1 | Tissue adhesion | Sticky formulations, physicochemical characteristics ideal for bonding to retina |
| 2 | Optical Clarity | Optically clear materials |
| 3 | Polymer hardness | Similar to retina and the surrounding tissues |
| 4 | Bioabsorption Time | About 2 weeks (up to 10 years for drug delivery) |
| 5 | Biocompatibility | Highly biocompatible; passed all the subjected ISO 10993 tests |
| 6 | Polymer cytotoxicity | Non-cytotoxic formulations |
| Optionally | Small molecule elution | Small drug molecules elution can be controlled and thus pharmaceutical drugs could also be delivered using the formulations, if needed |
| Optionally | Compatibility with proteins and Cells | Highly compatible due to physiological pH of the polymers |

For applications on-site, desired gel times are under 120 seconds. Additionally, the viscosity should be high enough to prevent excessive spreading around the target treatment area, but low enough to enter any small cavities at the site. Furthermore, the reaction buffers should be close to physiological conditions. The desired degradation time and polymer pore size will vary based on the application. The polymer should be elastic and strong enough to resist fragmentation in the body.

The chemical components of the polymers are listed in Table 1. The chemical monomers will be referred to by their abbreviations. Several USP grade ophthalmic use approved viscosity enhancing agents were purchased from Sigma-Aldrich and were stored at 25° C. They include methylcellulose (Methocel® MC, 10-25MPA·S) abbreviated as MC; hypromellose (hydroxypropylmethylcellulose 2910) abbreviated as HPMC; and povidone K-30 (polyvinylpyrrolidone) abbreviated as PVP. The monomers were stored at 5° C. and allowed to warm to room temperature before use, which typically took 30 minutes. After use the contents were purged with $N_2$ for approximately 30 seconds before sealing with parafilm and returning to 5° C.

A 0.15 M phosphate buffer was made by dissolving 9.00 g (0.075 mol) $NaH_2PO_4$ in 500 mL of distilled water at 25° C. with magnetic stirring. The pH was then adjusted to 7.99 with the dropwise addition of 50% aqueous NaOH. Several other phosphate buffers were prepared in a similar fashion: 0.10 M phosphate at pH 9, 0.10 M phosphate at pH 7.80, 0.10 M phosphate at 7.72, 0.10 M phosphate at pH 7.46, 0.15 M phosphate at pH 7.94, 0.15 M phosphate at pH 7.90, 0.4 M phosphate at pH 9, and 0.05 M phosphate at pH 7.40.

A sterile 0.10 M phosphate buffer at pH 7.58 with 0.30% HPMC was prepared for use in kits. First, 1.417 g HPMC was dissolved in 471 mL of 0.10 M phosphate buffer at pH 7.58 by vigorous shaking. The viscous solution was allowed to clarify overnight. The solution was filtered through a 0.22 μm filter (Corning #431097) with application of light vacuum. The viscosity of the resulting solution was measured to be 8.48 cSt+/−0.06 at 20° C.

Phosphate buffered saline (PBS) was prepared by dissolving two PBS tablets (Sigma Chemical, P4417) in 400 mL of distilled water at 25° C. with vigorous shaking. The solution has the following composition and pH: 0.01 M phosphate, 0.0027 M potassium chloride, 0.137 M sodium chloride, pH 7.46.

A 0.058 M phosphate buffer was made by dissolving 3.45 g (0.029 mol) of $NaH_2PO_4$ in 500 mL of distilled water at 25° C. with magnetic stirring. The pH was then adjusted to 7.97 with the dropwise addition of 50% aqueous NaOH. A 0.05 M borate buffer was made by dissolving 9.53 g (0.025 mol) of $Na_2B_4O_7 \cdot 10\ H_2O$ in 500 mL of distilled water at 25° C. with magnetic stirring. The pH was then adjusted to 7.93 or 8.35 with the dropwise addition of 6.0 N HCl.

The amine or thiol component (typically in the range of 0.1 mmol arms equivalents) was added to a 50 mL centrifuge tube. A volume of reaction buffer was added to the tube via a pipette such that the final concentration of solids in solution was about 5 percent. The mixture was gently swirled to dissolve the solids before adding the appropriate amount of ester or epoxide. Immediately after adding the ester or epoxide, the entire solution was shaken for 10 seconds before letting it rest.

The gel time for all cases was measured starting from the addition of the ester or epoxide until the gelation of the solution. The gel point was noted by pipetting 1 mL of the reaction mixture and observing the dropwise increase in viscosity. Degradation of the polymers was performed by the addition of 5 to 10 mL of phosphate buffered saline to ca. 5 g of the material in a 50 mL centrifuge tube and incubating the mixture at 37° C. The degradation time was measured starting from the day of addition of the phosphate buffer to complete dissolution of the polymer into solution.

TABLE 1

Components used in formulations.

| Components | Technical Name |
|---|---|
| ETTMP-1300 | Ethoxylated trimethylolpropane tri(3-mercaptopropionate) |
| 4ARM-5k-SH | 4ARM PEG Thiol (pentaerythritol) |
| 4ARM-2k-NH2 | 4ARM PEG Amine (pentaerythritol), HCl Salt, MW 2000 |
| 4ARM-5k-NH2 | 4ARM PEG Amine (pentaerythritol), HCl Salt, MW 5000 |
| 8ARM-20k-NH2 | 8ARM PEG Amine (hexaglycerol), HCl Salt, MW 20000 |
| 4ARM-20k-AA | 4ARM PEG Acetate Amine HCl Salt, MW 20000 |
| 8ARM-20k-AA | 8ARM PEG Acetate Amine (hexaglycerol) HCl Salt, MW 20000 |
| 8ARM-20k-AA | 8ARM PEG Acetate Amine (hexaglycerol) TFA Salt, MW 20000 |
| 4ARM-10k-SG | 4ARM PEG Succinimidyl Glutarate (pentaerythritol), MW 10000 |
| 8ARM-15k-SG | 8ARM PEG Succinimidyl Glutarate (hexaglycerol), MW 15000 |
| 4ARM-20k-SGA | 4ARM PEG Succinimidyl Glutaramide (pentaerythritol), MW 20000 |
| 4ARM-10k-SS | 4ARM PEG Succinimidyl Succinate (pentaerythritol), MW 10000 |
| EJ-190 | Sorbitol polyglycidyl ether |
| MC | Methyl Cellulose (Methocel ® MC) |
| HPMC | Hypromellose (Hydroxypropylmethylcellulose) |
| PVP | Povidone (polyvinylpyrrolidone) |

Example 1: Manufacture of Hydrogel (Amine-Ester Chemistry)

A solution of 8ARM-20K-NH2 was prepared in a Falcon tube by dissolving about 0.13 g solid monomer in about 2.5 mL of sodium phosphate buffer (buffer pH 7.36). The mixture was shaken for about 10 seconds at ambient temperature until complete dissolution was obtained. The Falcon tube was allowed to stand at ambient temperature. In another Falcon tube, 0.10 g of 8ARM-15K-SG was dissolved in the same phosphate buffer as above. The mixture was shaken for about 10 seconds and at this point all the powder dissolved. The 8ARM-15K-SG solution was poured immediately into the 8ARM-20K-NH2 solution and a timer was started. The mixture was shaken and mixed for about 10 seconds and a 1 mL solution of the mixture was pipetted out using a mechanical high precision pipette. The gel time of 1 mL liquid was collected and then verified with the lack of flow for the remaining liquids. The gel time data of the formulation was recorded and was about 90 seconds.

Example 2: Manufacture of Hydrogel (Amine-Ester Chemistry)

A solution of amines was prepared in a Falcon tube by dissolving about 0.4 g solid 4ARM-20k-AA and about 0.2 g solid 8ARM-20k-NH2 in about 18 mL of sodium phosphate buffer (buffer pH 7.36). The mixture was shaken for about 10 seconds at ambient temperature until complete dissolution was obtained. The Falcon tube was allowed to stand at ambient temperature. To this solution, 0.3 g of 8ARM-15K-SG was added. The mixture was shaken to mix for about 10 seconds until all the powder dissolved. 1 mL of the mixture was pipetted out using a mechanical high precision pipette. The gel time of the formulation was collected using the process described above. The gel time was about 90 seconds.

Example 3: Manufacture of Hydrogel (Thiol-Ester Chemistry

A solution of ETTMP-1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.20 g of 8ARM-15K-SG was added. The mixture was shaken for about 10 seconds until the powder dissolved. 1 mL of the mixture was pipetted out using a mechanical high precision pipette. The gel time was found to be about 70 seconds.

Example 4: Manufacture of Hydrogel (Thiol-Epoxide Chemistry)

A solution of ETTMP-1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.10 g of EJ-190 was added. The mixture was shaken for about 10 seconds until complete dissolution is obtained. 1 mL of the mixture was pipetted out using a mechanical high precision pipette. The gel time was found to be about 6 minutes.

Example 5: In Vitro Bioabsorbance Testing

A 0.10 molar buffer solution of pH 7.40 was prepared with deionized water. A 50 mL portion of this solution was transferred to a Falcon tube. A sample polymer was prepared in a 20 cc syringe. After curing, a 2-4 mm thick slice was cut from the polymer slug and was placed in the Falcon tube. A circulating water bath was prepared and maintained at 37° C. The Falcon tube with polymer was placed inside the water bath and time was started. The dissolution of the polymer was monitored and recorded. The dissolution time ranged from 1-90 days depending on the type of sample polymer.

Example 6: Gelling and Degradation Times of Amine-Ester Polymers

Amines studied were 8ARM-20k-NH2 and 4ARM-5k-NH2. The formulation details and material properties are given in Table 2. With 8ARM-20k-NH2, it was found that a phosphate buffer with 0.058 M phosphate and pH of 7.97 was necessary to obtain acceptable gel times of around 100 seconds. Using a 0.05 M phosphate buffer with a pH of 7.41 resulted in a more than two-fold increase in gel time (270 seconds).

With the 8ARM-20k-NH2, the ratio of 4ARM-10k-SS to 4ARM-20k-SGA was varied from 50:50 to 90:10. The gel time remained consistent, but there was a marked shift in degradation time around a ratio of 80:20. For formulations with ratios of 75:25 and 50:50, degradation times spiked to one month and beyond. Using lower amounts of 4ARM-20k-SGA (80:20, 85:15, 90:10) resulted in degradation times of less than 7 days.

As a comparison, the 4ARM-5k-NH2 was used in a formulation with a ratio of 4ARM-10k-SS to 4ARM-20k-SGA of 80:20. As was expected, the degradation time remained consistent, which suggests that the mechanism of degradation was unaffected by the change in amine. However, the gel time increased by 60 seconds, which may reflect the relative accessibility of reactive groups in a high molecular weight 8ARM amine and a low molecular weight 4ARM amine.

Table 3. It was found that a 0.05 M borate buffer with a pH of 7.93 produced gel times of around 120 seconds. Increasing the amount of 4ARM-20k-SGA in the formulation increased the gel time to 190 seconds (25:75 ratio of 4ARM-10k-SS to 4ARM-20k-SGA) up to 390 seconds (0:100 ratio of 4ARM-10k-SS to 4ARM-20k-SGA). Using a 0.05 M borate buffer with a pH of 8.35 resulted in a gel time of 65 seconds, about a two-fold decrease in gel time. Thus, the gel time may be tailored by simply adjusting the pH of the reaction buffer.

TABLE 2

Gel and degradation times for varying 4ARM-10k-SS/4ARM-20k-SGA ratios with 8ARM-15k-SG ester.

| Components | Ratio of 4ARM-10k-SS/ 4ARM-20k-SGA | Phosphate Reaction Buffer Concentration and pH | Gel Time (s) | Degradation Time (days) |
|---|---|---|---|---|
| 8ARM-20k-NH2 4ARM-10k-SS, 4ARM-20k-SGA | 50/50 | 0.05M pH 7.41 | 270 | N/A |
| 8ARM-20k-NH2 4ARM-10k-SS, 4ARM-20k-SGA | 50/50 | 0.058M pH 7.97 | 100 | >41 |
| 8ARM-20k-NH2 4ARM-10k-SS, 4ARM-20k-SGA | 75/25 | 0.058M pH 7.97 | 90 | 29 |
| 8ARM-20k-NH2 4ARM-10k-SS, 4ARM-20k-SGA | 80/20 | 0.058M pH 7.97 | 100 | 7 |
| 4ARM-5k-NH2 4ARM-10k-SS, 4ARM-20k-SGA | 80/20 | 0.058M pH 7.97 | 160 | 6 |
| 8ARM-20k-NH2 4ARM-10k-SS, 4ARM-20k-SGA | 85/15 | 0.058M pH 7.97 | 100 | 5 |
| 8ARM-20k-NH2 4ARM-10k-SS, 4ARM-20k-SGA | 90/10 | 0.058M pH 7.97 | 90 | 6 |

Example 7: Gelling and Degradation Times of Thiol-Ester Polymers

Thiols studied were 4ARM-5k-SH and ETTMP-1300. The formulation details and material properties are given in Table 3.

The ratio of 4ARM-10k-SS to 4ARM-20k-SGA was varied from 0:100 to 100:0. In all cases, the degradation time did not vary significantly and was typically between 3 and 5 days. It is likely that degradation is occurring via alternate pathways.

TABLE 3

Gel and degradation times for varying 4ARM-10k-SS/4ARM-20k-SGA ratios with 4ARM-5k-SH and ETTMP-1300 thiols.

| Components | Ratio of 4ARM-10k-SS/ 4ARM-20k-SGA | Phosphate Reaction Buffer Concentration and pH | Gel Time (s) | Degradation Time (days) |
|---|---|---|---|---|
| 4ARM-5k-SH 4ARM-10k-SS, 4ARM-20k-S GA | 50/50 | 0.05M pH 8.35 | 65 | N/A |
| 4ARM-5k-SH 4ARM-10k-SS, 4ARM-20k-S GA | 50/50 | 0.05M pH 7.93 | 120 | 4 |
| 4ARM-5k-SH 4ARM-10k-SS, 4ARM-20k-S GA | 75/25 | 0.05M pH 7.93 | 125 | 4 |
| 4ARM-5k-SH 4ARM-10k-SS, 4ARM-20k-S GA | 90/10 | 0.05M pH 7.93 | 115 | 4 |
| 4ARM-5k-SH 4ARM-10k-SS, 4ARM-20k-S GA | 25/75 | 0.05M pH 7.93 | 190 | 4 |
| 4ARM-5k-SH 4ARM-10k-SS, 4ARM-20k-S GA | 10/90 | 0.05M pH 7.93 | 200 | 4 |
| ETTMP-1300 4ARM-20k-SGA | 0/100 | 0.05M | 390 | 3 |
| 4ARM-5k-SH 4ARM-10k-SS | 100/0 | 0.05M pH 7.93 | 120 | 4 |

Example 8: Gelling and Degradation Times of Amine-Ester and Thiol-Ester Polymers An amine (4ARM-5k-NH2) and a thiol (4ARM-5k-SH) were studied with the ester 4ARM-10k-SG. The formulation details and material properties are given in Table 4. A 0.058 M phosphate buffer with a pH of 7.97 yielded a gel time of 150 seconds with the amine. A 0.05 M borate buffer with a pH of 8.35 produced a gel time of 75 seconds with the thiol.

The amine-based polymer appeared to show no signs of degradation, as was expected from the lack of degradable groups. However, the thiol-based polymer degraded in 5 days. This suggests that degradation is occurring through alternate pathways, as was observed in the thiol formulations with 4ARM-10k-SS and 4ARM-20k-SGA (vida supra).

TABLE 4

Gel and degradation times for amines and thiols with 4ARM-10k-SG formulations.

| Components | Reaction Buffer Type, Concentration, and pH | Gel Time (s) | Degradation Time (days) |
|---|---|---|---|
| 4ARM-5k-NH2 & 4ARM-10k-SG | Phosphate (0.058M, pH 7.97) | 150 | Indefinite |
| 4ARM-5k-SH & 4ARM-10k-SG | Borate (0.05M, pH 8.35) | 75 | 5 |

Example 9: Gelling and Degradation Times of Thiol-Sorbitol Polyglycidyl Ether Polymers With ETTMP-1300 conditions such as high pH (10), high solution concentration (50%), or high borate concentration (0.16 M) were necessary for the mixture to gel. Gel times ranged from around 30 minutes to many hours. The conditions that were explored include: pH from 7 to 12; solution concentration from 5% to 50%; borate concentration from 0.05 M to 0.16 M; and thiol to epoxide ratios from 1:2 to 2:1.

The high pH necessary for the reaction to occur could result in degradation of the thiol. Thus, a polymer with EJ-190 and 4ARM-5k-SH was prepared. A 13% solution formulation exhibited a gel time of 230 seconds at a pH of between 9 and 10. The degradation time was 32 days. At a lower pH of around 8, the mixture exhibited gel times in the range of 1 to 2 hours.

Example 10: General Procedure for the Preparation of In Vivo Polymerizable Materials Several representative sticky formulations are listed in Table 5 along with specific reaction details for the preparation of in vivo polymerizable materials. The polymers were prepared by first dissolving the amine component in phosphate buffer or the thiol component in borate buffer. The appropriate amount of the ester component was then added and the entire solution was mixed vigorously for 10 to 20 seconds. The gel time was measured starting from the addition of the ester until the gelation of the solution.

TABLE 5

| (A) | | | | | |
|---|---|---|---|---|---|
| Components | Amine or Thiol/Ester Molar Ratio | Buffer | % Solution | Gel Time (s) | Degradation Time (days) |
| 8ARM-20k-NH2 4ARM-20K-SGA | 3 | 0.15M phosphate, pH 7.99 | 3 | 130 | N/A |
| 8ARM-20k-NH2 4ARM-20K-SGA | 1/3 | 0.15M phosphate, pH 7.99 | 3 | 300 | N/A |
| 8ARM-20k-NH2 4ARM-10K-SS | 3 | 0.15M phosphate, pH 7.99 | 8 | 50 | N/A |
| 8ARM-20k-NH2 4ARM-10K-SS | 1/3 | 0.15M phosphate, pH 7.99 | 8 | 80 | N/A |
| 4ARM-20K-AA/ 8ARM-20k-NH2 (75/25) 4ARM-20K-SGA | 3 | 0.15M phosphate, pH 7.99 | 5 | 210 | 1 to 3 |
| 4ARM-20K-AA/ 8ARM-20k-NH2 (75/25) 4ARM-20K-SGA | 5 | 0.15M phosphate, pH 7.99 | 10 | 180 | 1 to 3 |
| 4ARM-5K-NH2 4ARM-10K-SG | 5 | 0.10M phosphate, pH 7.80 | 10 | 160 | 7 |
| 4ARM-5K-NH2 4ARM-10K-SS | 5 | 0.10M phosphate, pH 7.80 | 20 | 160 | 1 to 3 |
| 4ARM-5K-NH2 4ARM-10K-SG | 3 | 0.10M phosphate, pH 7.80 | 5 | 160 | 13 |
| 4ARM-5K-NH2 4ARM-10K-SG | 5 | 0.15M phosphate, pH 7.99 | 20 | 80 | 7 |
| 4ARM-5K-NH2 4ARM-10K-SG | 5 | 0.15M phosphate, pH 7.99 | 30 | 70 | 10 |

TABLE 5-continued

| | | | | | |
|---|---|---|---|---|---|
| 4ARM-5K-NH2 4ARM-20K-SGA | 5 | 0.15M phosphate, pH 7.99 | 19 | 60 | 53 |
| 4ARM-5K-NH2 4ARM-20K-SGA | 5 | 0.15M phosphate, pH 7.99 | 12 | 70 | 53 |
| 4ARM-5K-NH2 4ARM-10K-SG | 1/5 | 0.15M phosphate, pH 7.99 | 19 | 160 | 15 |
| 4ARM-SH-5K 4ARM-10K-SG | 5 | 0.05M borate, pH 7.93 | 20 | 120 | 2 to 4 |
| 4ARM-NH2-2K 8ARM-15K-SG | 5 | 0.10M phosphate, pH 7.46 | 10 | 120 | 15 |
| 4ARM-NH2-2K 4ARM-20K-SGA | 7 | 0.10M phosphate, pH 7.80 | 30 | 150 | N/A |

(B)

| Components | MW | Mmoles | Wt (g) | Arm | mmoles | Arms Eq | Polymer % Solution (w/v) |
|---|---|---|---|---|---|---|---|
| 8ARM-20k-NH2 | 20000 | 1000 | 0.075 | 8 | 0.00375 | 0.03 | |
| 4ARM-20k-SGA | 20000 | 1000 | 0.05 | 4 | 0.0025 | 0.01 | |
| Buffer Volume (phosphate) | | | 4.1 | | | | 3.0 |
| 8ARM-20k-NH2 | 20000 | 1000 | 0.025 | 8 | 0.00125 | 0.01 | |
| 4ARM-20k-SGA | 20000 | 1000 | 0.15 | 4 | 0.0075 | 0.03 | |
| Buffer Volume (phosphate) | | | 5.8 | | | | 3.0 |
| 8ARM-20k-NH2 | 20000 | 1000 | 0.3 | 8 | 0.015 | 0.12 | |
| 4ARM-10k-SS | 10000 | 1000 | 0.1 | 4 | 0.01 | 0.04 | |
| Buffer Volume (phosphate) | | | 5 | | | | 8.0 |
| 8ARM-20k-NH2 | 20000 | 1000 | 0.1 | 8 | 0.005 | 0.04 | |
| 4ARM-10k-SS | 10000 | 1000 | 0.3 | 4 | 0.03 | 0.12 | |
| Buffer Volume (phosphate) | | | 5 | | | | 8.0 |

(A) Summary of the reaction details for several representative sticky formulations without viscosity enhancer;
(B) more detailed tabulation of a selection of the reaction details including moles (degradation times were measured in phosphate buffered saline (PBS) at 37° C.).

TABLE 6

Gel times for the 8ARM-20k-NH2/4ARM-20k-SGA(1/1) sticky polymers including HPMC as viscosity enhancer with varying buffers and concentrations.

| Components | Amine/Ester Molar Ratio | Buffer | % Solution | Gel Time (min) |
|---|---|---|---|---|
| 8ARM-20k-NH2 4ARM-20K-SGA 0.3% HPMC | 1 | 0.10M phosphate, pH 7.80 | 4.8 | 1.5 |
| 8ARM-20k-NH2 4ARM-20K-SGA 0.3% HPMC | 1 | 0.10M phosphate, pH 7.46 | 4.8 | 3.5 |
| 8ARM-20k-NH2 4ARM-20K-SGA 0.3% HPMC | 1 | 0.05M phosphate, pH 7.42 | 4.8 | 4.5 |
| 8ARM-20k-NH2 4ARM-20K-SGA 0.3% HPMC | 1 | 0.05M phosphate, pH 7.42 | 4 | 5.5 |
| 8ARM-20k-NH2 4ARM-20K-SGA 0.3% HPMC | 1 | 0.05M phosphate, pH 7.42 | 3 | 8.5 |
| 8ARM-20k-NH2 4ARM-20K-SGA 0.3% HPMC | 1 | 0.05M phosphate, pH 7.24 | 4.8 | 6.75 |
| 8ARM-20k-NH2 4ARM-20K-SGA 0.3% HPMC | 1 | 0.05M phosphate, pH 7.24 | 3 | 12 |
| 8ARM-20k-NH2 4ARM-20K-SGA 0.3% HPMC | 1 | 0.05M phosphate, pH 7.24 | 2.5 | 15.5 |

Gel times ranged from 60 to 300 seconds and were found to be easily tuned by adjusting the reaction buffer pH, buffer concentration, or polymer concentration. An example of gel time control for a single formulation is shown in Table 6, where the gel time for the 8ARM-20k-NH2/4ARM-20k-SGA (1/1) polymer was varied from 1.5 to 15.5 minutes.

In some instances, the stickiness of the polymers originates from a mismatching in the molar equivalents of the components. A variety of sticky materials using combinations of 4 or 8 armed amines of molecular weights between 2 and 20 thousand and 4 or 8 armed esters of molecular weights between 10 and 20 thousand were created. It was found that in comparison with the 8 armed esters, the 4 armed esters resulted in stickier materials. For the amine component, it was found that smaller molecular weights led to stickier materials and higher amine to ester molar ratios.

A mismatch (amine to ester molar ratio) of at least 3 was required to qualitatively sense stickiness. More preferably, a ratio of around 5 produced a desirable level of stickiness combined with polymer strength. Polymers with amine to ester molar ratios higher than 5 may be formed as well, but some reaction conditions, such as the polymer concentration, may need to be adjusted to obtain a reasonable gel time. Furthermore, it was found that the use of a viscosity enhanced solution improves the polymers by increasing their strength and elasticity, allowing for higher amine to ester molar ratios (Example 11, Table 8).

The materials formed were typically transparent and elastic. Stickiness was tested for qualitatively by touch. Thus, a sticky material adhered to a human finger or other surface and remained in place until removed. Degradation times varied from 1 to 53 days. In certain instances, he polymer properties, such as gel and degradation times, pore sizes, swelling, etc. may be optimized for different applications without losing the stickiness.

Example 11: General Procedure for the Preparation of Solutions with Enhanced Viscosity Polymer solutions with enhanced viscosities were prepared by the addition of a viscosity enhancing agent to the reaction buffer. Table 8B lists the viscosity enhancing agents studied, including observations on the properties of the formed polymers. Stock solutions of reaction buffers were prepared with varying concentrations of methylcellulose (MC), hypromellose (HPMC) or polyvinylpyrrolidone (PVP). As an example, a 2% (w/w) HPMC solution in buffer was made by adding 0.2 g of HPMC to 9.8 mL of 0.10 M phosphate buffer at pH 7.80, followed by vigorous shaking. The solution was allowed to stand overnight. Buffer solutions with HPMC concentrations ranging from 0.01% to 2.0% were prepared in a similar fashion. Buffer solutions with PVP concentrations ranging from 5% to 20% and buffer solutions with MC concentrations ranging from 1.0 to 2.0% were also prepared by a similar method.

The polymers were formed in the same method as described above in the general procedures for the preparation of the sticky materials (Example 10). A typical procedure involved first dissolving the amine component in the phosphate buffer containing the desired concentration of viscosity enhancing agent. The appropriate amount of the ester component was then added and the entire solution was mixed vigorously for 10 to 20 seconds. The gel time was measured starting from the addition of the ester until the gelation of the solution.

Several representative formulations are listed in Table 7 along with specific reaction details. The percent of degradable acetate amine component by mole equivalents is represented by a ratio designated in parenthesis. For example, a formulation with 75% degradable amine will be written as 8ARM-20k-AA/8ARM-20k-NH2 (75/25). The polymer was prepared by first dissolving the amine component in phosphate buffer. The appropriate amount of the ester component was then added and the entire solution was mixed vigorously for 10 to 20 seconds. The gel time was measured starting from the addition of the ester until the gelation of the solution.

The gel time is dependent on several factors: pH, buffer concentration, polymer concentration, temperature and the monomers used. Previous experiments have shown that the extent of mixing has little effect on the gel time once the components are in solution, which typically takes up to 10 seconds. FIG. 1 shows the effect of monomer addition on buffer pH. For the 8ARM-20k-NH2 & 4ARM-20k-SGA formulation, the buffer pH drops slightly from 7.42 to 7.36 upon addition of the monomers. For the 8ARM-20k-AA/ 8ARM-20k-NH2 (70/30) & 4ARM-20k-SGA formulation, the buffer pH drops from 7.4 to 7.29 upon addition of the monomers. The additional decrease in the pH was found to originate from acidic residues in the degradable acetate amine. The same pH drop phenomenon was observed for the 4ARM-20k-AA amine. In certain instances, a quality control specification on the acetate amine solution pH may be required to improve the consistency of degradable formulations.

Figure 2:
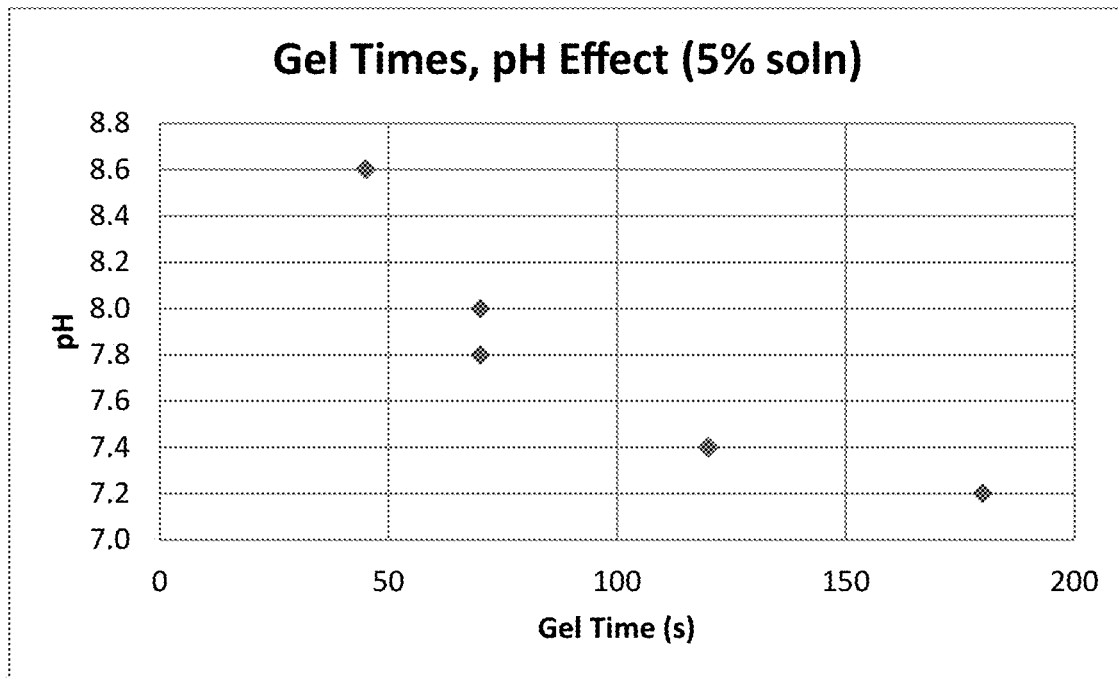
FIG. 2 shows the effect of reaction buffer pH on gel times for 8ARM-20k-NH2 & 8ARM-15k-SG polymer formulation at 5% solution using 0.05 M phosphate buffer.
Figure 3:
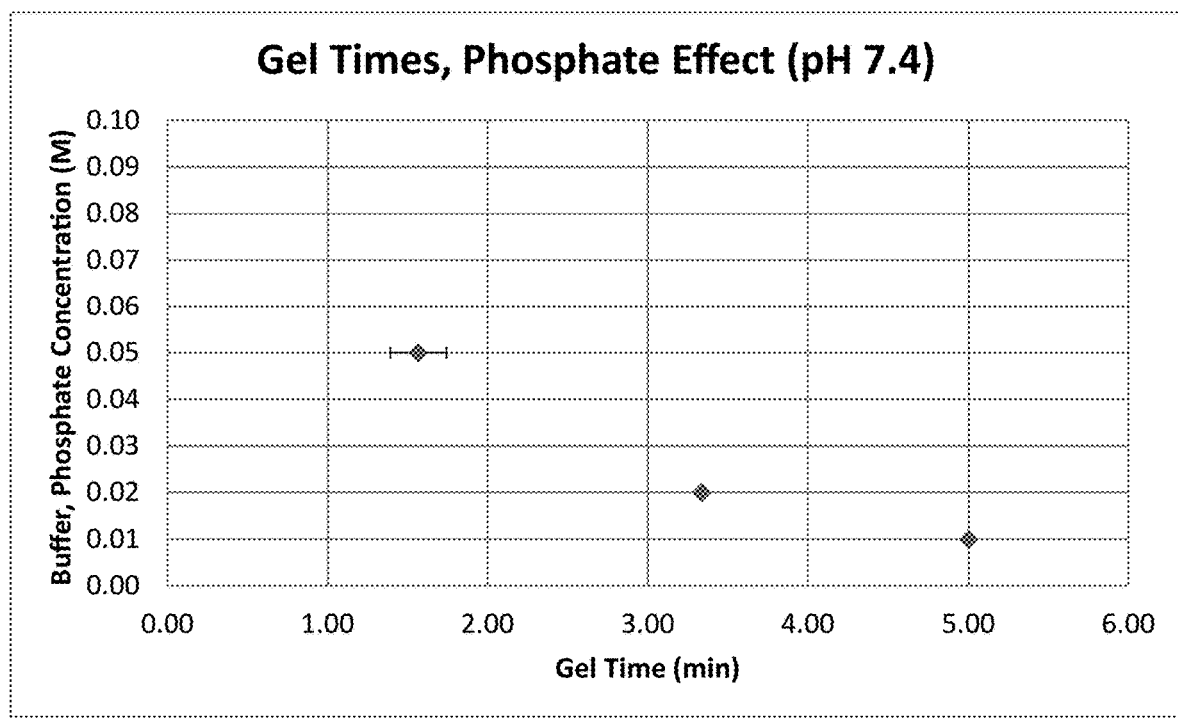
FIG. 3 shows the effect of reaction buffer phosphate concentration on gel times for 8ARM-20k-NH2 & 8ARM-15k-SG polymer formulation at 5% solution using phosphate buffer at pH 7.4.
Figure 4:
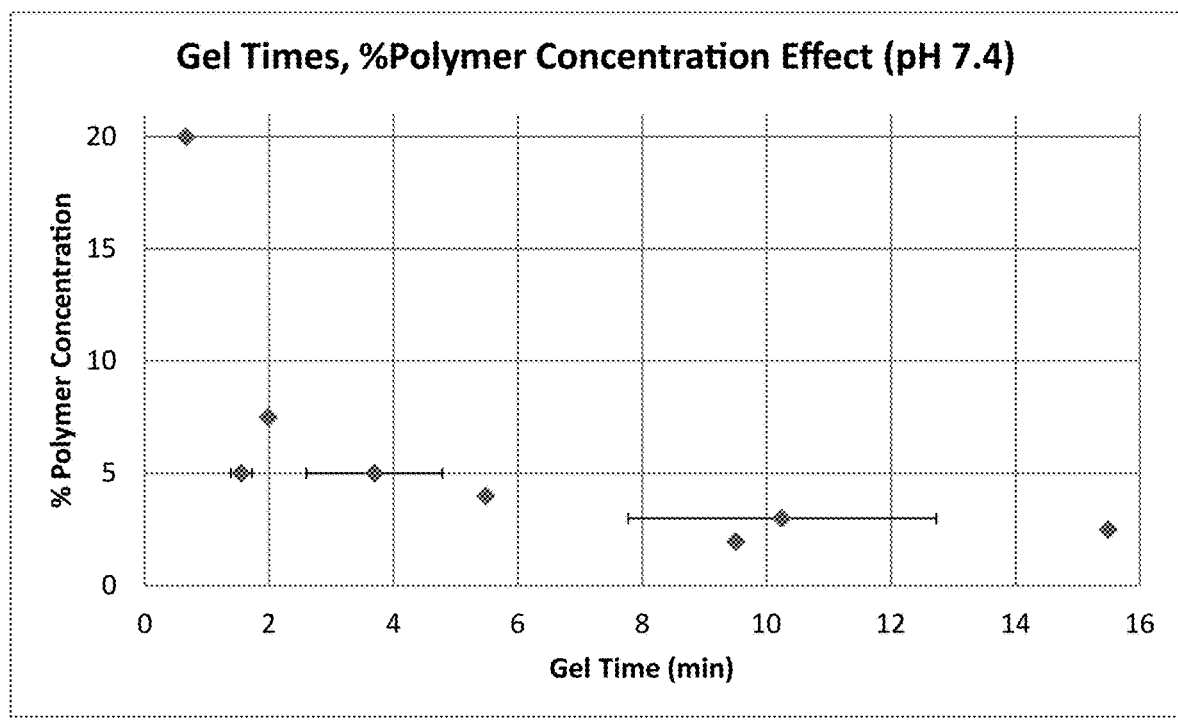
FIG. 4 shows the effect of polymer concentration on gel times using a 0.05 M phosphate buffer at pH 7.4.
Figure 5:
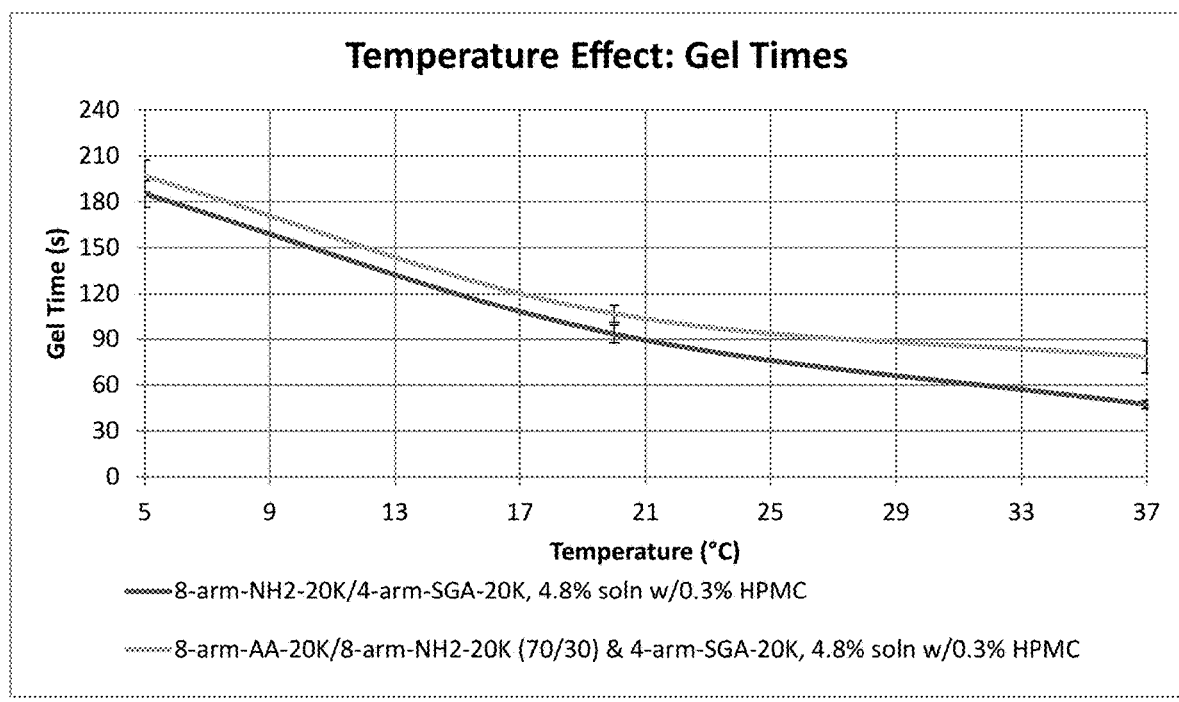
FIG. 5 shows the effect of temperature on gel times for two formulations: 1) 8ARM-20k-NH2 & 4ARM-20k-SGA at 4.8% solution with 0.3% HPMC; 2) 8ARM-20k-AA/8ARM-20k-NH2 (70/30) & 4ARM-20k-SGA at 4.8% solution with 0.3% HPMC.

FIG. 2 depicts the effect of reaction buffer pH on gel times. The gel times increase with an increase in the concentration of hydronium ions in an approximately linear fashion. More generally, the gel times decrease with an increase in the buffer pH. FIG. 3 shows the effect of reaction buffer phosphate concentration on gel times. The gel times decrease with an increase in the phosphate concentration. FIG. 4 illustrates the effect of polymer concentration on gel times. The gel times decrease significantly with an increase in the polymer concentration. At low polymer concentrations where the gel time is greater than 5 minutes, hydrolysis reactions of the ester begin to compete with the formation of the polymer. The effect of temperature on gel times appears to follow the Arrhenius equation, as seen in FIG. 5. The gel time is directly related to the extent of reaction of the polymer solution and so this behavior is not unusual.

Figure 6:
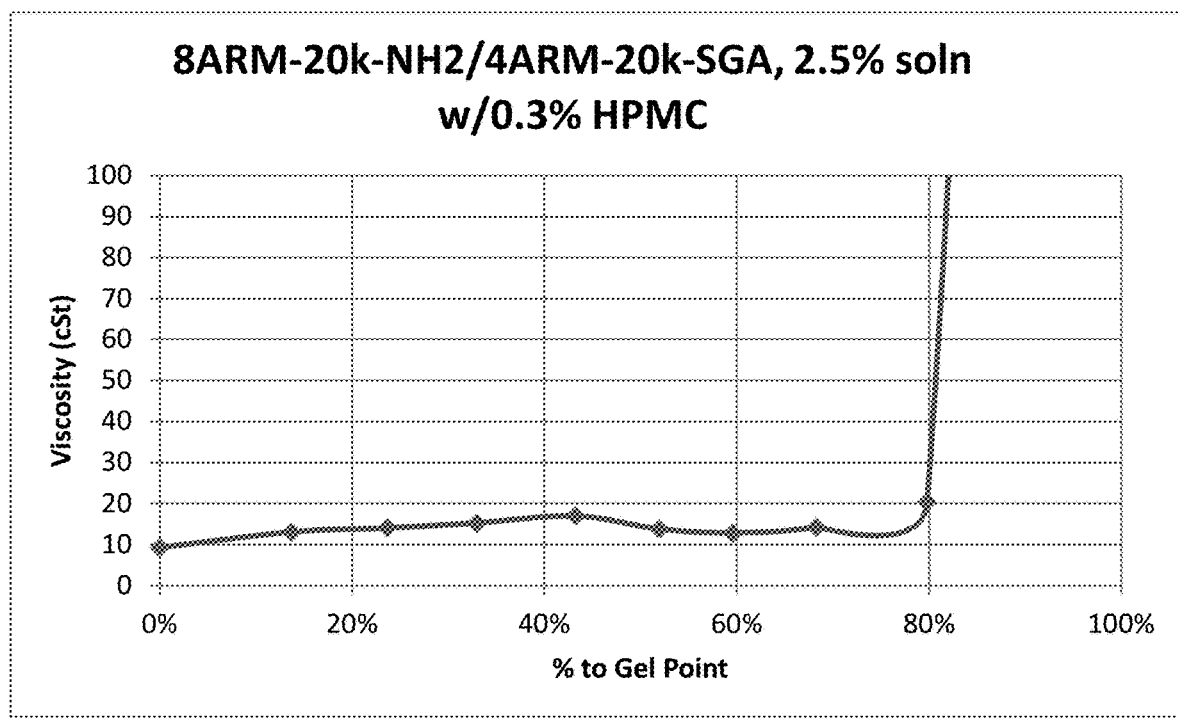
FIG. 6 shows the viscosity of the polymer solution up to the gel point as a function of the % of time to the gel point.

In FIG. 6, the rheology of the polymers during the gelation process is shown as a function of the percent time to the gel point. Thus, 100% represents the gel point and 50% represents half the time before the gel point. The viscosity of the reacting solution remains relatively constant until about 80% of the gel point. After that point, the viscosity increases dramatically, representing the formation of the solid gel.

Figure 7:
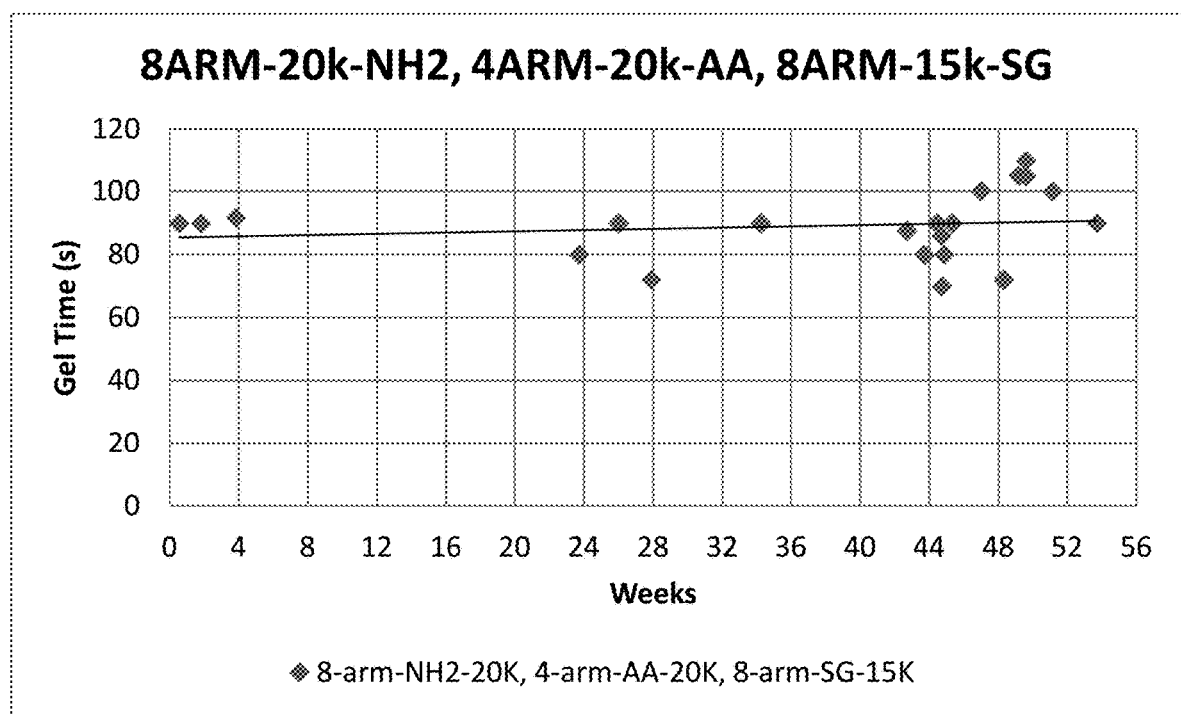
FIG. 7 shows the bulk monomer stability over approximately 56 weeks for the formulation involving 8ARM-20k-NH2, 4ARM-20k-AA, and 8ARM-15k-SG at an amine to ester molar ratio of 1 to 1. The % solution of polymer was 5%±0.5%. Different reaction buffers were used over time, but the composition was typically 0.058 M phosphate at a pH of 7.4±0.1.

FIG. 7 shows the gel time stability of a single formulation using the same lot of monomers over the course of about a year. The monomers were handled according to the standard protocol outlined above. The gel times remained relatively stable; some variations in the reaction buffer may account for differences in the gel times.

TABLE 7

(A)

| Components | Buffer | % Solution | Gel Time (s) | Degradation Time (days) |
|---|---|---|---|---|
| 4ARM-20k-AA/8ARM-20k-NH2 (60/40) 4ARM-20k-SGA | 0.10M phosphate, pH 7.80 | 5 | 150 | 21 |
| 4ARM-20k-AA/8ARM-20k-NH2 (60/40) 4ARM-20k-SGA 0.3% HPMC | 0.10M phosphate, pH 7.80 | 5 | 150 | 21 |

TABLE 7-continued

| Composition | Buffer | Col 3 | Col 4 | Col 5 |
|---|---|---|---|---|
| 8ARM-20k-NH2<br>4ARM-20k-SGA<br>0.3% HPMC | 0.10M phosphate, pH 7.80 | 4.8 | 100 | N/A |
| 8ARM-20k-NH2<br>8ARM-15k-SG<br>0.3% HPMC | 0.10M phosphate, pH 7.80 | 4.8 | 70 | 48 |
| 4ARM-20k-AA/8ARM-20k-NH2 (60/40)<br>8ARM-15k-SG<br>0.3% HPMC | 0.10M phosphate, pH 7.80 | 4.8 | 110 | 12 |
| 4ARM-20k-AA/8ARM-20k-NH2 (60/40)<br>4ARM-20k-SGA<br>0.3% HPMC | 0.10M phosphate, pH 7.80 | 20 | 160 | 21 |
| 8ARM-20k-NH2<br>4ARM-20k-SGA | 0.10M phosphate, pH 7.80 | 4.8 | 90 | N/A |
| 8ARM-20k-NH2<br>4ARM-20k-SGA<br>1.0% HPMC | 0.10M phosphate, pH 7.80 | 4.8 | 80 | N/A |
| 8ARM-20k-NH2<br>4ARM-20k-SGA<br>0.3% HPMC | 0.10M phosphate, pH 7.46 | 4.8 | 210 | N/A |
| 8ARM-20k-NH2<br>4ARM-20k-SGA<br>0.3% HPMC | 0.05M phosphate, pH 7.42 | 4.8 | 270 | N/A |
| 8ARM-20k-NH2<br>4ARM-20k-SGA<br>0.3% HPMC | 0.05M phosphate, pH 7.42 | 4 | 330 | N/A |
| 8ARM-20k-NH2<br>4ARM-20k-SGA<br>pH 7.42<br>0.3% HPMC | 0.05M phosphate, | 3 | 510 | N/A |
| 8ARM-20k-NH2<br>4ARM-20k-SGA<br>0.3% HPMC | 0.05M phosphate, pH 7.24 | 4.8 | 405 | N/A |
| 8ARM-20k-NH2<br>4ARM-20k-SGA<br>0.3% HPMC | 0.05M phosphate, pH 7.24 | 3 | 720 | N/A |
| 8ARM-20k-NH2<br>4ARM-20k-SGA<br>0.3% HPMC | 0.05M phosphate, pH 7.24 | 2.5 | 930 | N/A |
| 8ARM-20k-AA<br>4ARM-20k-SGA<br>HPMC (0.3%) | 0.10M phosphate, pH 7.46 | 4.8 | 90 | 6 |
| 8ARM-20k-AA/8ARM-20k-NH2 (75/25)<br>4ARM-20k-SGA<br>HPMC (0.3%) | 0.10M phosphate, pH 7.46 | 4.8 | 100 | 16 |
| 8ARM-20k-AA/8ARM-20k-NH2 (60/40)<br>4ARM-20k-SGA<br>HPMC (0.3%) | 0.10M phosphate, pH 7.46 | 4.8 | 95 | 256 (estimated) |
| 8ARM-20k-AA/8ARM-20k-NH2 (50/50)<br>4ARM-20k-SGA<br>HPMC (0.3%) | 0.10M phosphate, pH 7.46 | 4.8 | 120 | N/A |
| 8ARM-20k-AA/8ARM-20k-NH2 (70/30)<br>4ARM-20k-SGA<br>HPMC (0.3%) | 0.10M phosphate, pH 7.46 | 4.8 | 100 | 21 |
| 8ARM-20k-AA/8ARM-20k-NH2 (65/35)<br>4ARM-20k-SGA<br>HPMC (0.3%) | 0.10M phosphate, pH 7.46 | 4.8 | 100 | 28 |
| 8ARM-20k-NH2<br>4ARM-20k-SGA<br>1.5% HPMC | 0.10M phosphate, pH 7.80 | 4.8 | 90 | N/A |
| 8ARM-20k-AA/8ARM-20k-NH2 (75/25)<br>4ARM-20k-SGA<br>HPMC (0.3%) | 0.10M phosphate, pH 7.46 | 4.8 | 90 | 16 |
| 8ARM-20k-AA/8ARM-20k-NH2 (70/30)<br>4ARM-20k-SGA<br>HPMC (0.3%) | 0.10M phosphate, pH 7.46 | 4.8 | 105 | 21 |
| 8ARM-20k-AA/8ARM-20k-NH2 (50/50)<br>4ARM-20k-SGA<br>HPMC (0.3%) | 0.10M phosphate, pH 7.46 | 4.8 | 120 | N/A |

TABLE 7-continued

| | | | | |
|---|---|---|---|---|
| 8ARM-20k-AA/8ARM-20k-NH2 (70/30) 8ARM-15k-SG HPMC (0.3%) | 0.10M phosphate, pH 7.46 | 4.8 | 70 | 7 |
| 4ARM-20k-AA/8ARM-20k-NH2 (70/30) 4ARM-20k-SGA HPMC (0.3%) | 0.10M phosphate, pH 7.46 | 4.8 | 260 | 10 |
| 8ARM-20k-AA/8ARM-20k-NH2 (60/40) 8ARM-15k-SG HPMC (0.3%) | 0.10M phosphate, pH 7.46 | 4.8 | 70 | 17 |
| 8ARM-20k-AA 4ARM-20k-SGA HPMC (0.3%) | 0.10M phosphate, pH 7.46 | 4.8 | 85 | 7 |
| 8ARM-20k-AA/8ARM-20k-NH2 (70/30) 4ARM-20k-SGA HPMC (0.3%) | 0.10M phosphate, pH 7.46 | 4.8 | 95 | 13 |
| 8ARM-20k-AA/8ARM-20k-NH2 (75/25) 4ARM-20k-SGA HPMC (0.3%) | 0.10M phosphate, pH 7.46 | 4.8 | 95 | 10 |
| 8ARM-20k-AA/8ARM-20k-NH2 (75/25) 4ARM-20k-SGA HPMC (0.3%) | 0.10M phosphate, pH 7.58 | 4 | 110 | 10 |
| 8ARM-20k-AA/8ARM-20k-NH2 (75/25) 4ARM-20k-SGA HPMC (0.3%) | 0.10M phosphate, pH 7.58 | 3.5 | 150 | 9 |
| 8ARM-20k-AA/8ARM-20k-NH2 (75/25) 4ARM-20k-SGA HPMC (0.3%) | 0.10M phosphate, pH 7.58 | 3 | 190 | 8 |

(B)

| Components | MW | Mmoles | Wt (g) | Arm | mmoles | Arms Eq | Polymer % Solution (w/v) |
|---|---|---|---|---|---|---|---|
| 8ARM-20k-NH2 | 20000 | 1000 | 0.04 | 8 | 0.002 | 0.016 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 8ARM-20k-NH2 | 20000 | 1000 | 0.08 | 8 | 0.004 | 0.032 | |
| 8ARM-15k-SG | 15000 | 1000 | 0.06 | 8 | 0.004 | 0.032 | |
| Buffer Volume (phosphate) | | | 2.9 | | | | 4.8 |
| Viscosity Enhancer | | | | 0.3% HPMC | | | |
| 8ARM-20k-AA | 20000 | 1000 | 0.04 | 8 | 0.002 | 0.016 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 4ARM-20k-AA | 20000 | 1000 | 0.06 | 4 | 0.003 | 0.012 | |
| 8ARM-20k-NH2 | 20000 | 1000 | 0.02 | 8 | 0.001 | 0.008 | |
| 4ARM-20k-SGA | 20000 | 1000 | 0.1 | 4 | 0.005 | 0.02 | |
| Buffer Volume (phosphate) | | | 3.6 | | | | 5.0 |
| Viscosity Enhancer | | | | 0.3% HPMC | | | |
| 4ARM-20k-AA | 20000 | 1000 | 0.12 | 4 | 0.006 | 0.024 | |
| 8ARM-20k-NH2 | 20000 | 1000 | 0.04 | 8 | 0.002 | 0.016 | |
| 8ARM-15k-SG | 15000 | 1000 | 0.075 | 4 | 0.005 | 0.02 | |
| Buffer Volume (phosphate) | | | 4.9 | | | | 4.8 |
| Viscosity Enhancer | | | | 0.3% HPMC | | | |
| 8ARM-20k-AA | 20000 | 1000 | 0.06 | 8 | 0.003 | 0.024 | |
| 8ARM-20k-NH2 | 20000 | 1000 | 0.02 | 8 | 0.001 | 0.008 | |
| 4ARM-20k-SGA | 20000 | 1000 | 0.16 | 4 | 0.008 | 0.032 | |
| Buffer Volume (phosphate) | | | 5 | | | | 4.8 |
| Viscosity Enhancer | | | | 0.3% HPMC | | | |
| 8ARM-20k-AA | 20000 | 1000 | 0.03 | 8 | 0.0015 | 0.012 | |
| 8ARM-20k-NH2 | 20000 | 1000 | 0.02 | 8 | 0.001 | 0.008 | |
| 4ARM-20k-SGA | 20000 | 1000 | 0.1 | 4 | 0.005 | 0.02 | |
| Buffer Volume (phosphate) | | | 3.1 | | | | 4.8 |
| Viscosity Enhancer | | | | 0.3% HPMC | | | |
| 8ARM-20k-AA | 20000 | 1000 | 0.02 | 8 | 0.001 | 0.008 | |
| 8ARM-20k-NH2 | 20000 | 1000 | 0.02 | 8 | 0.001 | 0.008 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 8ARM-20k-AA | 20000 | 1000 | 0.035 | 8 | 0.00175 | 0.014 | |

TABLE 7-continued

| | | | | | | | |
|---|---|---|---|---|---|---|---|
| 8ARM-20k-NH2 | 20000 | 1000 | 0.015 | 8 | 0.00075 | 0.006 | |
| 4ARM-20k-SGA | 20000 | 1000 | 0.1 | 4 | 0.005 | 0.02 | |
| Buffer Volume (phosphate) | | | 3.1 | | | | 4.8 |
| Viscosity Enhancer | | | | 0.3% HPMC | | | |
| 8ARM-20k-AA | 20000 | 1000 | 0.039 | 8 | 0.00195 | 0.0156 | |
| 8ARM-20k-NH2 | 20000 | 1000 | 0.021 | 8 | 0.00105 | 0.0084 | |
| 4ARM-20k-SGA | 20000 | 1000 | 0.12 | 4 | 0.006 | 0.024 | |
| Buffer Volume (phosphate) | | | 3.75 | | | | 4.8 |
| Viscosity Enhancer | | | | 0.3% HPMC | | | |
| 8ARM-20k-AA | 20000 | 1000 | 0.09 | 8 | 0.0045 | 0.036 | |
| 8ARM-20k-NH2 | 20000 | 1000 | 0.03 | 8 | 0.0015 | 0.012 | |
| 4ARM-20k-SGA | 20000 | 1000 | 0.24 | 4 | 0.012 | 0.048 | |
| Buffer Volume (phosphate) | | | 9 | | | | 4.0 |
| Viscosity Enhancer | | | | 0.3% HPMC | | | |
| 8ARM-20k-AA | 20000 | 1000 | 0.075 | 8 | 0.00375 | 0.03 | |
| 8ARM-20k-NH2 | 20000 | 1000 | 0.025 | 8 | 0.00125 | 0.01 | |
| 4ARM-20k-SGA | 20000 | 1000 | 0.2 | 4 | 0.01 | 0.04 | |
| Buffer Volume (phosphate) | | | 8.55 | | | | 3.5 |
| Viscosity Enhancer | | | | 0.3% HPMC | | | |
| 8ARM-20k-AA | 20000 | 1000 | 0.06 | 8 | 0.003 | 0.024 | |
| 8ARM-20k-NH2 | 20000 | 1000 | 0.02 | 8 | 0.001 | 0.008 | |
| 4ARM-20k-SGA | 20000 | 1000 | 0.16 | 4 | 0.008 | 0.032 | |
| Buffer Volume (phosphate) | | | 8 | | | | 3.0 |
| Viscosity Enhancer | | | | 0.3% HPMC | | | |

(A) Summary of the reaction details for several representative sticky formulations;

(B) more detailed tabulation of a selection of the reaction details including moles (degradation times were measured in phosphate buffered saline (PBS) at 37° C).

Cytotoxicity & Hemolysis Evaluation

Several polymer samples were sent out to NAMSA for cytotoxicity and hemolysis evaluation. Cytotoxic effects were evaluated according to ISO 10993-5 guidelines. Hemolysis was evaluated according to procedures based on ASTM F756 and ISO 10993-4.

The polymer 8ARM-20k-NH2 & 4ARM-20k-SGA at 4.8% solution with 0.3% HPMC was found to be non-cytotoxic and non-hemolytic. The polymer 8ARM-20k-AA/8ARM-20k-NH2 (70/30) & 4ARM-20k-SGA at 4.8% solution with 0.3% HPMC was found to be non-cytotoxic and non-hemolytic. In addition, formulations involving 4ARM-20kAA and 8ARM-15k-SG were also non-cytotoxic and non-hemolytic.

Gel and Degradation Time Measurements

The gel time for all cases was measured starting from the addition of the ester until the gelation of the solution. The gel point was noted by pipetting 1 mL of the reaction mixture and observing the dropwise increase in viscosity until the mixture ceased to flow. Degradation of the polymers was performed by the addition of 1 to 10 mL of phosphate buffered saline per 1 g of the material in a 50 mL centrifuge tube and incubating the mixture at 37° C. A digital water bath was used to maintain the temperature. The degradation time was measured starting from the day of addition of the phosphate buffer to complete dissolution of the polymer into solution.

The effect of reaction buffer pH, phosphate concentration, polymer concentration and reaction temperature on the gel times were characterized. The buffer pH was varied from 7.2 to 8.0 by the dropwise addition of either 50% aqueous NaOH or 6.0 N HCl. Phosphate concentrations of 0.01, 0.02 and 0.05 M were prepared and adjusted to pH 7.4. Polymer concentrations from 2 to 20% solution were studied. Reaction temperatures of 5, 20, and 37° C. were tested by keeping the monomers, buffers, and reaction mixture at the appropriate temperature. The 5° C. environment was provided by a refrigerator and the 37° C. temperature was maintained via the water bath. Room temperature was found to be 20° C.

The effect of degradation buffer pH and the proportion of degradable amine in the polymer formulation on the degradation times were explored. The degradation buffer pH was varied from 7.2 to 9.0 by the dropwise addition of either 50% aqueous NaOH or 6.0 N HCl. The degradable amine components studied were either the 4ARM-20k-AA or the 8ARM-20k-AA, and the percent of degradable amine relative to the non-degradable amine was varied from 50 to 100%.

Figure 8:
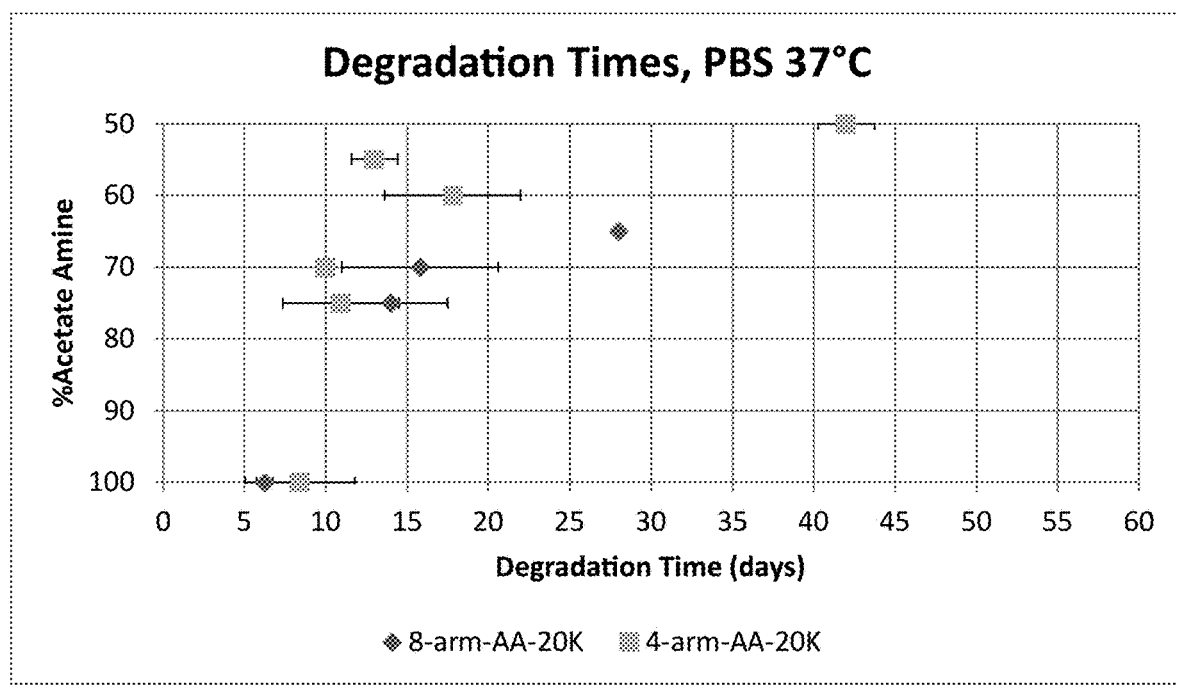
FIG. 8 shows the effect of addition of degradable acetate amine 8ARM-20k-AA or 4ARM-20k-AA on degradation times. Degradations occurred in phosphate buffered saline (PBS) at 37° C.

The degradation time is largely dependent on the buffer pH, temperature, and the monomers used. Degradation occurs primarily through ester bond hydrolysis; in biological systems, enzymatic pathways may also play a role. FIG. 8 compares the degradation times of formulations with 4ARM-20k-AA and 8ARM-20k-AA in varying amounts. In general, increasing the amount of degradable acetate amine in relation to the non-degradable amine decreases the degradation times. Additionally, in some instances, the 8ARM-20k-AA exhibits a longer degradation time than the 4ARM-20k-AA per mole equivalent, which becomes especially apparent when the percent of acetate amine drops below 70%.

Figure 9:
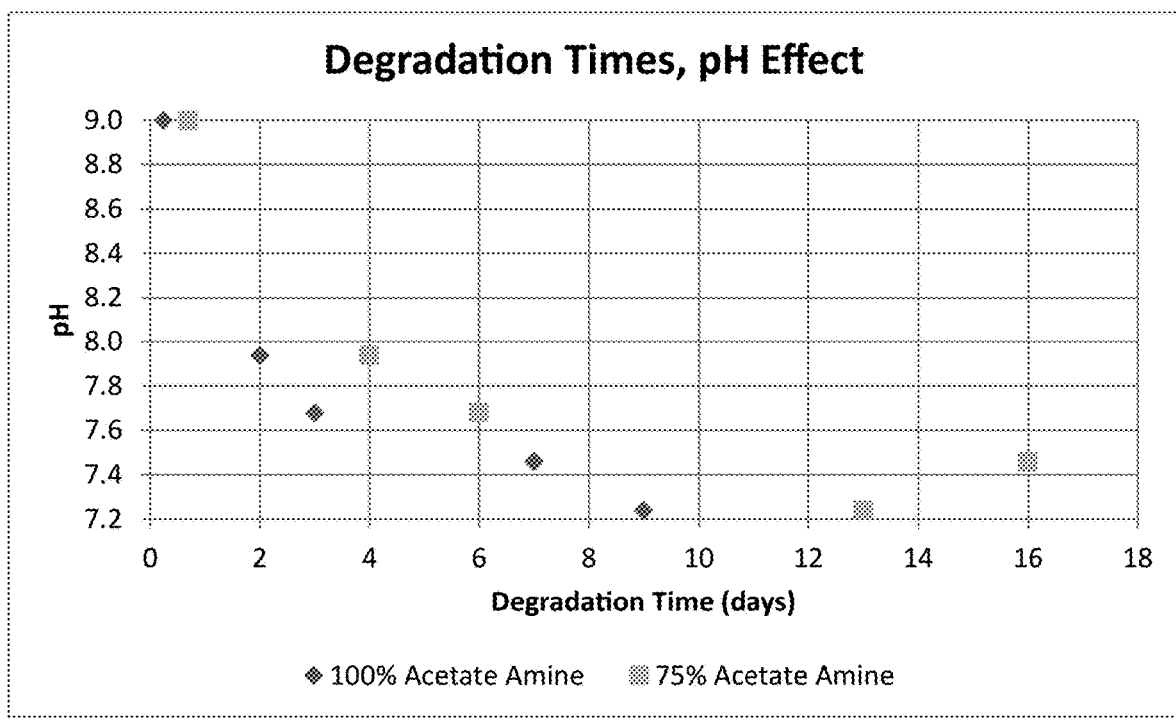
FIG. 9 shows the effect of degradation buffer pH on degradation times. Degradations occurred at 37° C.

FIG. 9 shows the effect of the buffer pH on the degradation time. The pH range between 7.2 and 9.0 was studied. In general, a high pH environment results in a greatly accelerated degradation. For example, an increase in pH from approximately 7.4 to 7.7 decreases the degradation time by about half.

Figure 10:
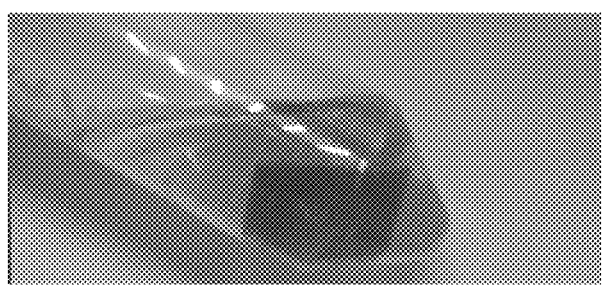
FIGS. 10A, 10B, 10C, and 10D show several photos depicting the 8ARM-20k-NH2 & 4ARM-20k-SGA at 4.8% solution with 0.3% HPMC formulation as an example of a smooth degradation process. The polymer was created in a cylindrical shape with red food dye for visualization purposes. The initial state of the polymer in degradation buffer is shown (FIG. 10A). After several days, the polymer swelled, but retained its shape (FIG. 10B). As the degradation point is approached, the polymer became soft and lost its shape (FIG. 10C). Finally, the polymer degraded into the solution (FIG. 10D).
Figure 10:
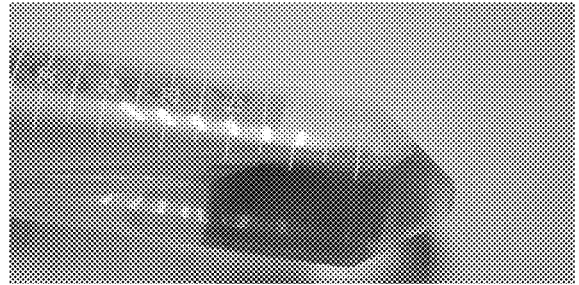
Figure 10:
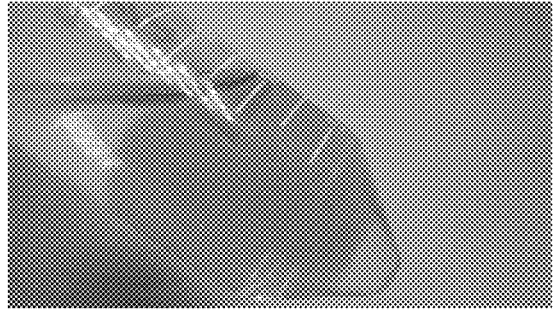
Figure 10:
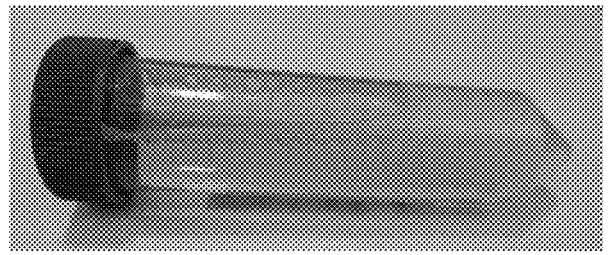

The monomers used in the formulations have also been found to play a role in the way the polymer degrades. For the 8ARM-20k-AA/8ARM-20k-NH2 (70/30) & 4ARM-20k-SGA polymer, degradation occurred homogeneously throughout the material, resulting in a "smooth" degradation process, which is depicted in FIGS. 10A, 10B, 10C, and 10D. The initial state of the polymer is shown in FIG. 10A. The polymer absorbed water and swelled slightly over the initial few days (FIG. 10B). Then, the polymer became gradually softer yet maintained its shape (FIG. 10C). Finally, the polymer lost its shape and became a highly viscous fluid (FIG. 10D). The 70/30 formulation was chosen for the 14 day ophthalmic application despite its 21 day degradation time because the polymer maintained its shape up to day 14. From day 14 up to day 21, the polymer began to lose its shape and entered the viscous fluid stage.

Figure 11:
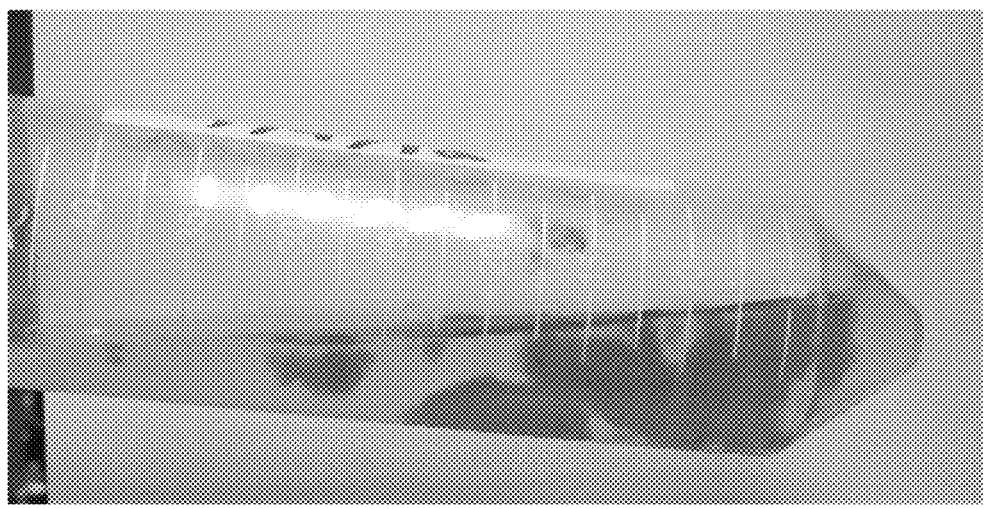
FIGS. 11A and 11B show photos depicting two different formulations as examples of fragmenting degradation processes. The polymer was created in a cylindrical shape with red food dye for visualization purposes. The 8ARM-20k-AA/8ARM-20k-NH2 (60/40) & 4ARM-20k-SGA at 4.8% solution with 0.3% HPMC is shown near the degradation point (FIG. 11A). The 4ARM-20k-AA/8ARM-20k-NH2 (70/30) & 4ARM-20k-SGA at 4.8% solution with 0.3% HPMC is shown near the degradation point (FIG. 11B).
Figure 11:
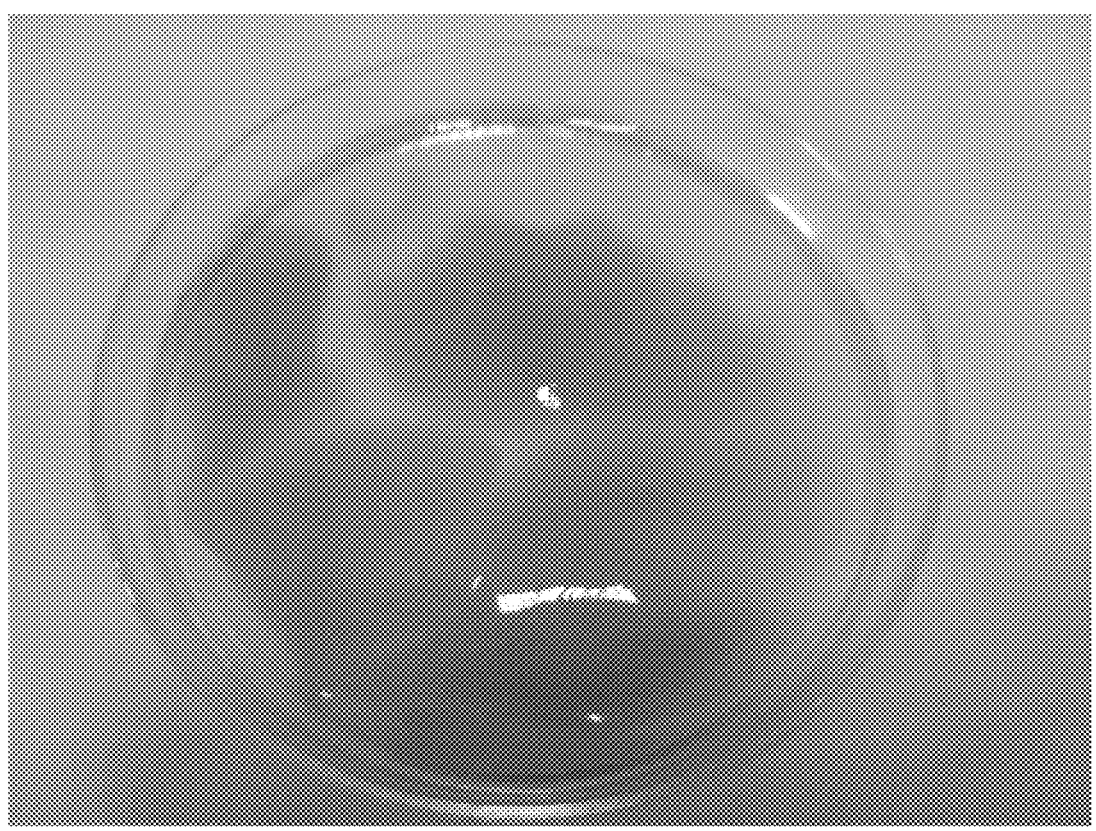

Examples of fragmenting degradation processes are shown in FIGS. 11A and 11B. When the amount of degradable amine becomes low, non-degradable regions in the polymer may occur. FIG. 11A depicts the 8ARM-20k-AA/8ARM-20k-NH2 (60/40) & 4ARM-20k-SGA formulation after approximately 80 days. FIG. 11B depicts the 4ARM-20k-AA/8ARM-20k-NH2 (70/30) & 4ARM-20k-SGA formulation, which degraded into several large fragments. For applications where the polymers are subjected to great forces, fragmentation may also occur as the polymer becomes softer and weaker over time.

Polymer Concentration

Figure 12A:
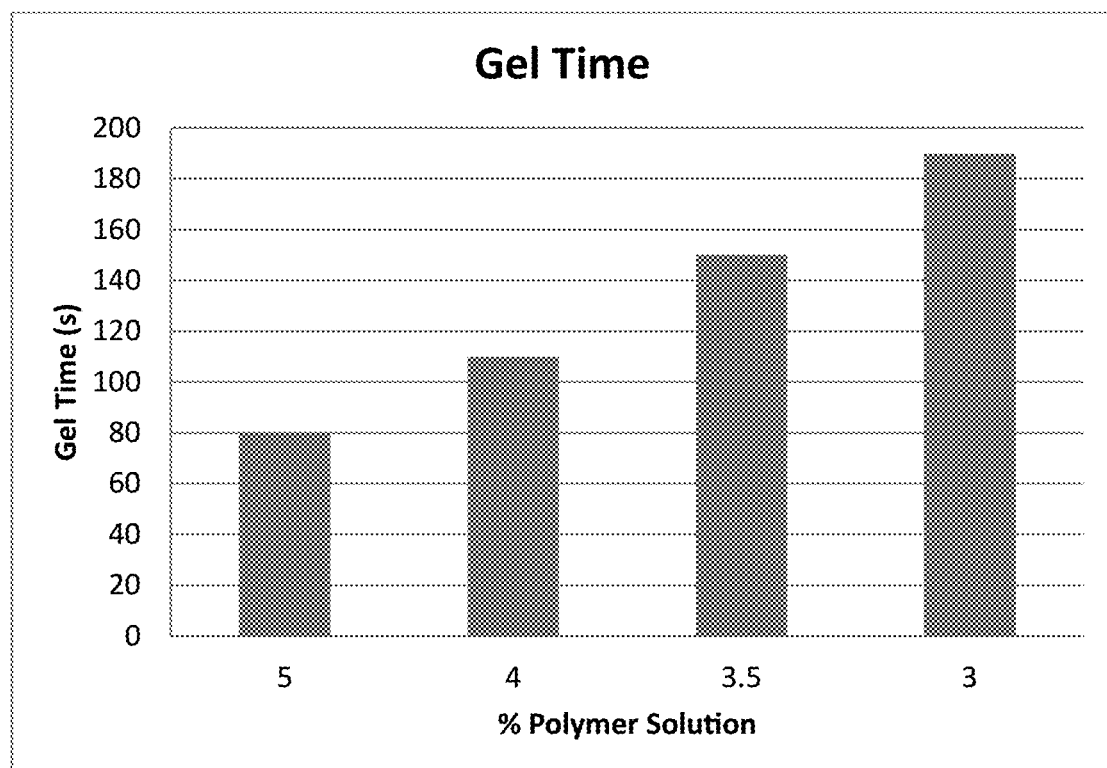
FIGS. 12A, 12B, 12C, 12D, and 12E show the effect of polymer solution on gel time (FIG. 12A), firmness (FIG. 12B), tack (FIG. 12C), elastic modulus (FIG. 12D), and swelling (FIG. 12E) for the formulation: 8ARM-20k-AA/8ARM-20k-NH2 (75/25) & 4ARM-20k-SGA with 0.3% HPMC. The error bars represent the standard deviations of 3 samples.
Figure 12B:
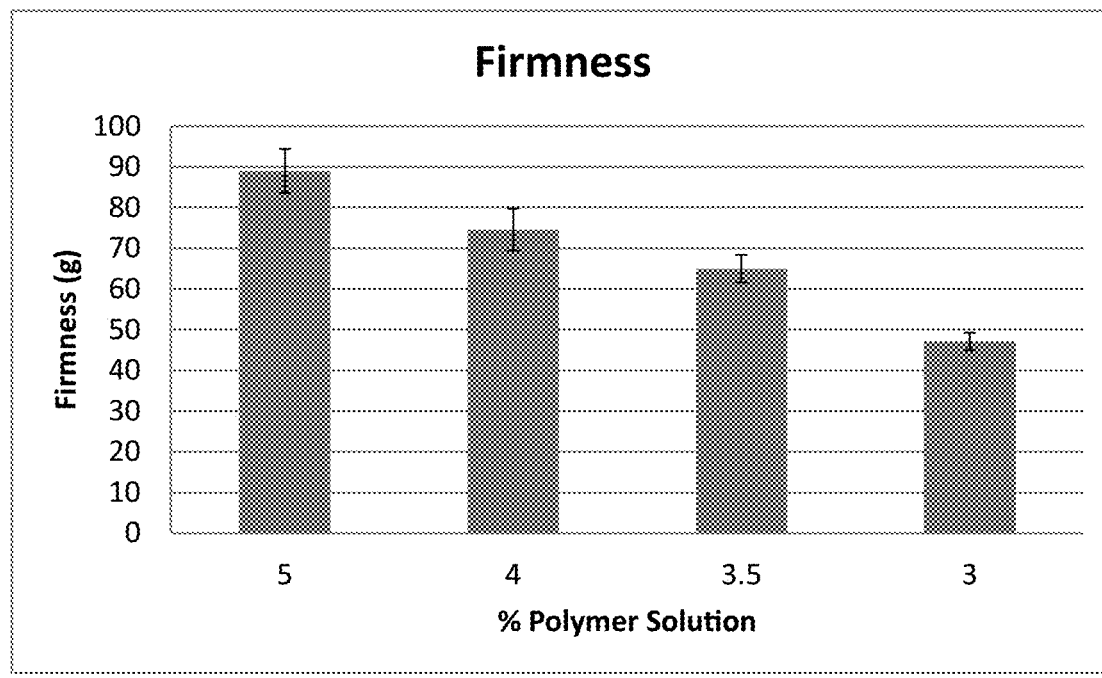
Figure 12C:
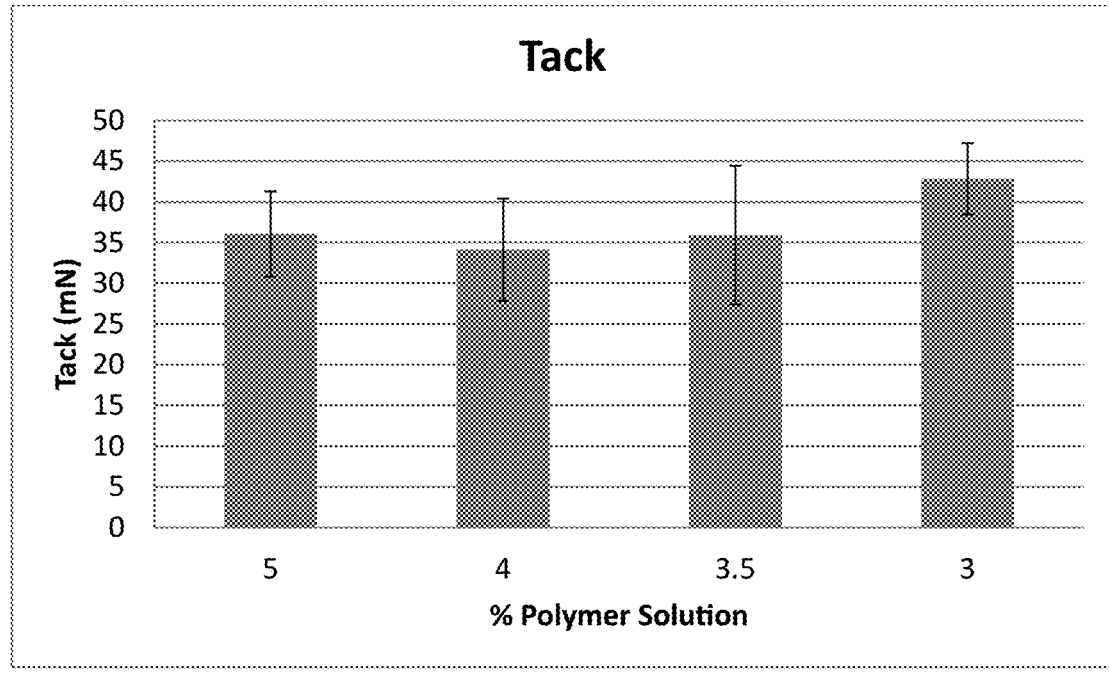
Figure 12D:
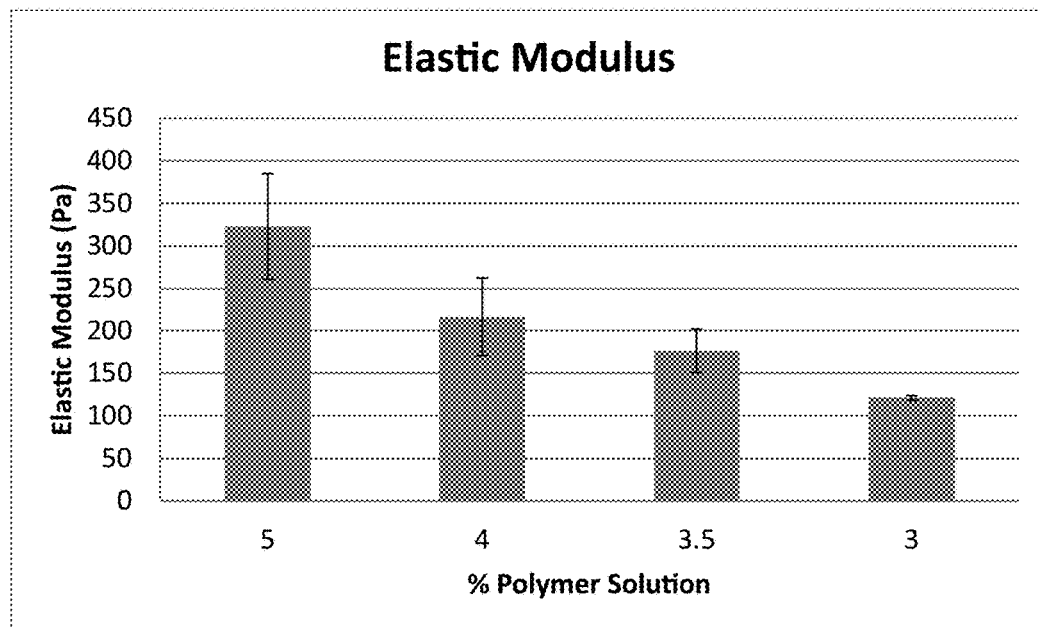
Figure 12E:
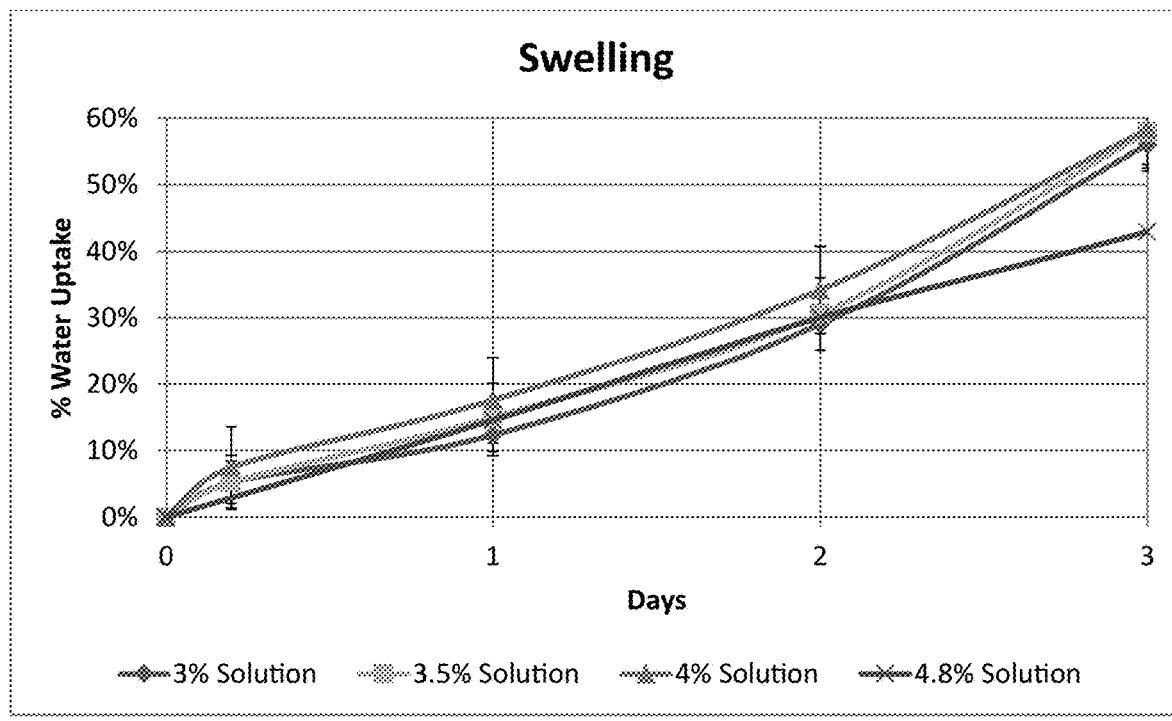

More dilute polymer solutions may be employed with minimal changes in the mechanical properties. For the formulation 8ARM-20k-AA-20K/8ARM-20k-NH2 (75/25) with 4ARM-20k-SGA and 0.3% HPMC, polymer concentrations of 3.0, 3.5 and 4.0% were studied. FIG. 12A shows the gel times, which increased steadily as the polymer concentration was lowered. The firmness decreased slightly as the polymer concentration was lowered (FIG. 12B). The tack is shown in FIG. 12C. There was essentially no change in the polymer adhesive properties. The elastic modulus decreased slightly as the polymer concentration was lowered (FIG. 12D). The swelling or water uptake is shown in FIG. 12E.

TABLE 8

(A)

| Components | MW | wt (g) | Arm | mmoles | Arms Eq | % Solution |
|---|---|---|---|---|---|---|
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate Buffer | | | | 2.5 mL 0.10 M, pH 7.80 | | 4.8 |

(B)

| Viscous Agent % (w/w) | Approximate Viscosity (cP) | Gel Time (s) | Hydrogel Surface Spread Test Category | Notes |
|---|---|---|---|---|
| 0 (Original Formulation) | 1.1 | 80 | 2 | Rigid, has "bounce". Slight elasticity. |
| 5% PVP | 1 to 5 | 90 | 2 to 3 | No change, except for a slight increase in elasticity. |
| 10% PVP | 3 to 5 | 90 | 2 to 3 | Slightly opaque, moderate increase in elasticity. Slippery. |
| 15% PVP | 5 to 10 | 100 | 2 to 3 | Opaque, definite increase in elasticity. Slippery when wet, slightly sticky when dry. |
| 20% PVP | 10 | 110 | 2 | Opaque, definite increase in elasticity. Slippery when wet, very sticky when dry. |
| 0.3% HPMC | 8.4 | 80 | 2 | No change. |
| 1.0% HPMC | 340.6 | 90 | 1 | No change. |
| 1.25% HPMC | 1,000 | 90 | 1 | No change. |
| 1.5% HPMC | 2,000 | 100 | 1 | Slightly softer, lacks "bounce". Slightly softer, lacks "bounce". |
| 2.0% HPMC | 4,000 | 100 | 1 | Slippery. |

Hydrogel Surface Spread Test Categories: 1) No spreading, tight drops that stay in place; 2) Mild spreading, drops drip slowly down; 3) Severe spreading, drops completely wet surface. Water is in category 3.

TABLE 8-continued (C)

| Sample | % Transmission @650 nm |
| --- | --- |
| 0.10M phosphate buffer, pH 7.80 | 100.0% |
| 10% PVP | 99.9% |
| 1.5% HPMC | 95.7% |
| 1.0% HPMC | 96.8% |
| 0.5% HPMC | 99.1% |
| 0.1% HPMC | 99.6% |

(A) Reaction details for specific sticky formulation;
(B) formulation results for a specific sticky formulation with a variety of viscosity enhancing agents (the hydrogel surface spread test is conducted on a hydrophilic hydrogel surface composed of 97.5% water at an angle of approximately 300; one drop of the polymer solution from a 22 gauge needle is applied to the surface before gelation);
(C) the clarity of solutions containing a variety of viscosity enhancing agents, as measured by the % transmission at 650 nm.

Methylcellulose (MC) was found to behave similarly to hypromellose (HPMC) and provided workable viscous solutions in the concentration range of 0 to 2% (w/w). However, the HPMC dissolved more readily than the MC, and the HPMC solutions possessed greater optical clarity; thus the use of HPMC was favored. Povidone (PVP) dissolved easily in the buffer, but provided minimal viscosity enhancement even at 20% (w/w).

For the most part, the polymers remain unchanged by the addition of low concentrations of HPMC or PVP. However, there was a noticeable change in the polymer around 0.3% HPMC that was characterized by an enhanced elasticity, as evidenced by the ability of the material to elongate more than usual without breakage. Above 1.5% HPMC, the polymer became slightly softer and exhibited less bounce. The gel times also remained within 10 seconds of the gel time for the formulation with no viscous agent. In the case of PVP, significant changes in the polymer occurred above 10% PVP. The polymer became more opaque with a noticeable increase in elasticity and stickiness. At 15% to 20% PVP, the polymer became similar to the sticky materials, but with a better mechanical strength. The gel times also increased by roughly 20 seconds relative to the formulation with no viscous agent. Thus, the addition of lower concentrations of PVP or HPMC to the polymer solutions may be beneficial in improving the polymer's elasticity and lubricity.

The results of the hydrogel surface spread test show that most formulations belong in category 2.

Based on the these observations, a formulation utilizing 0.3% HPMC was chosen for further evaluation. Above 1.0% HPMC, the solutions became significantly more difficult to mix and dissolution of the monomers became an issue. At 0.5% HPMC and above, the formation of air bubbles during mixing became significant. Furthermore, the solutions were not easily filtered through a 0.5 µm syringe filter to remove the bubbles. However, the 0.3% HPMC solution was easily filtered even after moderate mixing, resulting in a bubble-free, optically clear polymer.

Viscosity Measurements

The viscosities of the resulting buffer solutions were measured with the appropriately sized Cannon-Fenske viscometer tube from Ace Glass. Viscometer sizes used ranged from 25 to 300. Measurements of select solutions were performed in triplicate at both 20° C. and 37° C. The results are shown in Table 8B. To calculate the approximate dynamic viscosities, it was assumed that all the buffer solutions had the same density as water.

To characterize the rheology of the polymers during the gelation process, a size 300 viscometer was used with a formulation that was designed to gel after approximately 15 minutes. The formulation used involved the 8ARM-20k-NH2 with the 4ARM-20k-SGA ester at 2.5% solution and 0.3% HPMC. The reaction occurred in a 0.05 M phosphate buffer at a pH of 7.2. Thus, one viscosity measurement with the size 300 viscometer was obtained in about one minute and subsequent measurements may be obtained in quick succession up to the gel point.

Hydrogel Surface Spread Test

Since the surface of the retina is extremely hydrophilic, making it likely that a liquid drop will spread beyond the desired site of administration, the spread was modeled using an extremely hydrophilic surface. To model the performance of the polymer solutions on a hydrophilic surface the extent of spreading and dripping of droplets on a high water content hydrogel surface at an incline of about 30° was recorded. The hydrogel was made by dissolving 0.10 g (0.04 mol arm eq.) of 8ARM-20k-NH2 in 7 mL 0.05 M phosphate buffer at pH 7.4 in a Petri-dish, followed by the addition of 0.075 g (0.04 mol arm eq.) of 8ARM-15k-SG ester. The solution was stirred with a spatula for 10 to 20 seconds and allowed to gel, which typically took 5 to 10 minutes. The water content of the resulting polymer was 97.5%.

The test was performed by first preparing the polymer solution in the usual fashion. After thorough mixing, the polymer solution was dispensed dropwise through a 22 gauge needle onto the hydrogel surface. The results are shown in Table 8B and were divided into three general categories: 1) no spreading, tight drops that stay in place; 2) mild spreading, drops drip slowly down; 3) severe spreading, drops completely wet surface. Water is in category 3.

Swelling Measurements

The extent of swelling in the polymers during the degradation process was quantified as the liquid uptake of the polymers. A known mass of the polymer was placed in PBS at 37° C. At specified time intervals, the polymer was isolated from the buffer solution, patted dry with paper towels and weighed. The percent increase in the mass was calculated from the initial mass.

Figure 13:
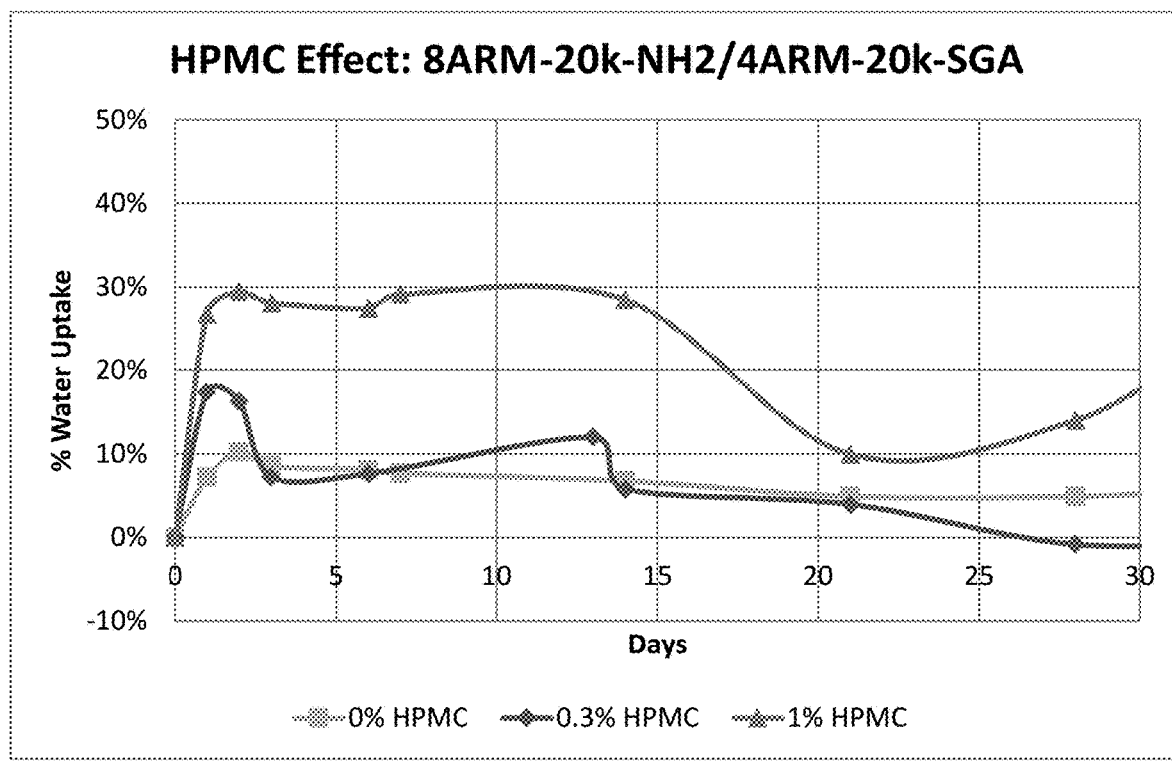
FIG. 13 shows the effect of hypromellose (HPMC) addition at 0, 0.3 and 1.0% to the polymer formulations on swelling.

The percent of water uptake by the 8ARM-20k-NH2/4ARM-20k-SGA polymers with 0, 0.3 and 1.0% HPMC is shown in FIG. 13. The 1.0% HPMC polymer absorbed up to 30% of its weight in water until day 20. After day 20, the polymer returned to about 10% of its weight in water. In comparison, the 0% HPMC polymer initially absorbed up to 10% of its weight in water, but began to lose water gradually, hovering about 5% of its weight in water. The 0.3% HPMC polymer behaved in an intermediate fashion. It initially absorbed up to 20% of its weight in water, but returned to about 10% of its weight in water after a week and continued to slowly lose water.

Specific Gravity Measurements

The specific gravity of the polymers was obtained by preparing the polymer solution in the usual fashion and pipetting 1.00 mL of the thoroughly mixed solution onto an analytical balance. The measurements were performed in triplicate at 20° C. The specific gravity was calculated by using the density of water at 4° C. as the reference.

Figure 14:
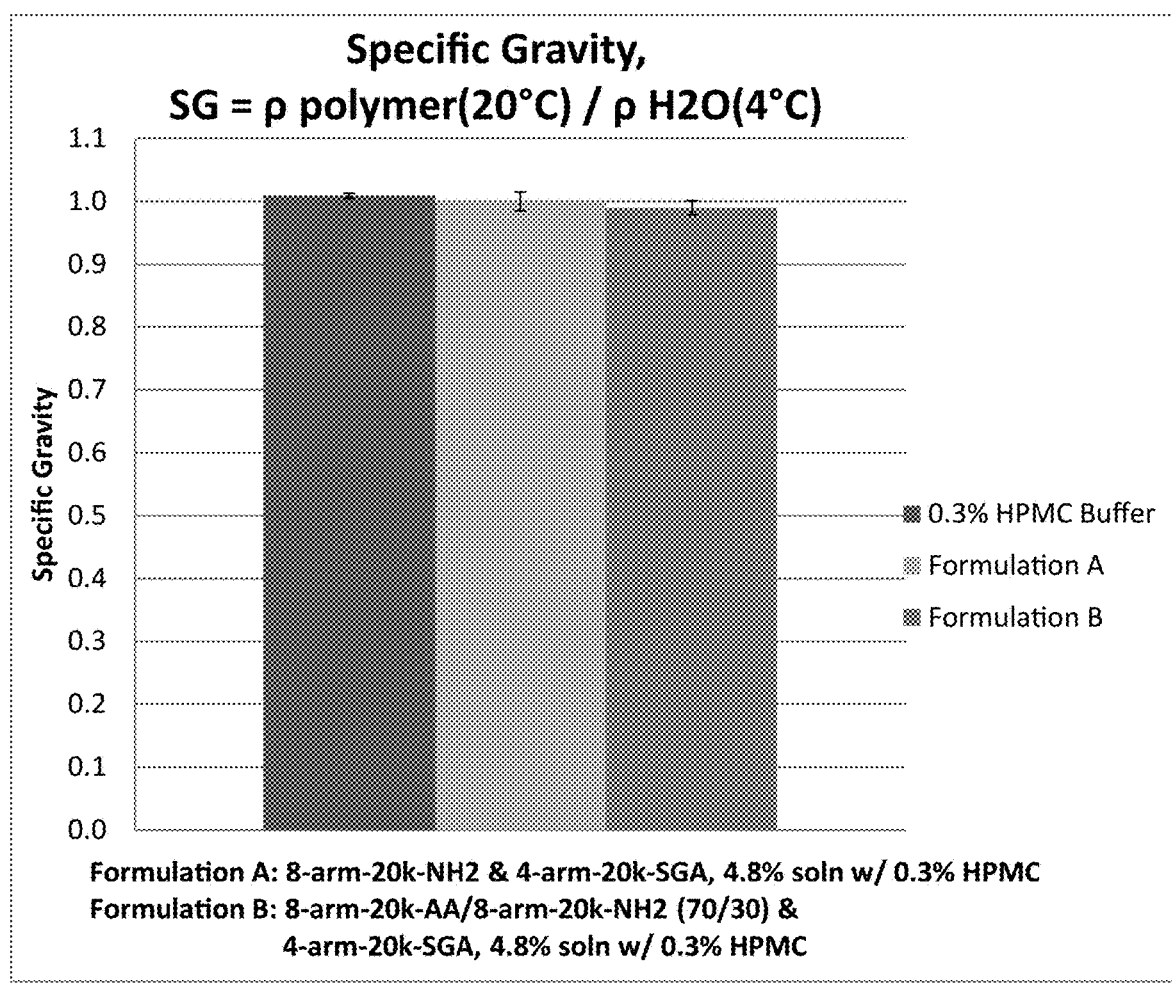
FIG. 14 shows the specific gravity of polymer solutions in relation to pure water.

The obtained values for the specific gravity are shown in FIG. 14. The specific gravity of the polymers did not differ significantly from that of the buffer solution only, both of which were essentially the same as the specific gravity of water. Exceptions may occur when the polymer solution is not filtered and air bubbles become embedded in the polymer matrix.

Barium Sulfate Suspensions

For imaging purposes, barium sulfate was added to several polymer formulations as a radiocontrast agent. Barium sulfate concentrations of 1.0, 2.0, 5.0 and 10.0% (w/v) were explored. The viscosity of the resulting polymer solutions was measured and the effect of barium sulfate addition on the polymer gel times and syringability characteristics were also studied.

Barium sulfate concentrations of 1.0, 2.0, 5.0 and 10.0% (w/v) were explored. The opaque, milky white suspensions formed similarly opaque and white polymers. No changes in the gel times were observed. Qualitatively, the polymers appeared to have similar properties to that of polymers without barium sulfate. All formulations were able to be readily dispensed through a 22 gauge needle.

Figure 15:
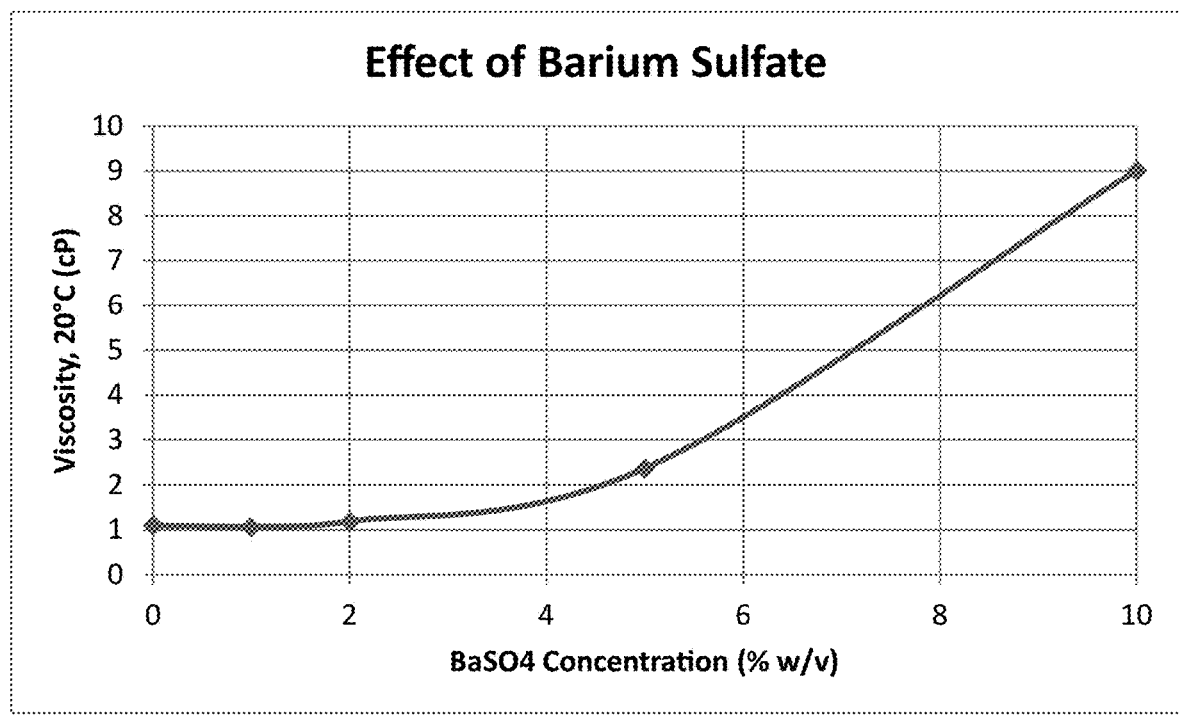
FIG. 15 shows the effect of barium sulfate ($BaSO_4$) on the solution viscosity for concentrations of 0.0, 1.0, 2.0, 5.0 and 10.0% (w/v).

The results of the viscosity measurements for barium sulfate concentrations of 1.0, 2.0, 5.0 and 10.0% are shown in FIG. 15. The viscosity remained relatively stable up to 2.0%; at 5.0%, the viscosity increased slightly to about 2.5 cP. There was a sharp increase in the viscosity to nearly 10 cP as the concentration approached 10.0%. Thus, a barium sulfate concentration of 5.0% was chosen as a balance between high contrast strength and similarity to unmodified polymer formulations.

Hydrogel Firmness, Elastic Modulus, and Adhesion

Figure 16:
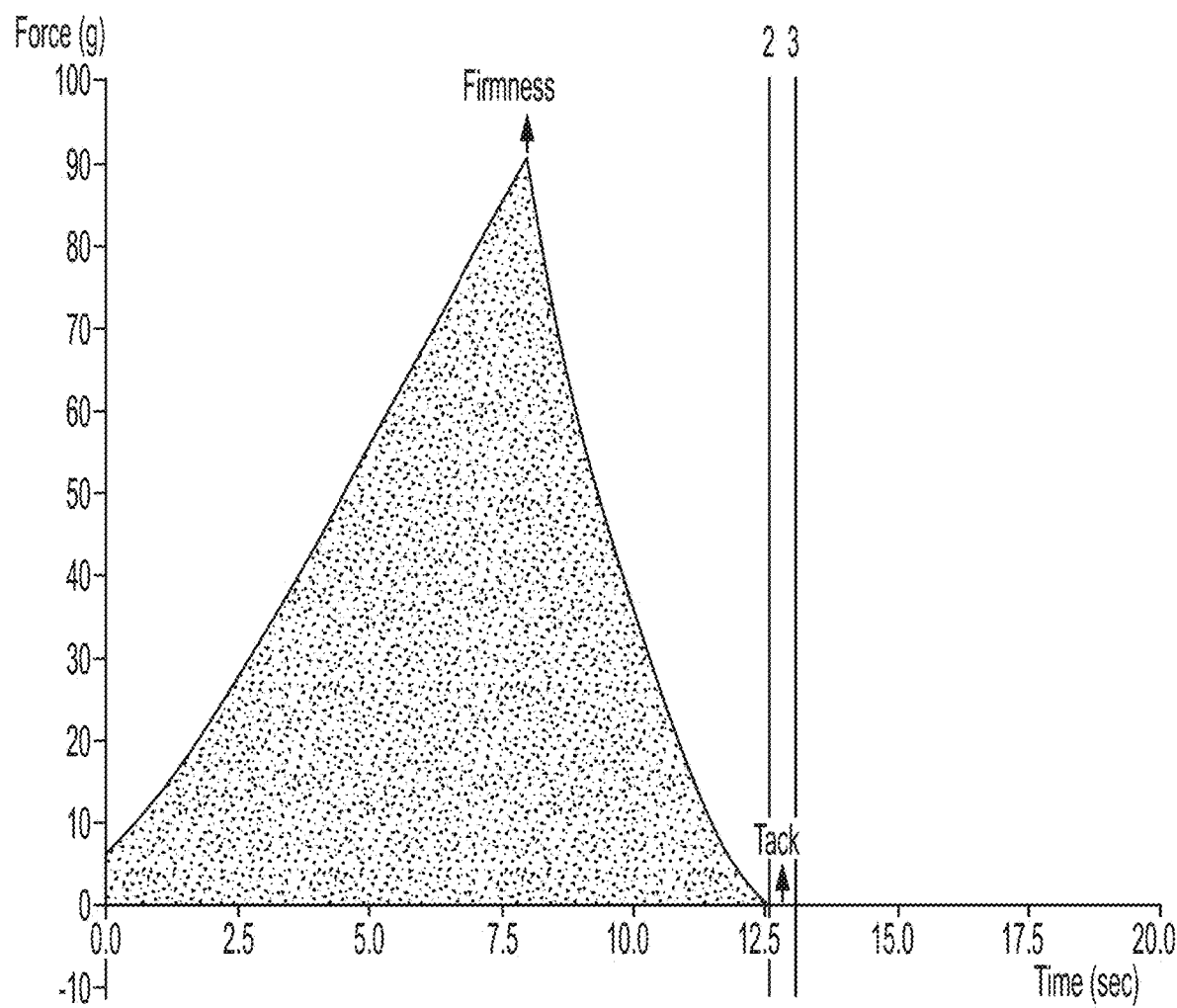
FIG. 16 shows a sample plot generated by the Texture Analyzer Exponent software running the firmness test. The peak force was recorded as the polymer firmness, which represents the point where the target penetration depth of 4 mm has been reached by the probe.

The firmness of the polymers was characterized by a Texture Analyzer model TA.XT.plus with Exponent software version 6.0.6.0. The method followed the industry standard "Bloom Test" for measuring the firmness of gelatins. In this test, the TA-8¼" ball probe was used to penetrate the polymer sample to a defined depth and then return out of the sample to the original position. The peak force measured is defined as the "firmness" of the sample. For the polymers studied, a test speed of 0.50 mm/sec, a penetration depth of 4 mm, and a trigger force of 5.0 g were used. The polymers were prepared on a 2.5 mL scale directly in a 5 mL size vial to ensure consistent sample dimensions. The vials used were ThermoScientific/Nalgene LDPE sample vials, product #6250-0005 (LOT #7163281060). Measurements were conducted at 20° C. The polymers were allowed to rest at room temperature for approximately 1 hour before measuring. Measurements were performed in triplicate for at least three samples. A sample plot generated by the Exponent software running the firmness test is given in FIG. 16. The peak of the plot represents the point at which the target penetration depth of 4 mm was reached.

Figure 17:
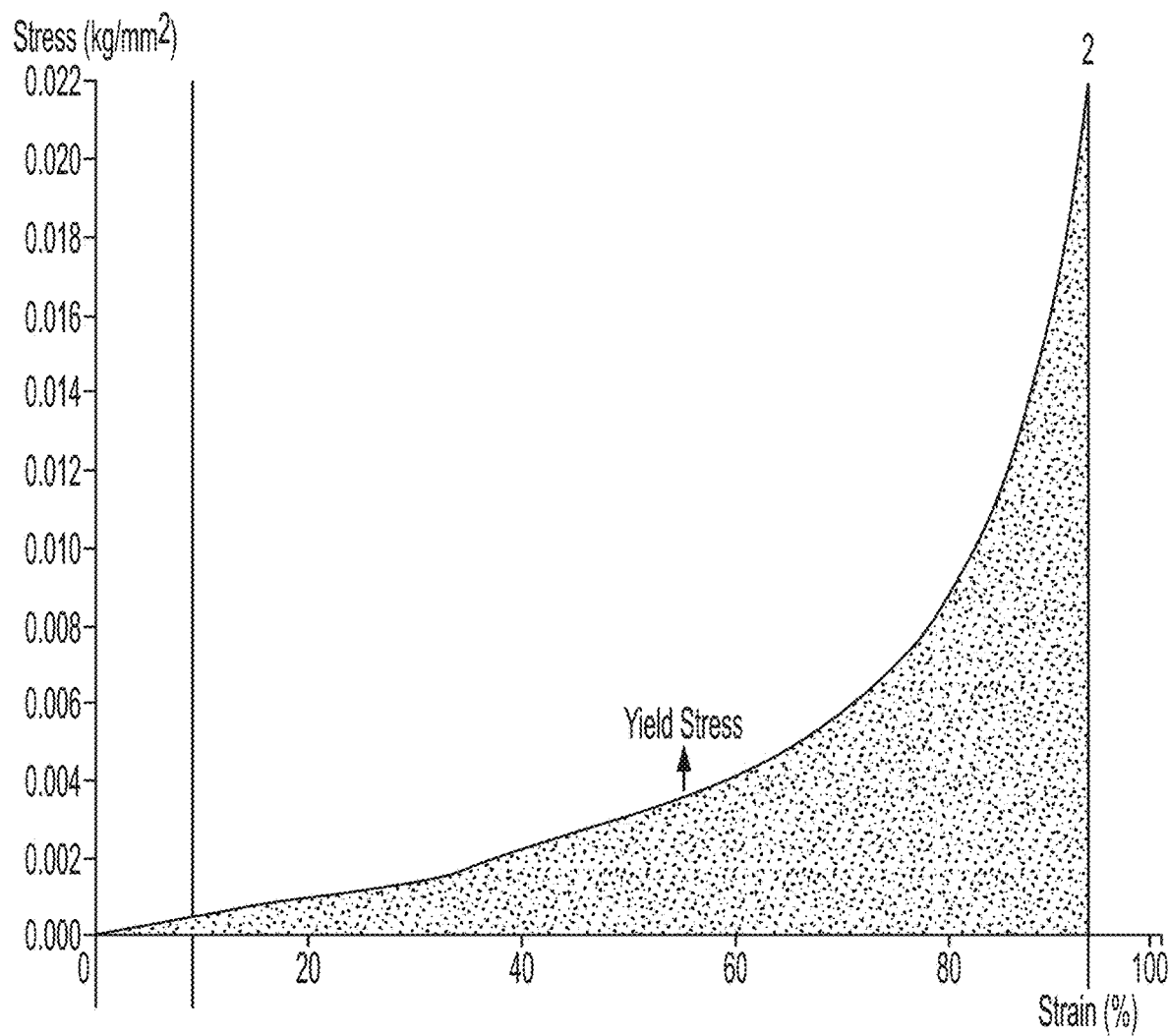
FIG. 17 shows a sample plot generated by the Texture Analyzer Exponent software running the elastic modulus test under compression. The modulus was calculated from the initial slope of the curve up to 10% of the maximum compression stress.

The elastic modulus of the polymers was characterized by a Texture Analyzer model TA.XT.plus with Exponent software version 6.0.6.0. In this test, the TA-19 Kobe probe was used to compress a polymer cylinder of known dimensions until fracture of the polymer occurs. The probe has a defined surface area of 1 cm². The modulus was calculated as the initial slope up to 10% of the maximum compression stress. For the polymers studied, a test speed of 5.0 mm/min and a trigger force of 5.0 g were used. The sample height was auto-detected by the probe. The polymers were prepared on a 2.5 mL scale directly in a 5 mL size vial cap to ensure consistent sample dimensions. The vials used were Thermo-Scientific/Nalgene LDPE sample vials, product #6250-0005 (LOT #7163281060). Measurements were conducted at 20° C. The polymers were allowed to rest at room temperature for approximately 1 hour before measuring. Measurements were performed for at least three samples. A sample plot generated by the Exponent software running the modulus test is given in FIG. 17. The polymers typically behaved elastically for the initial compression, as evidenced by the nearly linear plot.

Figure 18:
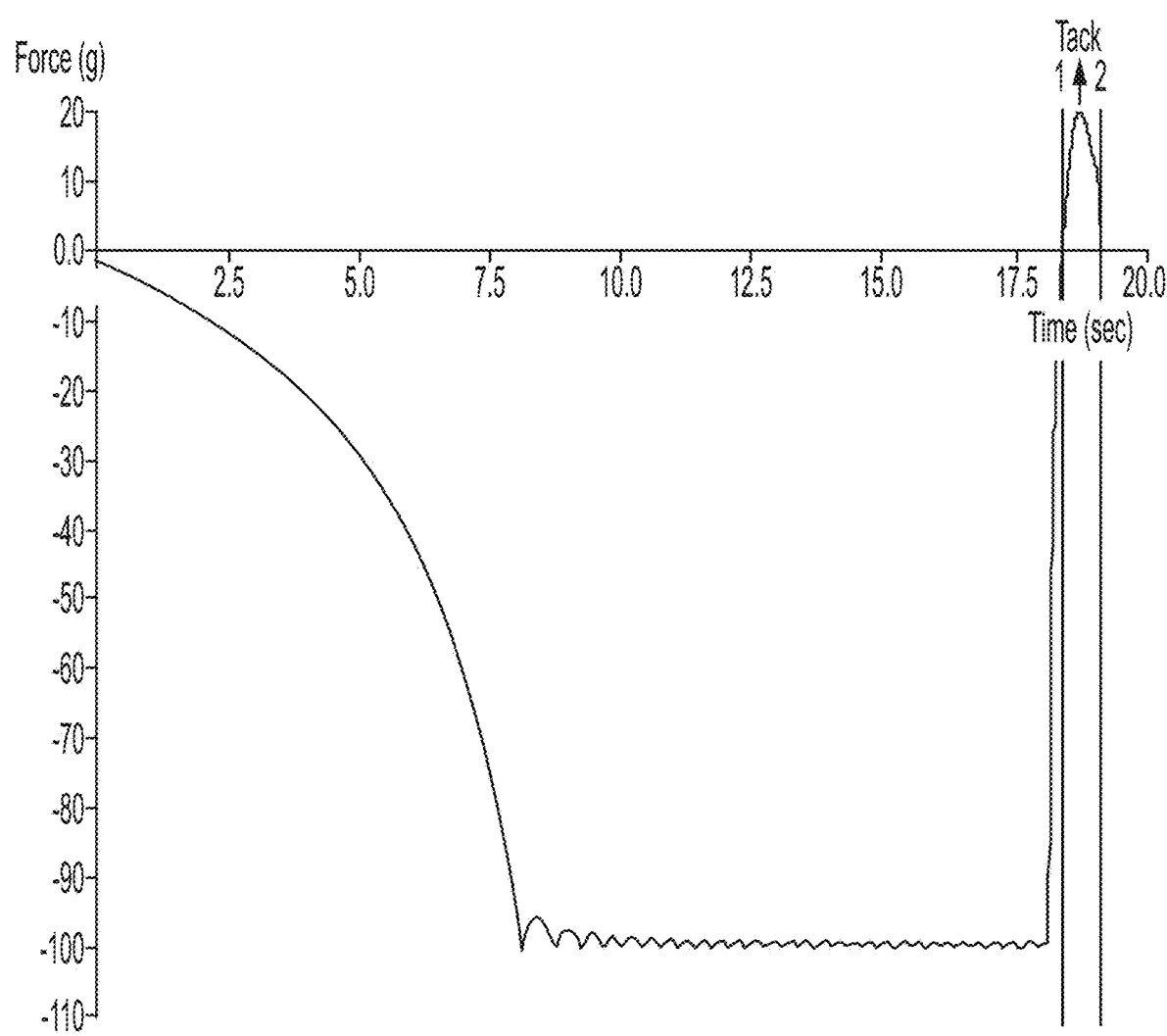
FIG. 18 shows an exemplary plot generated by the Texture Analyzer Exponent software running the adhesion test. A contact force of 100.0 g was applied for 10 seconds. The tack was measured as the peak force after lifting the probe from the sample. The adhesion energy or the work of adhesion was calculated as the area under the curve representing the tack force (points 1 to 2). The stringiness was defined as the distance traveled by the probe while influencing the tack force (points 1 and 2).

The adhesive properties of the polymers were characterized by a Texture Analyzer model TA.XT.plus with Exponent software version 6.0.6.0. In the adhesive test, the TA-57R 7 mm diameter punch probe was used to contact the polymer sample with a defined force for a certain amount of time, and then return out of the sample to the original position. An exemplary plot generated by the Exponent software running the adhesive test is given in FIG. 18. The plot begins when the probe hits the surface of the polymer. The target force is applied on the sample for a defined unit of time, represented by the constant force region in the plot. Then, the probe returns out of the sample to the original position and the adhesive force between the probe and the sample is measured as the "tack", which is the peak force required to remove the probe from the sample. Other properties that were measured include the adhesion energy or the work of adhesion, and the material's "stringiness." The adhesion energy is simply the area under the curve representing the tack force. Thus, a sample with a high tack and low adhesion energy will qualitatively feel very sticky, but may be cleanly removed with a quick pull; a sample with a high tack and high adhesion energy will also feel very sticky, but the removal of the material will be more difficult and may be accompanied by stretching of the polymer, fibril formation and adhesive residues. The elasticity of the polymer is proportional to the measured "stringiness", which is the distance the polymer stretches while adhered to the probe before failure of the adhesive bond. For the polymers studied, a test speed of 0.50 mm/sec, a trigger force of 2.0 g, and a contact force of 100.0 g and contact time of 10.0 sec were used. The polymers were prepared on a 1.0 to 2.5 mL scale directly in a 5 mL size vial to ensure consistent sample surfaces. The vials used were ThermoScientific/Nalgene LDPE sample vials. Measurements were conducted at 20° C. The polymers were allowed to rest at room temperature for approximately 1 hour before measuring. As reference materials, the adhesive properties of a standard Post-It Note® and Scotch Tape® were measured. All measurements were performed in triplicate. The averages and standard deviations were calculated.

Figure 19:
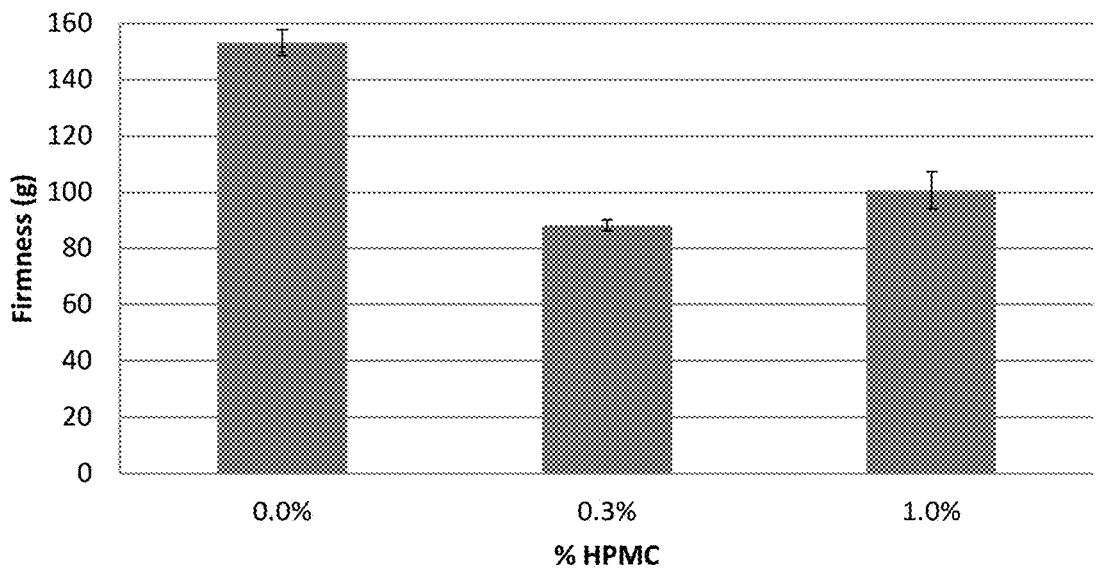
FIGS. 19A and 19B show the effect of hypromellose (HPMC) addition at 0, 0.3 and 1.0% to the polymer formulations on firmness (FIG. 19A). Effect of degradable acetate amine 8ARM-20k-AA addition at 0, 70 and 100% to the polymer formulations on firmness (FIG. 19B).
Figure 19:
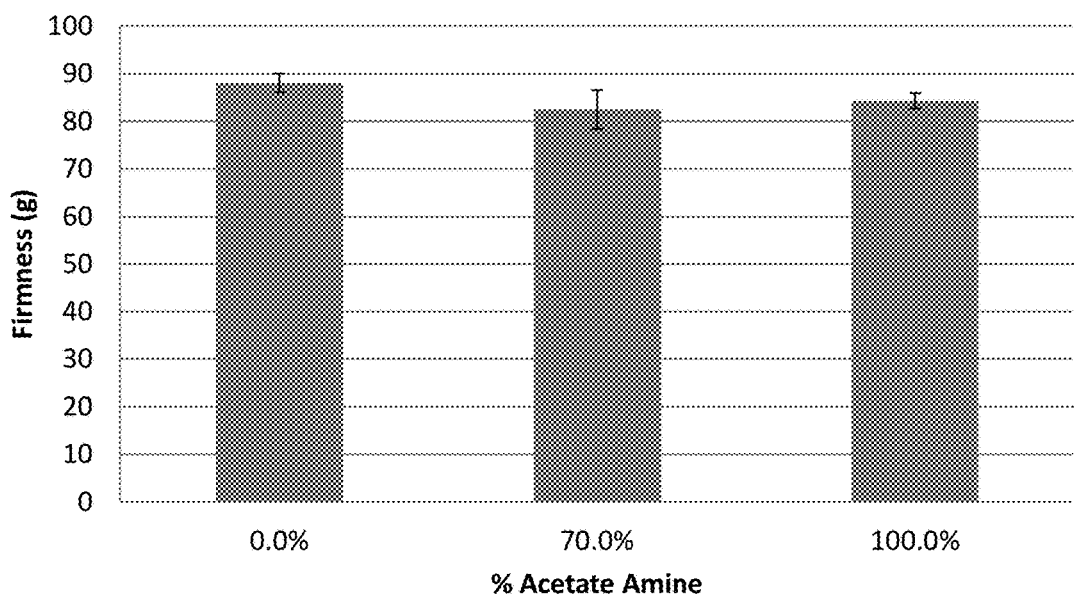
Figure 20:
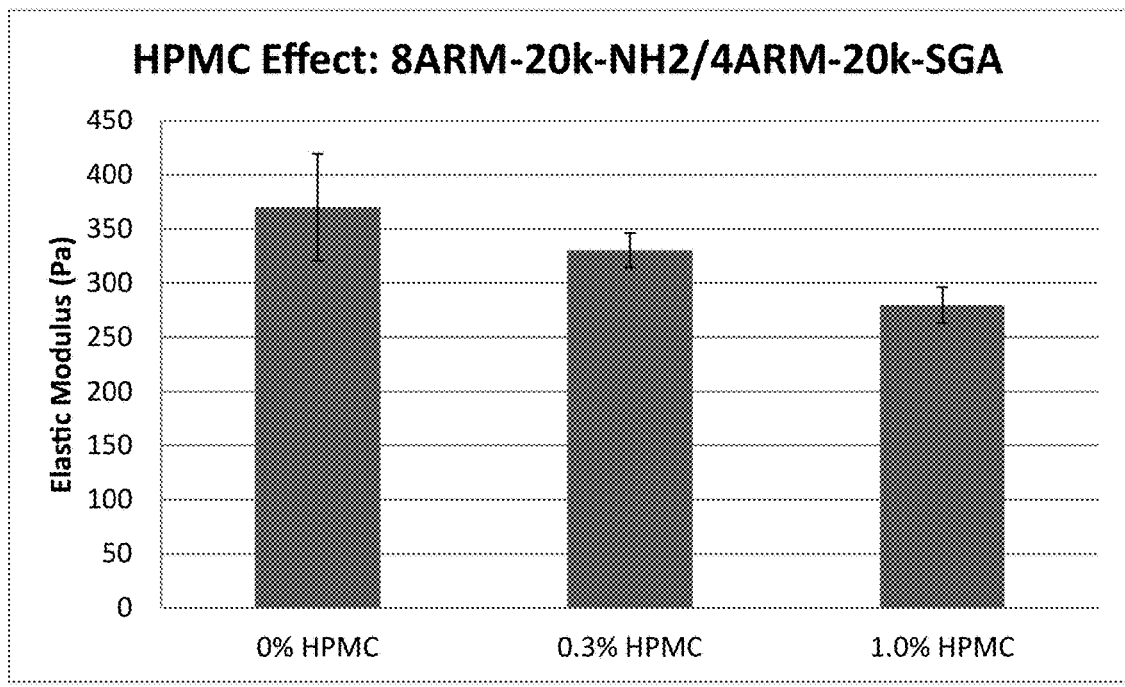
FIGS. 20A and 20B show the effect of hypromellose (HPMC) addition at 0, 0.3 and 1.0% to the polymer formulations on the elastic modulus (FIG. 20A) and shows the effect Effect of degradable acetate amine 8ARM-20k-AA addition at 0, 70 and 100% to the polymer formulations on the elastic modulus (FIG. 20B).
Figure 20:
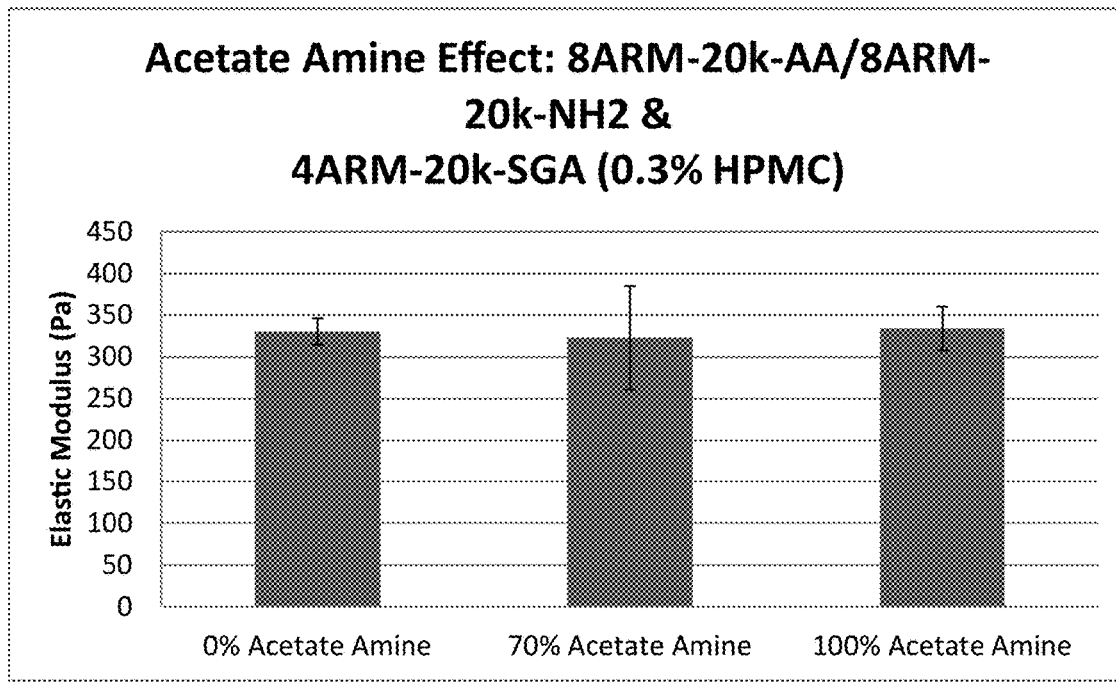
Figure 21A:
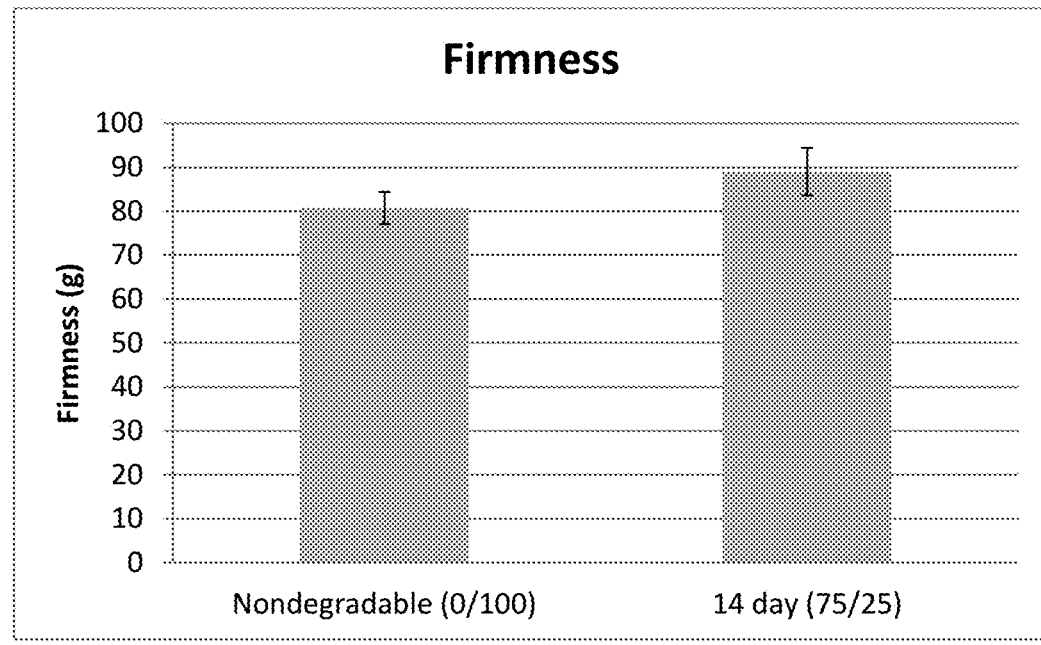
FIGS. 21A, 21B, 21C, and 21D show a comparison of the firmness (FIG. 21A), tack (FIG. 21B), adhesion energy (FIG. 21C) and stringiness (FIG. 21D) of the general polymer formulation: 8ARM-20k-AA/8ARM-20k-NH2 (x/y) & 4ARM-20k-SGA at 4.8% solution with 0.3% HPMC. The measured values for a Post-It™ note are included as a reference.
Figure 21B:
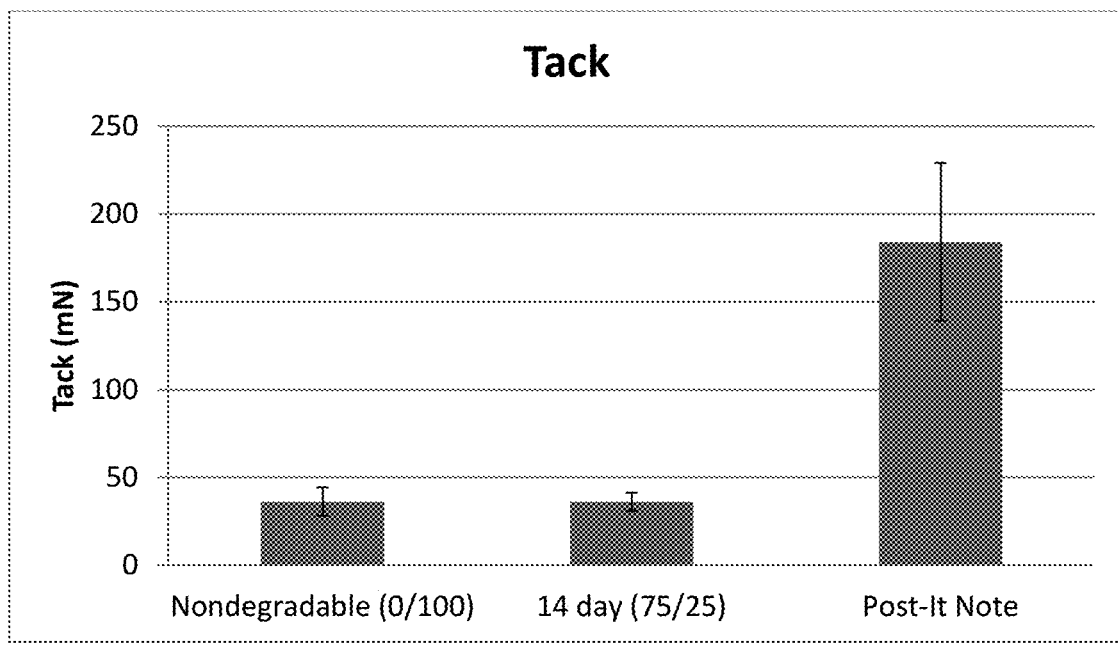
Figure 21C:
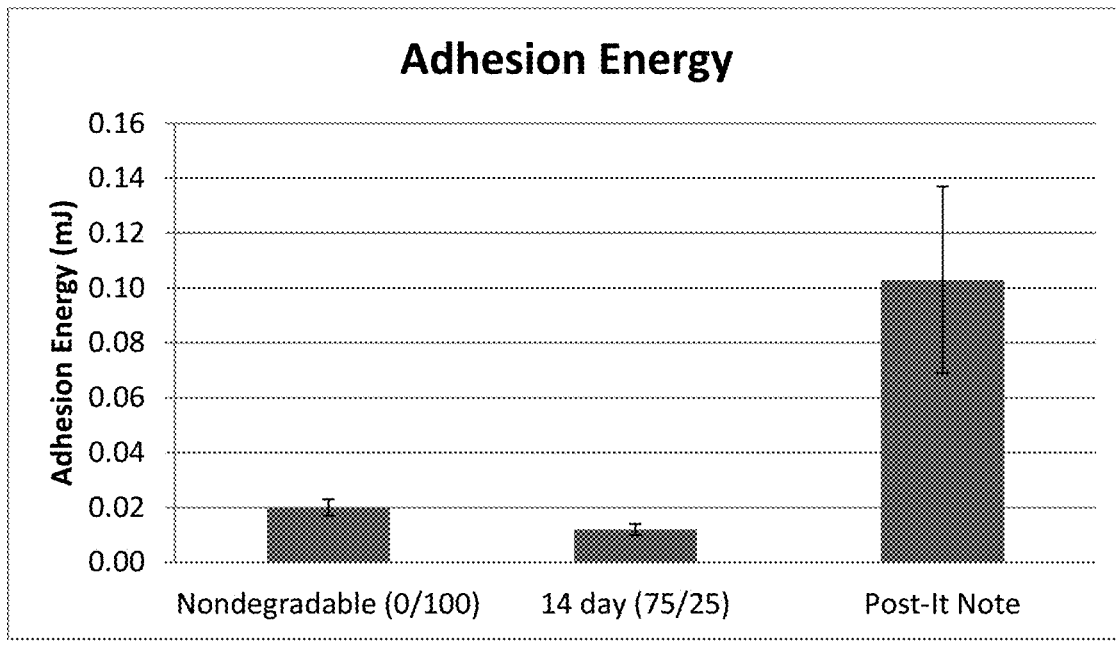
Figure 21D:
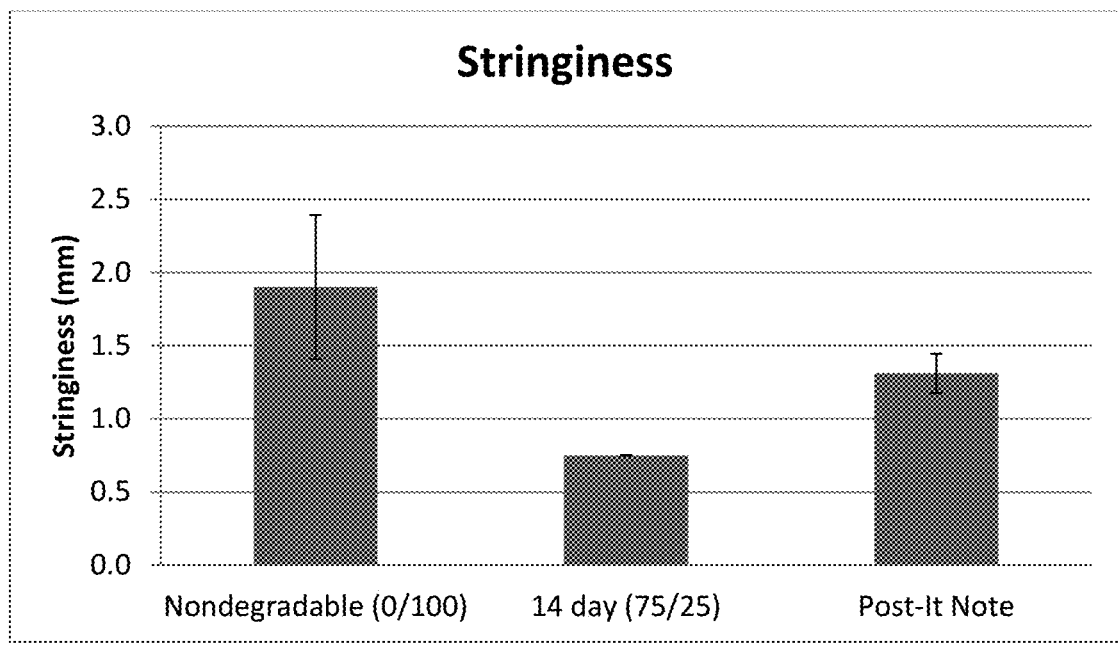

The effect of HPMC addition to the mechanical properties of the polymers was explored, along with the effect of adding degradable 8ARM-20k-AA amine. The results are shown in FIGS. 19A, 19B, 20A, and 20B. Under the stated conditions of the firmness test, it was found that the addition of 0.3% HPMC decreased the firmness of the polymer by about half (FIG. 19A). This corresponds to a slight decrease in the elastic modulus (FIG. 20A). The 1.0% HPMC polymer had approximately the same firmness as the 0.3% HPMC polymer, but a slight decrease in the elastic modulus. The disparity between the firmness and modulus tests is likely due to experimental error. The polymer solutions were not filtered, so the presence of air bubbles likely increased the errors. The water content of the polymers may also change as the polymers were sitting in the air, essentially changing the physical properties of the materials.

It was found that the addition of the degradable 8ARM-20k-AA amine did not substantially change the measured values of the firmness or the elastic modulus (FIG. 19B and FIG. 20B). The results of the adhesion testing are shown in FIGS. 21A, 21B, 21C, and 21D. The measured values for a standard commercial Post-It™ Note are also included as a reference. The polymer tack was found to be around 40 mN, which is about three times less than that of a Post-It™ Note. The adhesive properties of the polymer were not found to vary with the addition of the degradable amine.

Figure 22:
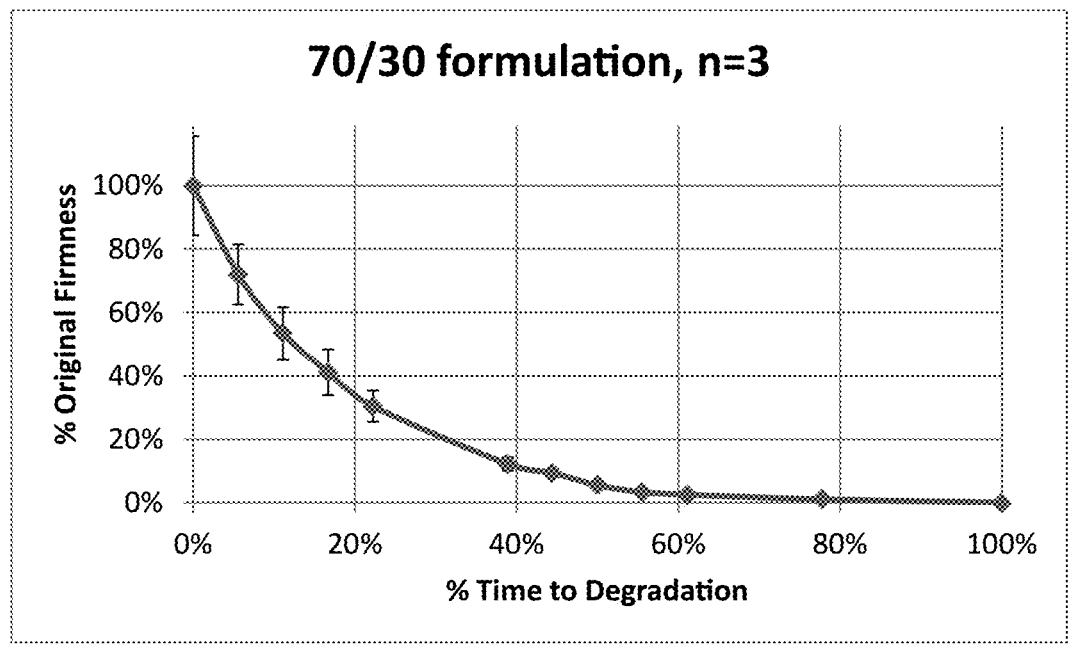
FIG. 22 shows the firmness vs. degradation time plotted as percentages for the polymer formulation: 8ARM-20k-AA/8ARM-20k-NH2 (70/30) & 4ARM-20k-SGA at 4.8% solution with 0.3% HPMC. The error bars represent the standard deviations of 3 samples. The degradation time for the polymer was 18 days.

FIG. 22 shows the firmness vs. degradation time for the 8ARM-20k-AA/8ARM-20k-NH2 (70/30) & 4ARM-20k-SGA at 4.8% solution with 0.3% HPMC. The error bars represent the standard deviations of 3 samples. The degradation time for the polymer was 18 days. The firmness of the polymer strongly correlated with the extent of degradation. Swelling may also play a role during the early stages.

Optical Clarify

A Thermo Scientific GENESYS 10S UV-Vis spectrophotometer was used to measure the optical clarity of the viscous solutions. To a quartz cuvette, 1.5 mL of the sample solution was pipetted. The buffer solution with no additives was used as the reference. The stable % transmission of the sample was recorded at 650 nm and the results are listed in Table 8C.

All of the viscous solutions under consideration were found to have acceptable to excellent optical clarity under the concentration ranges used (greater than 97% transmission). For the highly viscous solutions, air bubble formation during mixing was observed, which may be resolved by the addition of an anti-foaming agent, or through the use of a syringe filter.

Example 12: General Procedure for the Preparation of In Vivo Polymerizable Thin Films Several representative formulations for both sticky and non-sticky films are listed in Table 9 along with specific reaction details. The films had thicknesses ranging from 100 to 500 μm, and may be layered with different formulations in a composite film.

TABLE 9

(A)

| Components | Amine/Ester Molar Ratio | Buffer | % Solution |
|---|---|---|---|
| 4ARM-20k-AA & 8ARM-15k-SG | 1 | 0.15M phosphate, pH 7.99 | 19.6 |
| 4ARM-5k-NH2 & 4ARM-10k-SG | 4.5/1 | 0.05M phosphate, pH 7.40 | 39 |
| 4ARM-5k-NH2 & 4ARM-10k-SG | 1 | 0.05M phosphate, pH 7.40 | 36.4 |
| 4ARM-5k-NH2 & 4ARM-10k-SG & HPMC (1.25%) | 4.5/1 | 0.10M phosphate, pH 7.80 | 39 |
| 4ARM-2k-NH2 & 4ARM-10k-SG & HPMC (1.5%) | 8/1 | 0.10M phosphate, pH 7.80 | 30.6 |
| 4ARM-2k-NH2 & 4ARM-20k-SGA & MC (2%) | 8/1 | 0.15M phosphate, pH 7.94 | 30 |
| 4ARM-2k-NH2 & 4ARM-20k-SGA & MC (2%) | 10/1 | 0.15M phosphate, pH 7.94 | 30 |

(B)

| Components | MW | Mmoles | Wt (g) | Arm | mmoles | Arms Eq | Polymer % Solution (w/v) |
|---|---|---|---|---|---|---|---|
| 4ARM-20k-AA | 20000 | 1000 | 0.2 | 4 | 0.01 | 0.04 | |
| 8ARM-15k-SG | 15000 | 1000 | 0.075 | 8 | 0.01 | 0.04 | |
| Buffer Volume (phosphate) | | | 1.4 | | | | 19.6 |
| 4ARM-5k-NH2 | 5000 | 1000 | 0.27 | 4 | 0.05 | 0.22 | |
| 4ARM-10k-SG | 10000 | 1000 | 0.12 | 4 | 0.01 | 0.05 | |
| Buffer Volume (phosphate) | | | 1 | | | | 39.0 |
| 4ARM-5k-NH2 | 5000 | 1000 | 0.17 | 4 | 0.03 | 0.14 | |
| 4ARM-10k-SG | 10000 | 1000 | 0.34 | 4 | 0.03 | 0.14 | |
| Buffer Volume (phosphate) | | | 1.4 | | | | 36.4 |

TABLE 9-continued

| | | | | | | |
|---|---|---|---|---|---|---|
| 4ARM-5k-NH2 | 5000 | 1000 | 0.27 | 4 | 0.05 | 0.22 |
| 4ARM-10k-SG | 10000 | 1000 | 0.12 | 4 | 0.01 | 0.05 |
| Buffer Volume (phosphate) | | | 1 | | | 39.0 |
| Viscosity Enhancer | | | 1.25% HPMC | | | |

(A) Summary of the reaction details for several representative thin film formulations;
(B) more detailed tabulation of a selection of the reaction details including moles (films ranged in thickness from 100 to 500 pm).

Example 13: Preparation of Kits and their Use

Several kits were prepared with polymer formulation tested earlier. The materials used to assemble the kits are listed in Table 10 and the formulations used are listed in Table 11. The kits are typically composed of two syringes, one syringe containing the solid components and the other syringe containing the liquid buffer. The syringes are connected via a mixing tube and a one-way valve. The contents of the syringes are mixed via opening the valve and transferring the contents of one syringe into the other, repeatedly, for 10 to 20 seconds. The spent syringe and mixing tube are then removed and discarded, and the active syringe is fitted with a dispensing unit, such as a needle or cannula, and the polymer solution is expelled until the onset of gelation. In other embodiments, the viscous solution impedes the dissolution of the solid components and thus a third syringe is employed. The third syringe contains a concentrated viscous buffer that enhances the viscosity of the solution once all the components have dissolved. In some embodiments, the optical clarity of the resulting polymer is improved through the addition of a syringe filter.

All of the formulations tested were easily dispensed through a 22 gauge needle. The mixing action between the two syringes was turbulent and the introduction of a significant amount of air bubbles was apparent. Gentle mixing results in a clear material free of bubbles. Alternatively, the use of a syringe filter was found to remove bubbles without any change in the polymer properties.

TABLE 10

Materials used to fabricate kits including vendor, part number and lot number.

| Description | Vendor |
|---|---|
| Vincon Tubing, 1/8" I.D. 1/4" O.D. 1/16" wall, 100 Ft. | Ryan Herco Flow Solutions |
| 12 mL Leur-Lok Syringe | Tyco Healthcare, Kendall Monoject ™ |
| 3 mL Leur-Lok Syringe | Tyco Healthcare, Kendall Monoject ™ |
| One Way Stopcock, Female Luer Lock to Male Luer | QOSINA |
| Female Leur Lock Barb for 1/8" I.D. tubing, RSPC | QOSINA |
| Non-vented Luer Dispensor Tip Cap, White | QOSINA |
| 32 mm Hydrophilic Syringe Filter, 5 micron | PALL ® Life Sciences |

TABLE 11

The detailed contents for four different kits; the solid components are in one syringe, while the liquid components are in another syringe; a mixing tube connects the two syringes.

| Components | MW | wt (g) | Arm | mmoles | Arms Eq | % Solution |
|---|---|---|---|---|---|---|
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate Buffer | | 2.5 mL 0.10M, pH 7.80 | | | | 4.8 |
| Viscosity Enhancer | | No viscosity enhancer | | | | |
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate Buffer | | 2.5 mL 0.10M, pH 7.80 | | | | 4.8 |
| Viscosity Enhancer | | 0.3% HPMC | | | | |
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate Buffer | | 2.5 mL 0.10M, pH 7.80 | | | | 4.8 |
| Viscosity Enhancer | | 7.5% Povidone | | | | |
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate Buffer | | 2.5 mL 0.10M, pH 7.80 | | | | 4.8 |
| Viscosity Enhancer | | 1.0% HPMC | | | | |

Several additional kits were prepared with the polymer formulation that performed the best in initial trials. The materials used to assemble the kits are listed in Table 12. The kits are typically composed of two syringes, one syringe containing the solid components and the other syringe containing the liquid buffer. The syringes were loaded by removing the plungers, adding the components, purging the syringe with a gentle flow of nitrogen gas for 20 seconds, and then replacing the plunger. Finally, the plungers were depressed as much as possible to reduce the internal volume of the syringes. The specifications for the amounts of chemical components in the kits are listed in Table 13A. A summary describing the lots of kits prepared is listed in Table 13B.

Figure 23:
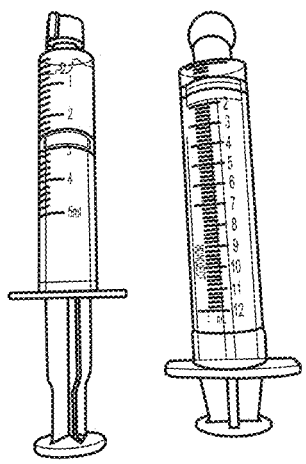
FIGS. 23A and 23B show the general assembly of directly connected syringes for use in a kit.
Figure 23:
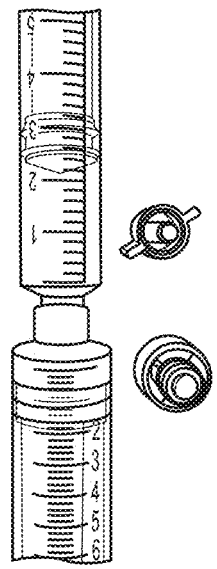

The syringes were connected directly after uncapping, the male part locking into the female part (FIGS. 23A and 23B). The contents of the syringes were mixed via transferring the contents of one syringe into the other, repeatedly, for 10 to 20 seconds. The spent syringe was then removed and discarded, and the active syringe was fitted with a dispensing unit, such as a needle or cannula, and the polymer solution was expelled until the onset of gelation. In other embodiments, the viscous solution impeded the dissolution of the solid components and thus a third syringe was employed. The third syringe contained a concentrated viscous buffer that enhanced the viscosity of the solution once all the components had dissolved.

All the formulations tested were easily dispensed through a 22 gauge needle. The mixing action between the two syringes was turbulent and the introduction of a significant amount of air bubbles was apparent. The use of a syringe filter was found to remove bubbles without any change in the polymer properties.

The prepared kits were placed into foil pouches along with one oxygen absorbing packet per pouch. The pouches were heat sealed with a CHTC-280 PROMAX tabletop chamber sealing unit. Two different modes of sealing were explored: under nitrogen and under vacuum. The settings for sealing under nitrogen were: 30 seconds of vacuum, 20 seconds of nitrogen, 1.5 seconds of heat sealing, and 3.0 seconds of cooling. The settings for sealing under vacuum were: 60 seconds of vacuum, 0 seconds of nitrogen, 1.5 seconds of heat sealing, and 3.0 seconds of cooling.

Example 14: Retinal Patch in Harvested Pig Eyes

The formulations listed in Table 14 were used and tested to assess polymers with respect to adherence, stickiness, thickness, and transparency in harvested pig eyes. A 0.15 M phosphate buffer was made by dissolving 9.00 g (0.075 mol) $NaH_2PO_4$ in 500 mL of distilled water at 25° C. with magnetic stirring. The pH was then adjusted to 7.99 with the dropwise addition of 50% aqueous NaOH. Phosphate buffered saline (PBS) was prepared by dissolving two PBS tablets (Sigma Chemical, P4417) in 400 mL of distilled water at 25° C. with vigorous shaking. The solution has the following composition and pH: 0.01 M phosphate, 0.0027 M potassium chloride, 0.137 M sodium chloride, pH 7.46.

TABLE 12

Materials used to fabricate kits including vendor, part number and lot number.

| Description | Vendor |
| --- | --- |
| 12 mLMale Luer-Lok Syringe | Tyco Healthcare, KendallMonoject ™ |
| 5 mL Female Luer Lock Syringe, Purple | QOSINA |
| Male Luer Lock Cap, Non-vented | QOSINA |
| Female Non-vented Luer Dispensor Tip Cap, White | QOSINA |
| 100 cc oxygen absorbing packet | IMPAK |
| 6.25" × 9" OD PAKVF4Mylar foil pouch | IMPAK |

TABLE 13

Specifications for kit components for the 8ARM-20k-AA/8ARM-20-NH2 & 4ARM-20k-SGA formulation with 60, 65, 70 and 75% degradable amine (A). LOT formulation summary (B).

(A)

| | Specifications | | | |
| --- | --- | --- | --- | --- |
| Components | 60/40 | 65/35 | 70/30 | 75/25 |
| 8ARM-20k-AA | 0.024-0.026 g | 0.026-0.027 g | 0.028-0.029 g | 0.030-0.031 g |
| 8ARM-20k-NH2 | 0.014-0.016 g | 0.013-0.014 g | 0.011-0.012 g | 0.009-0.010 g |
| 4ARM-20k-SGA | 0.080-0.082 g | 0.080-0.082 g | 0.080-0.082 g | 0.080-0.082 g |
| Phosphate Buffer | 2.50 mL of 0.10M phosphate, pH 7.58, 0.30% HPMC (8.48 cSt +/− 0.06 @ 20° C.) | | | |

(B)

| Formulation | Buffer pH | SealingMethod | Notes |
| --- | --- | --- | --- |
| 60/40 | 7.46 | nitrogen | |
| 60/40 | 7.58 | nitrogen | |
| 60/40 | 7.72 | nitrogen | |
| 70/30 | 7.58 | vacuum | |
| 70/30 | 7.58 | vacuum | no nitrogen purging of syringe |
| 65/35 | 7.58 | vacuum | |
| 75/25 | 7.58 | vacuum | |
| 75/25 | 7.58 | vacuum | |
| 75/25 | 7.58 | nitrogen | |
| 65/35 | 7.58 | vacuum | |
| 65/35 | 7.58 | nitrogen | |

TABLE 14

Components of Formulations Tested in Harvested Pig Eyes.

| Formulation | Components | MW | wt (g) | Arm | mmoles | Arms Eq | % Solution |
|---|---|---|---|---|---|---|---|
| A | 4ARM-5k-NH2 | 5000 | 0.2 | 4 | 0.04 | 0.16 | |
| | 4ARM-10k-SG | 10000 | 0.08 | 4 | 0.008 | 0.032 | |
| | Phosphate Buffer | | 1.5 mL 0.15M, pH 7.99 | | | | 18.7 |
| B | 4ARM-5k-NH2 | 5000 | 0.3 | 4 | 0.06 | 0.24 | |
| | 4ARM-10k-SG | 10000 | 0.12 | 4 | 0.012 | 0.048 | |
| | Phosphate Buffer | | 1.5 mL 0.10M, pH 7.80 | | | | 28 |
| C | 8ARM-20k-NH2 | 20000 | 0.04 | 8 | 0.002 | 0.016 | |
| | 4ARM-20k-SGA | 20000 | 0.08 | 4 | 0.004 | 0.016 | |
| | Phosphate Buffer | | 2.5 mL 0.10M, pH 7.80 | | | | 4.8 |

Figure 24:
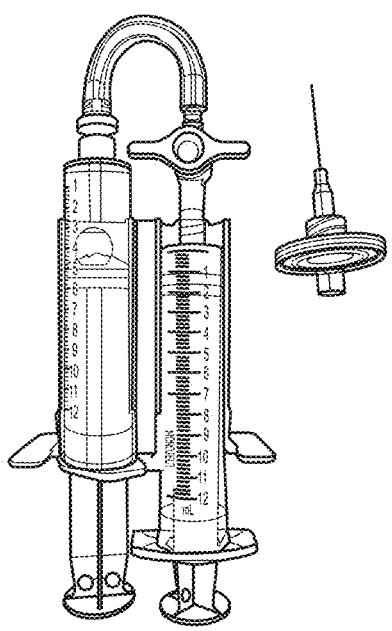
FIG. 24 shows the general design of a mixing assembly (red food dye was added for clarity purposes).
Figure 24:
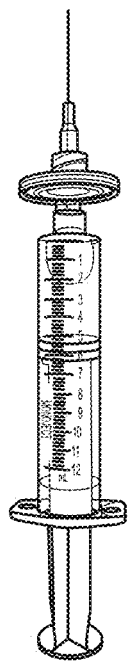

The general design and of the delivery device is shown in FIG. 24. The kits are composed of two syringes, one syringe containing the solid components and the other syringe containing the liquids. The syringes are connected via a mixing tube and a one-way valve. The contents of the syringe are mixed after opening the valve and transferring the contents of one syringe into the other, repeatedly, for 10 to 20 seconds. The spent syringe and mixing tube are then removed and discarded, and the active syringe is fitted with a needle, and the polymer solution is injected into the desired site while still in the liquid state. The liquid polymer turns in to a solid at a pre-set time at the desired site and sticks to the tissue. The optical clarity of the resulting polymer is improved by removing the air bubbles through the addition of a syringe filter.

Retinal Tissue Tests

Pig eyes were obtained and stored appropriately. Surgery was carried out carefully and the vitreous humor was separated from the retina and then the retina was cut at several places and then pinned appropriately to a Styrofoam base to create basically a flat retinal surface. The liquid suture formulations of Table 14 were mixed per the mixing procedure above and carefully deposited drop by drop over the retinal surface. Any spreading of the drop from the location was carefully observed and recorded. After test samples gelled in about 60-120 seconds, the bond strength of the adhesion was evaluated. All three formulations were applied the same way. The results are summarized in Table 15.

TABLE 15

Test Results for Formulations A-C on Retinal Tissue.

| Formulation | Results/Observations |
|---|---|
| A | It is a sticky material, gelled in 110 seconds. Not deemed "hard" enough. The material showed bubbles and it spread all over; not localized |
| B | It is a sticky material, gelled in 120 seconds. Not deemed "hard" enough. The material showed bubbles and it spread all over; not localized. |
| C | It is a less sticky material, gelled in 80 seconds. Bonding was satisfactory. Formulation bonded to retina uniformly and showed no delamination area under the microscope. The material showed bubbles and was also not localized only at the target site. Bubbles in the polymer lowered the optical clarity at the location. It also passed the blue dye leak test indicating that the bonding was strong and leak free. |

Of the 3 formulation types tested, formulation "C" was most successful even though all 3 formulations provide satisfactory results.

In order to improve the clarity and control the polymer spread, bubble formation and drop spread were evaluated.

In order to avoid bubble formation, the mixing procedure was altered, wider diameter mixing tubes were used, the syringe size was changed, antifoaming agents were added, organic solvents such as DMSO were added to the formulation, or filters were used. After examining all options, the use of 5 microns filter was deemed to be the most effective and practical procedure. The bubble formation was eliminated by using a 5 micron filter during the injection process. 0.2 Micron filter also was acceptable except for higher viscosity materials which clogged the filter.

In some instances, a higher viscosity material does not spread as fast as the lower viscosity material. Therefore, several viscosity enhancing agents were formulated with the initial formulations as shown in Table 16. The initial results for viscosity are included in Table 11. Optical clarity data is included in Table 8.

TABLE 16

Viscosity Enhanced Formulations A-C

| Formulation | Components | MW | wt. (g) | Arm | mmoles | Arms Eq | % Solution |
|---|---|---|---|---|---|---|---|
| C-1 | 8ARM-20k-NH2 | 20000 | 0.04 | 8 | 0.002 | 0.016 | |
| | 4ARM-20k-SGA | 20000 | 0.08 | 4 | 0.004 | 0.016 | |
| | Phosphate Buffer | | 2.5 mL YC-06-105 (0.10M, pH 7.80) | | | | 4.8 |
| | Viscosity Enhancer | | No viscosity enhancer | | | | |
| C-2 | 8ARM-20k-NH2 | 20000 | 0.04 | 8 | 0.002 | 0.016 | |
| | 4ARM-20k-SGA | 20000 | 0.08 | 4 | 0.004 | 0.016 | |
| | Phosphate Buffer | | 2.5 mL YC-06-105 (0.10M, pH 7.80) | | | | 4.8 |
| | Viscosity Enhancer | | 0.3% HPMC | | | | |

TABLE 16-continued

Viscosity Enhanced Formulations A-C

| Formulation | Components | MW | wt. (g) | Arm | mmoles | Arms Eq | % Solution |
|---|---|---|---|---|---|---|---|
| C-3 | 8ARM-20k-NH2 | 20000 | 0.04 | 8 | 0.002 | 0.016 | |
| | 4ARM-20k-SGA | 20000 | 0.08 | 4 | 0.004 | 0.016 | |
| | Phosphate Buffer | | 2.5 mL YC-06-105 (0.10M, pH 7.80) | | | | 4.8 |
| | Viscosity Enhancer | | 1.0% HPMC | | | | |

20 pig eyes were used in the study. After a 3-port pars plana vitrectomy (after cataract extraction by phaco) using a 23 gauge transconjunctival technique, a retinal tear or hole was created. The in vivo gelling ophthalmic pre-formulation was delivered through a 23 gauge intraocular cannula after an air/fluid exchange to create a retinal patch over the retinal lesion. It was verified that the polymer covered the retinal tear area and created a patch on the damaged retina. After about 1 minute the liquid became sold and adhered to the pathologic area of the retina. A stained liquid (trypan blue) was injected in the sub-retinal space to assess the resistance of the patch. The optical clarity met expectation.

Example 15: Retinal Patch in Live Animals (Rabbits)

This study is designed to select the best polymer in terms of adherence, stickiness, thickness, and transparency; to improve the design of the delivery system and technique; assess the efficacy of the retinal patch in keeping the retinal patch attached; and to assess the safety of the polymer in terms of inflammatory reactions or other toxic effects on the retina.

40 Rabbits are used in the study, wherein 40 eyes are subject to treatment while the fellow eye is used as the control eye. After a 3-port pars plana vitrectomy (after cataract extraction by phaco), a retain tear or hole is created. The in vivo gelling ophthalmic pre-formulation is delivered to create a retinal patch over the retinal lesion in 20 rabbits, while the entire vitreous cavity is filled with the polymer in the other 20 rabbits.

The eyes are evaluated for intraocular inflammation at day 1, 7, 15, and 30 by slit lamp evaluation, fundus evaluation, and intraocular pressure measurements. The eyes are evaluated for retinal toxicity at day 1, 7, 15, and 30 by anatomopathologic evaluation of the retina (which has or has not been in contact with the patch), multifocal ERG and +/−DNA analysis.

Example 16: Method of Treating Retinal Tear Using Local Anesthesia

This study is designed to treat a retinal tear using local anesthesia. The site of the hole, tear, or retinal detachment is identified using the existing and well established techniques. Once the hole/tear/detachment location is identified, the kits are prepared according to Example 13. Using a sharp 24 to 28 gauge needle, about 10-500 micro liters of the polymers is injected around and over the hole making sure that the entire surface area is fully covered with the polymer mixture. The viscosity of the reacting mixture does not allow excessive flow of the fluid past the site of the injection. Every attempt is made to keep the polymer injection near the hole, tear, or detachment sites by keeping the subject in a stable position. Even if a small amount flows over in another area, it will dissolve and disappear in about 14-17 days. After the tear is covered, the polymer solidifies in less than 3 minutes from the time the mixing was started. The polymer will stay at the site for 14-17 days and then dissolve and disappear.

Example 17: Clinical Trial for the Treatment of Retinal Detachment with a Hydrogel Formulation After Surgery The aim of the study is to evaluate the influence of exemplary hydrogel formulation C on thickness of the retinal nerve fiber layer by using optical coherence tomography (OCT) in patients following pars plana vitrectomy. The study will include 60 patients with a Formulation C provided herein who will be surgically treated with pars plana vitrectomy for rhegmatogenous retinal detachment and proliferative vitreoretinopathy. All subjects will be subdued to complete ophthalmologic examinations, measurements of the retinal nerve fiber layer thickness by an OCT examination, tests of the visual field with the use of an Octopus computed perimeter (automated static perimetry) and FDT-perimetry—both prior to the surgery, and on control visits for check-up during the postoperative period. All results provided by postoperative examinations will be compared with one another. The study is expected to provide data on the effect of an exemplary Formulation C on thickness of the retinal nerve fiber layer. It is also planned to show possibilities and advantages of OCT as a method of choice in the follow-up of patients with an intraocular Formulation C.

| Condition | Intervention |
|---|---|
| Rhegmatogenous Retinal Detachment | Other: Optical coherence tomography |
| Side Effect of Formulation C | Drug: Local medical treatment ofraised intraocularpressure |

Study Type: Observational. Study Design: Observational Model: Case Control.
Time Perspective: Prospective.
Eligibility
  Ages Eligible for Study: 18 Years to 80 Years
  Genders Eligible for Study: Both
  Accepts Healthy Volunteers: No
Sampling Method: Probability Sample Criteria
  Inclusion Criteria:—patients with rhegmatogenous retinal detachment
  Exclusion Criteria:
  preexistent glaucoma
  previous retinal surgery
  placement of scleral buckle during surgery
Further study details:
  Primary Outcome Measures: Evidence of Retinal Nerve Fibre Layer Thickness Change Measured by Optical Coherence Tomography, Time Frame: 6 months.

Retinal nerve fiber layer thickness change measured by optical coherence tomography might be an additional parameter that could provide new insights into clinical decision making in patients with exemplary formulation C.

Secondary Outcome Measures: Retinal Nerve Fiber Layer Thickness Change in Patients With Raised Intraocular Pressure Secondary to Formulation C, Time Frame: 6 months.

To assess whether retinal nerve fiber layer thickness changes in patients with raised intraocular pressure secondary to Formulation C.

| Groups/Cohorts | Assigned Interventions |
|---|---|
| Patients without raised IOP | Optical coherence tomography will be performed in all study patients following pars plans vitrectomy and Formulation C. A fellow eye of each patient will serve as a control. Each patient enrolled in a study will receive 4 measurements: On 7th postoperative day On 30th postoperative day On 90th postoperative day On 180th postoperative day |
| Patients with raised IOP | Optical coherence tomography will be performed in all study patients following pars plans vitrectomy and Formulation C. A fellow eye of each patient will serve as a control. Each patient enrolled in a study will receive 4 measurements: On 7th postoperative day On 30th postoperative day On 90th postoperative day On 180th postoperative day |

Example 18: Clinical Trial of Optical Coherence Tomography with a Formulation C Filled Eye The aim of this study is to determine the condition to detect the status of a macular hole by spectral domain optical coherence tomography (SD-OCT) in Formulation C filled eyes. The macular area is scanned by SD-OCT (OCT-4000, Carl Zeiss Meditec) in the patients who underwent vitreous surgery for macular hole to detect macular hole closure on postoperative days 1, 3, 7, and 30.

26 eyes are studies with an idiopathic macular hole (MH), 7 eyes with a MH retinal detachment (MHRD), and 4 eyes with a MH with myopic traction maculopathy. This is a prospective study. The age, gender, laterality of the diseased eye, stage of MH based on the Gass classification, and Snellen best-corrected visual acuity (BCVA) are recorded. The axial length is measured preoperatively in eyes with MH and postoperatively in eyes with MHRD and myopic traction maculopathy to avoid the effect of retinal detachment on the axial length. The presence of a posterior staphyloma within the posterior vascular arcade is determined by ophthalmoscopy and ultrasonography.

| Condition | Intervention |
|---|---|
| Macular Hole | Procedure: Vitreous surgery |

Study Type: Observational
Study Design: Observational Model: Cohort
Time Perspective: Prospective
Eligibility
Ages Eligible for Study: 35 Years to 85 Years. Genders Eligible for Study: Both. Accepts Healthy Volunteers: No. Sampling Method: Non-Probability Sample.

Study Population. The patients who have a vitreous surgery for macular hole, macular hole retinal detachment, myopic traction maculopathy and examined spectral domain optical coherence tomography preoperatively and postoperatively.
Criteria Inclusion Criteria: the patients who had a vitreous surgery for macular hole, macular hole retinal detachment, macular hole with myopic traction maculopathy and examined spectral domain optical coherence tomography preoperatively and postoperatively.

Exclusion Criteria: the patients who had vitreous surgery for other disease; the patients who did not have postoperative examination of spectral domain optical coherence tomography.
Further study details Primary Outcome Measures: macular hole closure detected by spectral domain optical coherence tomography, Time Frame: Change from preoperative status up to postoperative day 30. The macular hole closure in eyes with Formulation C is detected by spectral domain optical coherence tomography.

Secondary Outcome Measures: preoperative and postoperative vision. The vision is measured preoperatively and postoperative day 30. The preoperative and postoperarive vision are measured.

| Groups/Cohorts | Assigned Interventions |
|---|---|
| Macular hole The patients of idiopathic macular hole enrolled in the study | Procedure: Vitreous surgery Vitreous surgery is performed to treat the original disease not for the study. |
| Macular hole retinal detachment The patients of macular hole retinal detachment enrolled in the study | Procedure: Vitreous surgery Vitreous surgery is performed to treat the original disease not for the study. |
| Myopic traction maculopathy The patients of macular hole with myopic traction maculopathy enrolled in the study | Procedure: Vitreous surgery Vitreous surgery is performed to treat the original disease not for the study. |

Standard pars plana vitrectomy is performed. The internal limiting membrane (ILM) is removed after making it visible with triamcinolone acetonide or indocyanine green in all eyes. Preoperative cataracts are graded as mild (nuclear sclerosis 1+) or moderate to advanced (nuclear sclerosis 2+ or 3+), and phacoemulsification with implantation of an intraocular lens is performed on all cataractous eyes higher than grade 1. A Formulation C is used to fill the retina.

All surgery is performed under retrobulbar anesthesia, and a written informed consent is obtained from all patients after a full explanation of the purpose and possible complications of the treatment. The entire macular area is scanned by SD-OCT in the sitting position to avoid missing a MH. The 5-line raster mode is used to obtain high quality images on postoperative days 1, 3, 7, and 30. The ability to detect a closed MH or the status of the foveal detachment or schisis by the SD-OCT is evaluated, and the pre- and postoperative factors that affected the OCT images are investigated.

What is claimed is:
1. A composition for the treatment of retinal detachment, comprising:
(a) multi-ARM nucleophilic polyol monomers having more than two nucleophilic arms, wherein each nucleophilic arm comprises a polyethylene glycol chain and terminates in a nucleophilic group selected from a hydroxyl, thiol, and amino;

(b) multi-ARM electrophilic polyol monomers having more than two electrophilic arms, wherein each electrophilic arm comprises a polyethylene glycol chain and terminates in an electrophilic group selected from an epoxide, maleimide, succinimidyl, and an alpha-beta unsaturated ester; and (c) sodium hyaluronate;

wherein the viscosity of the composition is at least 4000 cP wherein the composition gels when placed in the eye of a subject with retinal detachment.

2. The composition of claim 1, wherein the composition further comprises a buffer providing a pH range of about 6.0 to about 8.5.

3. The composition of claim 1, wherein the composition further comprises a therapeutic agent.

4. A composition for the treatment of retinal detachment, comprising:
(a) multi-ARM nucleophilic polyol monomers having more than two nucleophilic arms, wherein each nucleophilic arm comprises a polyethylene glycol chain and terminates in a nucleophilic group selected from a hydroxyl, thiol, and amino;
(b) multi-ARM electrophilic polyol monomers having more than two electrophilic arms, wherein each electrophilic arm comprises a polyethylene glycol chain and terminates in an electrophilic group selected from an epoxide, maleimide, succinimidyl, and an alpha-beta unsaturated ester; and
(c) sodium hyaluronate;

wherein the viscosity of the composition is at least 4000 cP, wherein the nucleophilic arms of the multi-ARM nucleophilic polyol monomers are selected from

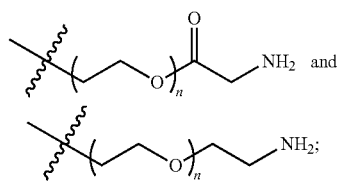

wherein n is 1-200.

5. The composition of claim 1, wherein the multi-ARM nucleophilic polyol monomers are selected from

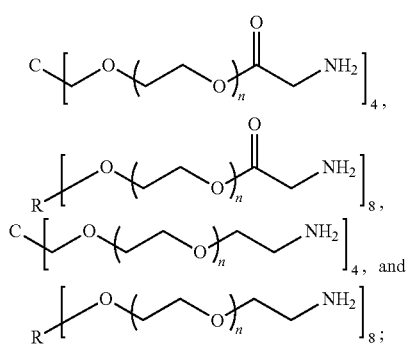

wherein R is hexaglycerol or tripentaerythritol and wherein n is 1-200.

6. A composition for the treatment of retinal detachment, comprising:
(a) multi-ARM nucleophilic polyol monomers having more than two nucleophilic arms, wherein each nucleophilic arm comprises a polyethylene glycol chain and terminates in a nucleophilic group selected from a hydroxyl, thiol, and amino;
(b) multi-ARM electrophilic polyol monomers having more than two electrophilic arms, wherein each electrophilic arm comprises a polyethylene glycol chain and terminates in an electrophilic group selected from an epoxide, maleimide, succinimidyl, and an alpha-beta unsaturated ester; and
(c) sodium hyaluronate;

wherein the viscosity of the composition is at least 4000 cP, wherein the electrophilic arms of the multi-ARM electrophilic polyol monomers are selected from

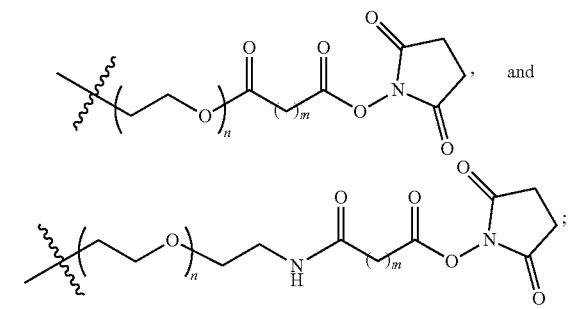

wherein m is 2 or 3 and n is 1-200.

7. The composition of claim 1, wherein the multi-ARM electrophilic polyol monomers are selected from

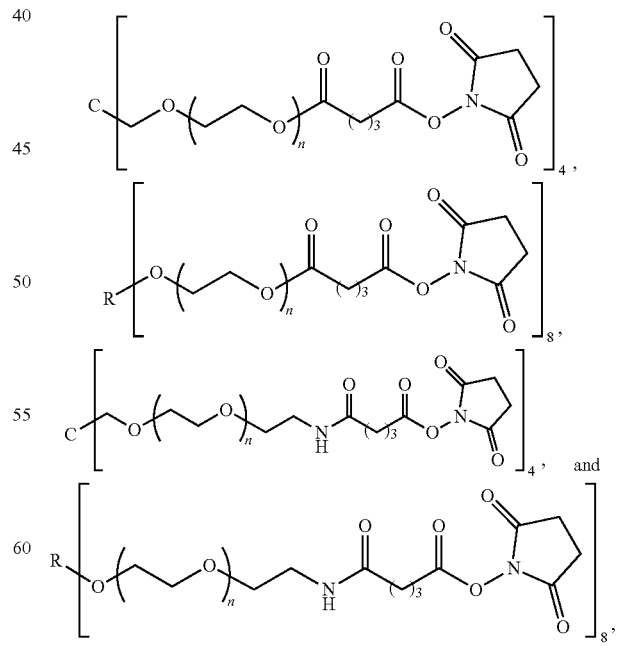

wherein R is hexaglycerol or tripentaerythritol and n is 1-200.

8. The composition of claim 1, wherein the composition comprises the following multi-ARM polyol monomers:

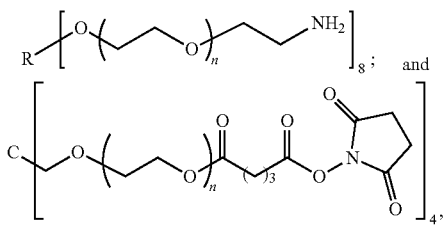

wherein R is hexaglycerol or tripentaerythritol, and wherein n is such that the molecular weight of each of the polyol monomer is 20 kDa.

9. The composition of claim 8, wherein the multi-ARM polyol monomer is in a hydrochloride salt form.

10. The composition of claim 1, wherein the multi-ARM nucleophilic polyol monomers comprise

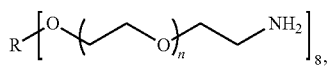

wherein R is hexaglycerol or tripentaerythritol, and wherein n is 1-200; and
the multi-ARM electrophilic polyol monomers comprise

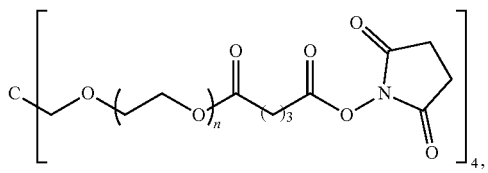

wherein n is 1-200.

11. The composition of claim 10, wherein the multi-ARM nucleophilic polyol monomer is in a hydrochloride salt form.

12. The composition of claim 1, wherein the composition further comprises a dye.

13. A method of treating retinal detachment in a patient, comprising delivering a composition of claim 1 to a site of a retinal tear in a human eye, the composition comprising:
(a) multi-ARM nucleophilic polyol monomers having more than two nucleophilic arms, wherein each nucleophilic arm comprises a polyethyleneglycol chain and terminates in a nucleophilic group selected from a hydroxyl, thiol, and amino;
(b) multi-ARM electrophilic polyol monomers having more than two electrophilic arms, wherein each electrophilic arm comprises a polyethyleneglycol chain and terminates in an electrophilic group selected from epoxide, maleimide, succinimidyl, and an alpha-beta unsaturated ester; and
(c) sodium hyaluronate;
wherein the viscosity of the composition is at least 4000 cP;
and wherein the composition polymerizes and/or gels to form a biocompatible retinal patch when delivered to the site of the retinal tear to treat the retinal detachment in the patient.

14. The method of claim 13, wherein the composition further comprises a buffer providing a pH range of about 6.0 to about 8.5.

15. The method of claim 13, wherein the composition further comprises a therapeutic agent.

16. The method of claim 13, wherein the nucleophilic arms of the multi-ARM nucleophilic polyol monomers are selected from

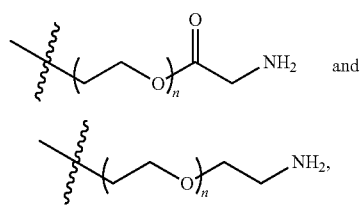

wherein n is 1-200.

17. The method of claim 13, wherein the multi-ARM nucleophilic polyol monomers are selected from

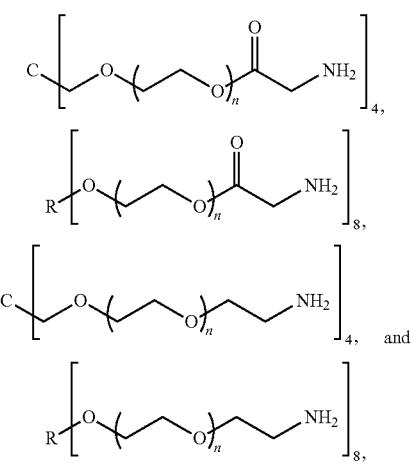

wherein R is hexaglycerol or tripentaerythritol, and wherein n is 1-200.

18. The method of claim 13, wherein the composition comprises the following multi-ARM polyol monomers:

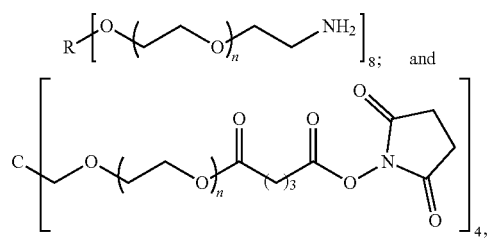

wherein R is hexaglycerol or tripentaerythritol; and wherein n is 1 to 200.

19. The method of claim 18, wherein the multi-ARM polyol monomer is in a hydrochloride salt form.

20. The method of claim 13, wherein the multi-ARM nucleophilic polyol monomers comprise

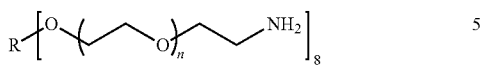

wherein R is hexaglycerol or tripentaerythritol, and wherein n is 1-200; and
the multi-ARM electrophilic polyol monomers comprise

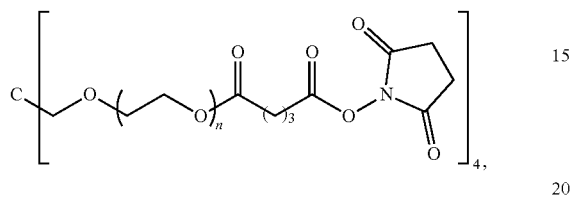

wherein n is 1-200.

21. The method of claim 20, wherein the multi-ARM nucleophilic polyol monomer is in a hydrochloride salt form.

22. The method of claim 13, wherein the composition further comprises a dye.

* * * * *